(12) United States Patent
Talasaz et al.

(10) Patent No.: US 11,519,031 B2
(45) Date of Patent: *Dec. 6, 2022

(54) NON-INVASIVE PRENATAL DIAGNOSIS OF FETAL GENETIC CONDITION USING CELLULAR DNA AND CELL FREE DNA

(71) Applicant: Illumina, Inc., San Diego, CA (US)

(72) Inventors: AmirAli Hajhossein Talasaz, Menlo Park, CA (US); Gordon M. Cann, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 149 days.

This patent is subject to a terminal disclaimer.

(21) Appl. No.: 16/947,922

(22) Filed: Aug. 24, 2020

(65) Prior Publication Data
US 2021/0032696 A1 Feb. 4, 2021

Related U.S. Application Data

(60) Continuation of application No. 15/959,093, filed on Apr. 20, 2018, now Pat. No. 10,781,485, which is a
(Continued)

(51) Int. Cl.
C12Q 1/68 (2018.01)
C12Q 1/6874 (2018.01)
(Continued)

(52) U.S. Cl.
CPC ......... *C12Q 1/6874* (2013.01); *C12Q 1/6827* (2013.01); *C12Q 1/6869* (2013.01);
(Continued)

(58) Field of Classification Search
CPC ...................................... C12Q 1/68
(Continued)

(56) References Cited

U.S. PATENT DOCUMENTS 5,629,147 A 5/1997 Asgari et al.
8,071,395 B2 12/2011 Davis et al.
(Continued)

FOREIGN PATENT DOCUMENTS

EP 3169803 B1 11/2019
WO WO 2011/091046 A1 7/2011
(Continued)

OTHER PUBLICATIONS

U.S. Office Action, dated Feb. 13, 2017, issued in U.S. Appl. No. 14/802,936.
(Continued)

*Primary Examiner* — Aaron A Priest
(74) *Attorney, Agent, or Firm* — Weaver Austin Villeneuve & Sampson LLP

(57) ABSTRACT

Disclosed are methods for determining at least one sequence of interest of a fetus of a pregnant mother. In various embodiments, the method can determine one or more sequences of interest in a test sample that comprises a mixture of fetal cellular DNA and mother-and-fetus cfDNA. In some embodiments, methods are provided for determining whether the fetus has a genetic disease. In some embodiments, methods are provided for determining whether the fetus is homozygous in a disease causing allele when the mother is heterozygous of the same allele. In some embodiments, methods are provided for determining whether the fetus has a copy number variation (CNV) or a non-CNV genetic sequence anomaly.

24 Claims, 20 Drawing Sheets

Related U.S. Application Data division of application No. 14/802,873, filed on Jul. 17, 2015, now Pat. No. 9,982,295.

(60) Provisional application No. 62/026,548, filed on Jul. 18, 2014.

(51) Int. Cl.
| | |
|---|---|
| C12Q 1/6869 | (2018.01) |
| G16B 25/00 | (2019.01) |
| G16B 30/00 | (2019.01) |
| C12Q 1/6827 | (2018.01) |
| G16B 30/10 | (2019.01) |

(52) U.S. Cl.
CPC ............. *G16B 25/00* (2019.02); *G16B 30/00* (2019.02); *G16B 30/10* (2019.02)

(58) Field of Classification Search
USPC ........................................................ 435/6.12
See application file for complete search history.

(56) References Cited

U.S. PATENT DOCUMENTS

| | | | |
|---|---|---|---|
| 8,137,912 B2 | 3/2012 | Kapur et al. | |
| 9,163,282 B2* | 10/2015 | Rabinowitz .......... | C12Q 1/6874 |
| 9,982,295 B2 | 5/2018 | Talasaz et al. | |
| 10,119,167 B2 | 11/2018 | Srinivasan et al. | |
| 10,781,485 B2 | 9/2020 | Talasaz et al. | |
| 10,837,055 B2 | 11/2020 | Srinivasan et al. | |
| 2011/0105353 A1 | 5/2011 | Lo et al. | |
| 2011/0230358 A1 | 9/2011 | Rava | |
| 2011/0288780 A1 | 11/2011 | Rabinowitz et al. | |
| 2012/0270212 A1 | 10/2012 | Rabinowitz et al. | |
| 2013/0122492 A1 | 5/2013 | Khosravi et al. | |
| 2013/0189688 A1* | 7/2013 | Shoemaker .......... | C12Q 1/6883 435/6.11 |
| 2013/0196862 A1 | 8/2013 | Rabinowitz et al. | |
| 2013/0261004 A1* | 10/2013 | Ryan .................... | C12Q 1/6869 506/2 |
| 2013/0267425 A1 | 10/2013 | Liao et al. | |
| 2013/0316347 A1 | 11/2013 | Brechot et al. | |
| 2014/0093873 A1 | 4/2014 | Tynan et al. | |
| 2014/0100126 A1 | 4/2014 | Rabinowitz | |
| 2014/0162269 A1* | 6/2014 | Rabinowitz ............ | G16B 20/00 435/6.11 |
| 2014/0194324 A1 | 7/2014 | Gormley et al. | |
| 2014/0243224 A1 | 8/2014 | Barnard et al. | |
| 2014/0274746 A1 | 9/2014 | Khurana et al. | |
| 2015/0051087 A1* | 2/2015 | Rabinowitz .......... | C12Q 1/6869 506/2 |
| 2015/0218631 A1* | 8/2015 | Chuu ................... | C12Q 1/6883 506/26 |
| 2016/0017412 A1 | 1/2016 | Srinivasan et al. | |
| 2016/0186253 A1 | 6/2016 | Talasaz et al. | |
| 2018/0237852 A1 | 8/2018 | Talasaz et al. | |
| 2019/0062832 A1 | 2/2019 | Srinivasan et al. | |
| 2021/0108265 A1 | 4/2021 | Srinivasan et al. | |

FOREIGN PATENT DOCUMENTS

| | | |
|---|---|---|
| WO | WO 2012/037881 A1 | 3/2012 |
| WO | WO 2012/088348 A2 | 6/2012 |
| WO | WO 2016/011414 A1 | 1/2016 |

OTHER PUBLICATIONS

U.S. Final Office Action, dated Jun. 7, 2017, issued in U.S. Appl. No. 14/802,936.
U.S. Office Action, dated Dec. 1, 2017, issued in U.S. Appl. No. 14/802,936.
U.S. Notice of Allowance, dated May 9, 2018, issued in U.S. Appl. No. 14/802,936.
U.S. Notice of Allowance, dated Jul. 8, 2020, issued in U.S. Appl. No. 16/100,102.
U.S. Office Action, dated Jul. 19, 2017, issued in U.S. Appl. No. 14/802,873.
U.S. Final Office Action, dated Nov. 3, 2017, issued in U.S. Appl. No. 14/802,873.
U.S. Notice of Allowance, dated Jan. 23, 2018, issued in U.S. Appl. No. 14/802,873.
U.S. Notice of Allowance, dated May 20, 2020, issued in U.S. Appl. No. 15/959,093.
PCT International Search Report and Written Opinion, dated Oct. 12, 2015, issued in PCT/US2015/041008.
PCT International Preliminary Report on Patentability and Written Opinion, dated Feb. 2, 2017, issued in PCT/US2015/041008.
European First Office Action dated Mar. 29, 2018 issued in Application No. EP 15745053.7.
European Extended Search Report dated Apr. 2, 2020 issued in Application No. EP 19202922.1.
Canadian Office Action dated Mar. 28, 2018 issued in Application No. CA 2,955,367.
Canadian Second Office Action dated Oct. 4, 2019 issued in Application No. CA 2,955,367.
Bentley et al. (Nov. 6, 2008) "Accurate whole human genome sequencing using reversible terminator chemistry," *Nature* 456:53-59.
Bischoff et al. (2002) "Cell-free fetal DNA and intact fetal cells in maternal blood circulation: implications for first and second trimester non-invasive prenatal diagnosis," *Human Reproduction Update* 8(6):496-500.
Boyer et al. (Jun. 1976) "Enrichment of erythrocytes of fetal origin from adult-fetal blood mixtures via selective hemolysis of adult blood cells: an aid to antenatal diagnosis of hemoglobinopathies," *Blood* 47(6):883-897.
Broude (Jun. 2002) "Stem-loop oligonucleotides: a robust tool for molecular biology and biotechnology," *Trends in Biotechnology* 20(6):249-256.
Chen et al. (2004) "Fetal origin of single nucleated erythroblasts and free DNA in the peripheral blood of pregnant women," *International Journal of Gynecology and Obstetrics.*, 85(1):1-5.
Chiu et al. (Jan. 2011) "Non-invasive prenatal assessment of trisomy 21 by multiplexed maternal plasma DNA sequencing: large scale validity study," *BMJ*, 11:342:c7401).
Collarini et al. (2001) "Comparison of Methods for Erythroblast Selection: Application to Selecting Fetal Erythroblasts From Maternal Blood," *Cytometry* 45:267-276.
Database WPI, Week 201224, Thomson Scientific, London, GB; AN 2012-D72706, NPL reference No. XP002745174, "Group of separated DNA tag useful for constructing DNA tag library for confirming sequence information of single DNA sample or multiple DNA samples, comprises specific nucleotide sequence," 1 page.
Epicentre "Nextera™ DNA Sample Prep Kit (Illumina®-Compatible)," attached, Jun. 2011, 12pp.
Gänshirt et al. (1998) "Enrichment of Fetal Nucleated Red Blood Cells from the Maternal Circulation for Prenatal Diagnosis: Experiences with Triple Density Gradient and MACS Based on More than 600 Cases," *Fetal Diagn Ther* 13:276-286.
Gratacós et al. (2014) "Clinical Perspective of Cell-Free DNA Testing for Fetal Aneuploidies," *Fetal Diagn Ther.*, vol. 35, No. 3, Jun. 12, 2014, pp. 151-155, (doi: 10.1159/000362940).
Jensen et al. (Mar. 2013) "High-Throughput Massively Parallel Sequencing for Fetal Aneuploidy Detection from Maternal Plasma," *PLoS One*, 8(3):e57381, 8pp, (doi: 10.1371/journal.pone.0057381. Epub Mar. 6, 2013).
Jiang et al. (2012) "FetalQuant: deducing fractional fetal DNA concentration from massively parallel sequencing of DNA in maternal plasma," *Bioinformatics*, 28(22):2883-2890 (Epub Sep. 8, 2012).
Kinde et al. (2011) "Detection and quantification of rare mutations with massively parallel sequencing," *PNAS* 108(23):9530-9535.
Liao et al. (2011) "Targeted Massively Parallel Sequencing of Maternal Plasma DNA Permits Efficient and Unbiased Detection of Fetal Alleles," *Clin Chem.*, 57(1):92-101 (Epub Nov. 15, 2010).
Liao et al. (May 2012) "Noninvasive Prenatal Diagnosis of Fetal Trisomy 21 by Allelic Ratio Analysis Using Targeted Massively

(56) References Cited

OTHER PUBLICATIONS

Parallel Sequencing of Maternal Plasma DNA," *PLoS One*, 7(5):e38154, 7pp (Published online May 29, 2012).
"Nextera™ DNA Sample Prep Kit (Illumina-compatible)" *Epicentre Biotechnologies*, Cat. Nos. GA09115, GA091120, GA0911-50, GA0911-96, and GABC0950, 9pp.
Nicolaides et al. (2014) "Prenatal Detection of Fetal Triploidy from Cell-Free DNA Testing in Maternal Blood," *Fetal Diagn Ther.*, 35(3):212-217, (doi: 10.1159/000355655, Epub Oct. 10, 2013), 6pp.
Nicolaides et al. (Jun. 2013) "Validation of targeted sequencing of single-nucleotide polymorphisms for non-invasive prenatal detection of aneuploidy of chromosomes 13, 18, 21, X, and Y," *Prenat Diagn*, 33(6):575-579 (doi: 10.1002/pd.4103, Epub Apr. 24, 2013), 5pp.
Papasavva et al. (Dec. 2013) "Next generation sequencing of SNPs for non-invasive prenatal diagnosis: challenges and feasibility as illustrated by an application to β-thalassaemia," *Eur J Hum Genet.*, 21(12):1403-1410, 8pp (doi: 10.1038/ejhg.2013.47. Epub Apr. 10, 2013).
Pongsritasana et al. (2006) "Isolation of Fetal Nucleated Red Blood Cell from Maternal Blood using Immunomagnetic Beads for Prenatal Diagnosis," *Asian Pacific Journal of Allergy and Immunology* 24:65-71.
Prieto et al. (2002) "Comparison of Different CD71 Monoclonal Antibodies for Enrichment of Fetal Cells from Maternal Blood," *Clin Chem Lab Med* 40(2):126-131.
Rava et al. (Sep. 17, 2013) "Circulating Fetal Cell-Free DNA Fractions Differ in Autosomal Aneuploidies and Monosomy X," *Clinical Chemistry*, 60(1):243-250.
Samango-Sprouse et al. (Jul. 2013) "SNP-based non-invasive prenatal testing detects sex chromosome aneuploidies with high accuracy," *Prenat Diagn.*, 33(7):643-649, 13pp (doi: 10.1002/pd.4159. Epub Jun. 20, 2013).
Sparks et al. (Jan. 2012) "Selective analysis of cell-free DNA in maternal blood for evaluation of fetal trisomy," *Prenat Diagn.*, 32(1):3-9, (doi: 10.1002/pd.2922. Epub Jan. 6, 2012).
Talasaz et al. (2009) "Isolating highly enriched populations of circulating epithelial cells and other rare cells from blood using a magnetic sweeper device," *PNAS* 106(10):3970-3975.
Torricelli et al. (2001) "Isolation of Fetal Cells from the Maternal Circulation: Prospects for the Non-Invasive Prenatal Diagnosis," *Clin Chem Lab Med* 39(6):494-500.
Wachtel et al. (1998) "Charge Flow Separation: Quantification of Nucleated Red Blood Cells in Maternal Blood During Pregnancy," *Prenat. Diagn.* 18:455-463.
Zimmermann et al. (2013) "Unique monoclonal antibodies specifically bind surface structures on human fetal erythroid blood cells," *Experimental Cell Research* 319:2700-2707.
Australian Examination Report No. 1 dated Sep. 8, 2020 issued in Application No. AU 2015289414.
European Extended Search Report dated Nov. 29, 2021 issued in Application No. EP 21187772.5.

\* cited by examiner

| Maternal ID | # Putative cells tested | # SRY+/18S+ cells | # SRY-/18S+ cells | # SRY-/18S- cells | call accuracy (%) | Detection (Y=100%, N=0%) | Fetal Cell Assay (SRY) | Gender cfDNA (SRY) | Fetal Cell Quantification |
|---|---|---|---|---|---|---|---|---|---|
| 546B* | 10 | 0 | 10 | 0 | 100% | 100% | - | F | |
| 548B | 4 | 0 | 4 | 0 | 100% | 100% | - | F | |
| 334B | 4 | 4 | 0 | 0 | 100% | 100% | + | M | 3 CFC/ml |
| 572B | 5 | 5 | 0 | 0 | 100% | 100% | + | M | 10 CFC/ml |
| 506B* | na | na | na | na | na | na | N/A | F | N/A |
| 672B | 11 | 7 | 4 | 0 | 64% | 100% | - | M | 5 CFC/ml |
| 708B | 3 | 0 | 2 | 1 | 0% | 100% | - | F | 0 CFC/ml |
| 738B (Trisomy+) | na | na | na | na | na | na | N/A | F | |
| 765B | 4 | 0 | 4 | 0 | 0% | 100% | - | F | |

Figure 19

NON-INVASIVE PRENATAL DIAGNOSIS OF FETAL GENETIC CONDITION USING CELLULAR DNA AND CELL FREE DNA

CROSS REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

The determination of copy number of genetic sequences in a fetus is of important diagnostic value. For instance, in a dominant genetic disorder, the presence of a single copy of a disease causing allele causes the phenotypical expression of the genetic disorder. In contrast, in a recessive genetic disorder, the presence of a single copy of a disease causing allele only renders the individual a carrier, and does not cause the phenotypical expression of the genetic disorder. In addition, abnormal copy numbers of genetic sequences, e.g., chromosome segments or whole chromosomes in partial or complete aneuploidy, often cause various genetic disorders. For instance, trisomy 21 causes Down Syndrome (DS).

Previously, most information about copy number and copy number variation (CNV) of the fetus was provided by cytogenetic resolution that has permitted recognition of structural abnormalities. Conventional procedures for genetic screening and biological dosimetry have utilized invasive procedures, e.g., amniocentesis, cordocentesis, or chorionic villus sampling (CVS), to obtain fetal cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations. The advent of technologies that allow for sequencing entire genomes in relatively short time, and the discovery of circulating cell-free DNA (cfDNA) including both maternal and fetal DNA in the pregnant mother's blood have provided the opportunity to analyze fetal genetic materials without the risks associated with invasive sampling methods, which provides a tool to diagnose various kinds of copy number variation (CNV) of genetic sequences of interest.

Diagnosis of copy number variation (CNV) in some applications involves heightened technical challenges. When the mother is a carrier for a recessive genetic disease, the fetus has a 25% chance of developing the genetic disease if the father is also a carrier. In such case, the mother is heterozygous of the disease related gene, having one disease causing allele and one normal allele; the fetus is homozygous of the disease related gene, having two copies of the disease causing allele. It is desirable to determine if the fetus has inherited genetic disease-causing mutated alleles from both parents in a non-invasive manner using maternal plasma cfDNA. However, it is difficult to differentiate if the fetus is homozygous or heterozygous when the mother is heterozygous using conventional method of non-invasive prenatal diagnosis (NIPD) because the two scenarios have similar sequence tags mapping to the two alleles for a biallelic gene. Furthermore, some NIPD methods only use polymorphism sequences from homozygous mother and heterozygous fetus to determine fetal zygosity and fetal fraction. Such approach cannot use genetic materials from heterozygous mother to determine fetal zygosity and fetal fraction, therefore limiting the sensitivity and/or efficiency of diagnosis. These challenges underlie the continuing need for noninvasive methods that would reliably diagnose copy number in a variety of clinical settings. Embodiments disclosed herein fulfill some of the above needs and in particular offer an advantage in providing a reliable method that is applicable to the practice of noninvasive prenatal diagnostics.

SUMMARY

In some embodiments, methods are provided for determining the presence, abundance, or copy number of a sequence of interest in the fetus, e.g., a clinically relevant sequence, using fetus-only cellular DNA and cfDNA including maternal and fetal DNA. In some embodiments, methods are provided for determining whether the fetus has a genetic disease, or more specifically, for determining whether the fetus is homozygous in a disease causing allele when the mother is heterozygous of the same allele.

In specific embodiments, the invention provides methods of reliably estimating fetal fraction from polymorphisms such as small base variations or insertions-deletions which are robust with respect to parental ethnicity, embryo sex, gestational age and other environmental factors.

In some embodiments, methods are provided for determining copy number variation (CNV) of partial or complete fetal aneuploidy. CNV that can be determined according to the present method include trisomies and monosomies of any one or more of chromosomes 1-22, X and Y, other chromosomal polysomies, and deletions and/or duplications of segments of any one or more of the chromosomes.

One aspect of the disclosure provides a method for determining at least one sequence of interest of a fetus of a pregnant mother, the method involves: (a) obtaining cellular DNA from the blood of the pregnant mother, where the cellular DNA includes fetal cellular DNA; (b) obtaining mother-and-fetus mixed cfDNA from the blood of the pregnant mother; (c) applying an indicator to at least one of the fetal cellular DNA and the mixed cfDNA, wherein the indicator identifies a source of DNA as being from the fetal cellular DNA or the mixed cfDNA; (d) combining the fetal cellular DNA and the mixed cfDNA to provide a sample of combined cellular DNA and cfDNA; (e) sequencing the sample of combined cellular DNA and cfDNA to provide a plurality of sequence tags; and (f) analyzing the plurality of sequence tags to determine the presence and/or abundance of the at least one sequence of interest in the fetus's DNA, where at least a portion of the plurality of sequence tags map to the at least one sequence of interest.

Implementations may include one or more of the following features. In some implementations, (e) sequencing said sample of combined cellular and cfDNA involves: sequencing said sample of combined cellular and cfDNA to produce a plurality of sequence reads; and aligning the plurality of sequence reads to a reference sequence to provide the plurality of sequence tags, where sources of the plurality of sequence tags are indicated by the indicator identifying the source of DNA.

In some implementations, the fetal cellular DNA is obtained from one or more fetal nucleated red blood cells (NRBCs) in the blood of the pregnant mother. The method further involves separating the fetal NRBCs from maternal erythrocytes in a cellular component of a blood sample of the pregnant mother. In some implementations, separating the fetal NRBCs from the maternal erythrocytes involves differentially lysing maternal erythrocytes.

In some implementations, separating the fetal NRBCs from the maternal erythrocytes includes size-based separation and/or capture-based separation. In some implementations, the capture-based separation involves capturing the fetal NRBCs through binding one or more cellular markers expressed by fetal NRBCs. In some implementations, the one or more cellular markers expressed by fetal NRBCs are selected from the group including CD71, CD36, CD34, antigen-i, galactose, glycophorin-a, fetal haemoglobin, and any combinations thereof. In some implementations, the one or more cellular markers include a surface marker expressed by fetal NRBCs but not, or to a lesser degree, by maternal NRBCs. In some implementations, the one or more cellular markers includes a 4B9-antigen and/or a 4B8-antigen. In some implementations, the capture-based separation involves binding magnetically responsive particles to fetal NRBCs, where the magnetically responsive particles have an affinity to one or more cellular markers expressed by fetal NRBCs. In some implementations, the capture-based separation is performed by an automated immunomagnetic separation device. In some implementations, the capture-based separation involves binding fluorescent labels to fetal NRBCs, where the fluorescent labels have an affinity to one or more cellular markers expressed by fetal NRBCs.

In some implementation, the method further involves: obtaining a blood sample from the pregnant mother. The method may also involve separating an erythrocyte fraction and a plasma fraction of the blood sample. The method may also involve obtaining the fetal cellular DNA from the erythrocyte fraction of the blood sample. The method may also involve obtaining the cfDNA from the plasma fraction of the blood sample. The method further involves preparing a first sequencing library of the fetus-only cellular DNA and a second sequencing library of the cfDNA, where applying the indicator in (c) comprises incorporating indexes in each of said sequencing libraries, wherein the indexes incorporated in said first library differ from the indexes incorporated in said second library, and the indexes are identifiable from said plurality of sequence tags.

In some implementations, incorporating indexes in each of said sequencing libraries involves hybridizing and extending adapter oligonucleotides including the indexes. In some implementations, the adapter oligonucleotides include locus-specific extension oligonucleotides. In some implementations, the locus-specific extension oligonucleotides are selective for two or more alleles of a disease related gene. In some implementations, each of the adapter oligonucleotides includes an adapter sequence or a portion thereof, where the adapter sequence is configured to hybridize to an oligonucleotide attached to a substrate of a flow cell of a sequencing apparatus. In some implementations, incorporating indexes to each of said sequencing libraries involves ligating or transposing sequences including the indexes to the fetal cellular DNA and the mixed cfDNA. The method further involves incorporating an individual-specific index to the sequencing libraries, where the individual-specific index indicates the identity of the pregnant mother, thereby allowing the pregnant mother's DNA to be processed with other individuals' DNA for parallel sequencing. In some implementations, the sequencing libraries are transposon insertion libraries.

In some implementations, the method further involves determining whether the fetus has a genetic disease from the at least one sequence of interest of the fetus. In some implementations, the at least one sequence of interest includes a disease associated allele selected from the group including: a single nucleotide polymorphism, a tandem repeat, a micro-deletion, an insertion, an indel, and any combinations thereof.

In some implementations, the method further involves enriching the sequence of interest using a primer including a locus-specific extension oligonucleotide that hybridizes to two or more alleles of a gene related to the disease. In some implementations, the primer further includes an index sequence. In some implementations, the method further involves enriching the sequence of interest applying two primer sequences bracketing the sequence of interest. In some implementations, the at least one sequence of interest includes a chromosome or a chromosome segment. In some implementations, the method further involves determining a complete or partial aneuploidy.

Another general aspect of the disclosure provides a method, implemented at a computer system that includes one or more processors and system memory, for determining a condition of a fetus related to a sequence of interest. The method involves obtaining, by the computer system, sequence reads of fetus-only cellular DNA obtained from a blood sample of the mother carrying the fetus, the cellular DNA having been specifically enriched for a sequence of interest; computing, by the computer system, a count of sequence tags mapping to the sequence of interest for the cellular DNA; obtaining, by the computer system, sequence reads of mother-and-fetus mixed cfDNA obtained from the mother, the cfDNA having been specifically enriched for the sequence of interest; computing, by the computer system, a count of sequence tags mapping to the sequence of interest for the cfDNA; comparing, by the computer system, the sequence tag counts mapping to the sequence of interest between the cellular DNA and the cfDNA; and determining, by the computer system, the condition of the fetus related to the sequence of interest. In some implementations, the specifically enriched cellular DNA and the specifically enriched cfDNA were combined for amplification and/or sequencing.

Computer program products and systems implementing the methods described above are also provided.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 19 shows the test results of the Y chromosome specific gene sry for 9 samples using fetal cellular DNA and cfDNA.

DETAILED DESCRIPTION

Definitions

Figure 1:
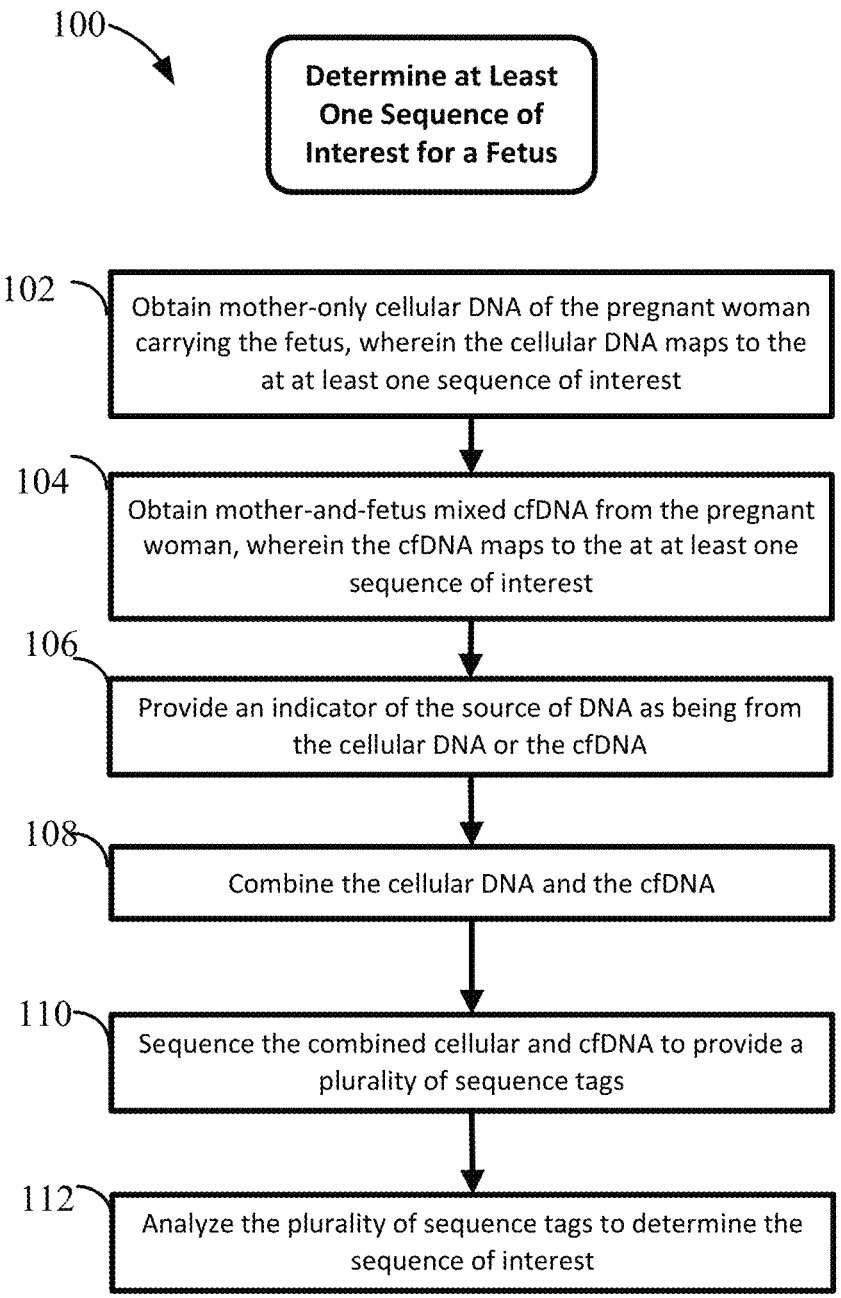
FIG. 1 shows a process of a method for determining a condition of a fetus related to a sequence of interest involving analyses of mother-only cellular DNA.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

"Whole blood sample" herein refers to a whole blood sample that has not been fractionated or separated into its component parts. Whole blood is often combined with an anticoagulant such as EDTA or ACD during the collection process, but is generally otherwise unprocessed. In the US, the capitalized "Whole Blood" means a specific standardized product for transfusion or further processing, where "whole blood" is any unmodified collected blood.

"Blood fractionation" is the process of fractionating whole blood or separating it into its component parts. This is typically done by centrifuging the blood. The resulting components are: (a) a clear solution of blood plasma in the upper phase (which can be separated into its own fractions), (b) a buffy coat, which is a thin layer of leukocytes (white blood cells) mixed with platelets in the middle, and (c) erythrocytes (red blood cells) at the bottom of the centrifuge tube in the hematocrit faction.

Serum separation tubes (SSTs) are tubes used in phlebotomy containing a silicone gel; when centrifuged the silicone gel forms a layer on top of the buffy coat, allowing the blood plasma to be removed more effectively for testing and related purposes.

"Blood plasma" or "plasma" is the straw-colored/pale-yellow liquid component of blood that normally holds the blood cells in whole blood in suspension. It makes up about 55% of total blood by volume. It is the intravascular fluid part of [extracellular fluid] (all body fluid outside of cells). It is mostly water (93% by volume), and contains dissolved proteins including albumins, immunoglobulins, and fibrinogen, glucose, clotting factors, electrolytes (Na+, Ca2+, Mg2+, HCO3− Cl− etc.), hormones and carbon dioxide.

Blood plasma can be prepared by centrifuging a tube of whole blood and containing an anticoagulant until the blood cells fall to the bottom of the tube. The blood plasma is then poured or drawn off. Blood plasma has a density of approximately 1025 kg/m3, or 1.025 kg/l.

"Peripheral blood" is blood that obtained from acral areas, or from the circulation remote from the heart; the blood in the systemic circulation.

"Fixing" is a technique that maintains the structure of cells and/or sub-cellular components such as cell organelles (e.g., nucleus). Fixing modifies the chemical or biological structure cellular components by, e.g., cross-linking them. Fixing may cause whole cells and cellular organelles to resist lysis. Of interest, fixing may also cause cellular nucleic acids to resist release into a surrounding medium. For example, fixing may prevent nuclear DNA from white blood cells to resist release into a plasma fraction during centrifugation of whole blood.

"Fixative" is an agent such as a chemical or biological reagent that fixes cellular nucleic acids and thereby causes cells to resist release of such nucleic acids into a surrounding medium. A fixative may disable cellular proteolytic enzymes and nucleases. Examples of fixatives include aldehydes (e.g., formaldehyde), alcohols, and oxidizing agents. Examples of suitable fixatives are presented in US Patent Application Publication 2010/0184069, filed Jan. 19, 2010, and in US Patent Application Publication No. 2010/209930, filed Feb. 11, 2010, each incorporated herein by reference in its entirety. A vendor of commercially available fixative compositions for fixing nuclei of white blood cells is Streck, Inc. of Omaha Nebr. Streck blood collection tubes such the Streck Cell-free DNA BCT contain a mild preservative, which fixes cellular nuclei and large cellular components, thereby inhibiting white blood cell lysis that can contaminate plasma DNA with cellular DNA.

The term "copy number variation" herein refers to variation in the number of copies of a nucleic acid sequence present in a test sample in comparison with the copy number of the nucleic acid sequence present in a reference sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a sequence of interest in test sample with an expected level of the sequence of interest. For example, the level of the sequence of interest in the test sample is compared to that present in a qualified sample. Copy number variants/variations include deletions, including microdeletions, insertions, including microinsertions, duplications, multiplications, and translocations. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome, e.g., partial monosomy and partial trisomy, and encompasses imbalances resulting from translocations, deletions and insertions.

The term "plurality" refers to more than one element. For example, the term is used herein in reference to a number of nucleic acid molecules or sequence tags that is sufficient to identify significant differences in copy number variations in test samples and qualified samples using the methods disclosed herein. In some embodiments, at least about $3\times10^6$ sequence tags of between about 20 and 40 bp are obtained for each test sample. In some embodiments, each test sample provides data for at least about $5\times10^6$, $8\times10^6$, $10\times10^6$, $15\times10^6$, $20\times10^6$, $30\times10^6$, $40\times10^6$, or $50\times10^6$ sequence tags, each sequence tag comprising between about 20 and 40 bp.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The terms "cell-free DNA" (cfDNA) and "circulating cell-free DNA" are used herein interchangeably to refer to fragments of DNA existing outside of cells in vivo, for example, circulating in maternal blood. The terms can also be used to refer to the fragments of DNA that have been obtained from the in vivo extracellular sources and separated, isolated or otherwise manipulated in vitro. The fragments of cfDNA typically have length ranging about 150-200 bp and averaging about 170 bp, which presumably relates to the length of a DNA stretch wrapped around a nucleosome. The cfDNA circulating in a pregnant woman include DNA fragments from the mother and the fetus or fetuses, with the fetal component ranging up to about 20% in some cases and scenarios, which is referred to as fetal fraction. In many situations, fetal fraction is often less than 20%. Similarly, the terms "cell-free RNA" and "circulating cell-free RNA" are used herein interchangeably to refer to fragments of RNA existing outside of cells in vivo, for example, circulating in maternal blood. Several embodiments of the methods and compositions exemplified herein with regard to cfDNA can be used for cell-free RNA as well.

The terms "cellular DNA," and "cellular genomic DNA," are used interchangeably herein with reference to DNA existing in a cell in vivo and containing a complete genome of the cell or organism. The terms can also be used to refer to DNA that has been obtained from the in vivo cell and separated, isolated or otherwise manipulated in vitro so long as the DNA was not removed from the cell in vivo. Typically, the cell is removed from cfDNA prior to the cell being lysed to produce in vitro cellular DNA. Although cfDNA theoretically may collectively constitute a complete genome, the term gDNA as used herein does not include cfDNA. Similarly, the term "cellular RNA" is used herein to refer to RNA existing in a cell in vivo. Several embodiments of the methods and compositions exemplified herein with regard to cellular DNA can be used for cellular RNA as well.

The term "portion" is used herein in reference to the amount of sequence information of fetal and maternal nucleic acid molecules in a biological sample that in sum amount to less than the sequence information of 1 human genome.

The terms "index," "index sequence," "unique identifier," "barcode," and "barcode sequence" are used interchangeably herein unless specified otherwise. The terms refer to a sequence of nucleotides, usually oligonucleotides, that can be used to identify a sequence of interest. The index sequence may be exogenously incorporated into the sequence of interest by ligation, extension, or other methods known in the art. The index sequence may also be endogenous to the sequence of interest, e.g., a fragment in the sequence of interest itself may be used as an index. For implementations of index sequences, see, Kinde, et al. (2011), Proceedings of the National Academy of Sciences, 108, 9530.

The term "test sample" herein refers to a sample, typically derived from a biological fluid, cell, tissue, organ, or organism, comprising a nucleic acid or a mixture of nucleic acids comprising at least one nucleic acid sequence that is to be screened for copy number variation. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "qualified sample" or "unaffected sample" herein refers to a sample comprising a mixture of nucleic acids that are present in a known copy number to which the nucleic acids in a test sample are to be compared, and it is a sample that is normal, i.e., not aneuploid, for the sequence of interest. In some embodiments, qualified samples are used as unaffected training samples of a training set to derive sequence masks or sequence profiles. In certain embodiments, qualified samples are used for identifying one or more normalizing chromosomes or segments for a chromosome under consideration. For example, qualified samples may be used for identifying a normalizing chromosome for chromosome 21. In such case, the qualified sample is a sample that is not a trisomy 21 sample. Another example involves using only females as qualifying samples for chromosome X. Qualified samples may also be employed for other purposes such as determining thresholds for calling affected samples, identifying thresholds for defining mask regions on a reference sequence, determining expected coverage quantities for different regions of a genome, and the like.

The term "patient sample" herein refers to a biological sample obtained from a patient, i.e., a recipient of medical attention, care or treatment. The patient sample can be any of the samples described herein. In certain embodiments, the patient sample is obtained by non invasive procedures, e.g., peripheral blood sample or a stool sample. The methods described herein need not be limited to humans. Thus, various veterinary applications are contemplated in which case the patient sample may be a sample from a non-human mammal (e.g., a feline, a porcine, an equine, a bovine, and the like).

The term "mixed sample" herein refers to a sample containing a mixture of nucleic acids, which are derived from different genomes.

The term "maternal sample" herein refers to a biological sample obtained from a pregnant subject, e.g., a woman or female of another species that is pregnant.

The term "biological fluid" herein refers to a liquid in or from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "sequence of interest" herein refers to a nucleic acid sequence that is associated with a difference in sequence representation in healthy versus diseased individuals. A sequence of interest can be a sequence on a chromosome that is misrepresented, i.e., over- or under-represented, in a disease or genetic condition. A sequence of interest may be a portion of a chromosome, i.e., chromosome segment, or a whole chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "normalizing sequence" herein refers to a sequence that is used to normalize the number of sequence tags mapped to a sequence of interest associated with the normalizing sequence. In some embodiments, a normalizing sequence comprises a robust chromosome. A "robust chromosome" is one that is unlikely to be aneuploid. In some cases involving the human chromosome, a robust chromosome is any chromosome other than the X chromosome, Y chromosome, chromosome 13, chromosome 18, and chromosome 21. In some embodiments, the normalizing sequence displays a variability in the number of sequence tags that are mapped to it among samples and sequencing runs that approximates the variability of the sequence of interest for which it is used as a normalizing parameter. The normalizing sequence can differentiate an affected sample from one or more unaffected samples. In some implementations, the normalizing sequence best or effectively differentiates, when compared to other potential normalizing sequences such as other chromosomes, an affected sample from one or more unaffected samples. In some embodiments, the variability of the normalizing sequence is calculated as the variability in the chromosome dose for the sequence of interest across samples and sequencing runs. In some embodiments, normalizing sequences are identified in a set of unaffected samples.

A "normalizing chromosome," "normalizing denominator chromosome," or "normalizing chromosome sequence" is an example of a "normalizing sequence." A "normalizing chromosome sequence" can be composed of a single chromosome or of a group of chromosomes. In some embodiments, a normalizing sequence comprises two or more robust chromosomes. In certain embodiments, the robust chromosomes are all autosomal chromosomes other than chromosomes, X, Y, 13, 18, and 21. A "normalizing segment" is another example of a "normalizing sequence." A "normalizing segment sequence" can be composed of a single segment of a chromosome or it can be composed of two or more segments of the same or of different chromosomes. In certain embodiments, a normalizing sequence is intended to normalize for variability such as process-related, interchromosomal (intra-run), and inter-sequencing (inter-run) variability.

The term "variability" herein refers to another characteristic of a normalizing chromosome that enables one to distinguish one or more unaffected, i.e., normal, samples from one or more affected, i.e., aneuploid, samples. The variability of a normalizing chromosome, which is measured in a set of qualified samples, refers to the variability in the number of sequence tags that are mapped to it that approximates the variability in the number of sequence tags that are mapped to a chromosome of interest for which it serves as a normalizing parameter.

The term "sequence tag density" herein refers to the number of sequence reads that are mapped to a reference genome sequence, e.g., the sequence tag density for chromosome 21 is the number of sequence reads generated by the sequencing method that are mapped to chromosome 21 of the reference genome.

The term "sequence tag density ratio" herein refers to the ratio of the number of sequence tags that are mapped to a chromosome of the reference genome, e.g., chromosome 21, to the length of the reference genome chromosome.

The term "sequence dose" herein refers to a parameter that relates the number of sequence tags identified for a sequence of interest and the number of sequence tags identified for the normalizing sequence. In some cases, the sequence dose is the ratio of the sequence tag coverage for a sequence of interest to the sequence tag coverage for a normalizing sequence. In some cases, the sequence dose refers to a parameter that relates the sequence tag density of a sequence of interest to the sequence tag density of a normalizing sequence. A "test sequence dose" is a parameter that relates the sequence tag density of a sequence of interest, e.g., chromosome 21, to that of a normalizing sequence, e.g., chromosome 9, determined in a test sample. Similarly, a "qualified sequence dose" is a parameter that relates the sequence tag density of a sequence of interest to that of a normalizing sequence determined in a qualified sample.

The term "coverage" refers to the abundance of sequence tags mapped to a defined sequence. Coverage can be quantitatively indicated by sequence tag density (or count of sequence tags), sequence tag density ratio, normalized coverage amount, adjusted coverage values, etc.

The term "coverage quantity" is a modification of raw coverage and often represents the relative quantity of sequence tags (sometimes called counts) in a region of a genome such as a bin. A coverage quantity may be obtained by normalizing, adjusting and/or correcting the raw coverage or count for a region of the genome. For example, a normalized coverage quantity for a region may be obtained by dividing the sequence tag count mapped to the region by the total number sequence tags mapped to the entire genome. Normalized coverage quantity allows comparison of coverage of a bin across different samples, which may have different depths of sequencing. It differs from sequence dose in that the latter is typically obtained by dividing by the tag count mapped to a subset of the entire genome. The subset is a normalizing segment or chromosome. Coverage quantities, whether or not normalized, may be corrected for global profile variation from region to region on the genome, G-C fraction variations, outliers in robust chromosomes, etc.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a physical property. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation, e.g., an aneuploidy, in an organism. If a threshold is exceeded by results obtained from methods disclosed herein, a subject can be diagnosed with a copy number variation, e.g., trisomy 21. Appropriate threshold values for the methods described herein can be identified by analyzing normalized values (e.g. chromosome doses, NCVs or NSVs) calculated for a training set of samples. Threshold values can be identified using qualified (i.e., unaffected) samples in a training set which comprises both qualified (i.e., unaffected) samples and affected samples. The samples in the training set known to have chromosomal aneuploidies (i.e., the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may advantageous to use larger sets of qualified samples to improve the diagnostic utility of the threshold values.

The term "read" refers to sequence data from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to provide a limit amount of mismatch in aligning to a reference genome. In some embodiments, tags that can be mapped to more than one location on a reference genome, i.e., tags that do not map uniquely, may not be included in the analysis.

The term "site" refers to a unique position (i.e. chromosome ID, chromosome position and orientation) on a reference genome. In some embodiments, a site may be a residue, a sequence tag, or a segment's position on a sequence. The term "locus" may be used to refer to the specific location of a nucleic acid sequence or polymorphism on a reference chromosome.

Normalized chromosome value (NCV) relates coverage of a test sample to coverages of a set of training/qualified samples. In some embodiments, NCV is based on chromosome dose. In some embodiments, NCV relates to the difference between the chromosome dose of a chromosome of interest in a test sample and the mean of the corresponding chromosome dose in a set of qualified samples as, and can be calculated as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome ratio (dose) for test sample i.

In some embodiments, NCV can be calculated "on the fly" by relating the chromosome dose of a chromosome of interest in a test sample to the median of the corresponding chromosome dose in multiplexed samples seauenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_i$ is the observed j-th chromosome dose for test sample i. In this embodiment, test sample i is one of the multiplexed samples sequenced on the same flow cell from which $M_j$ is determined.

For example, for chromosome of interest 21 in test sample A, which is sequenced as one of 64 multiplexed samples on one flow cell, the NCV for chromosome 21 in test sample A is calculated as the dose of chromosome 21 in sample A minus the median of the dose for chromosome 21 determined in the 64 multiplexed samples, divided by the standard deviation of the dose for chromosome 21 determined for the 64 multiplexed samples on flow cell 1, or of additional flow cells e.g. 20.

As used herein, the terms "aligned," "alignment," or "aligning" refer to the process of comparing a read or tag to a reference sequence and thereby determining whether the reference sequence contains the read sequence or tag sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about 105 times larger, or at least about 106 times larger, or at least about 107 times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In various embodiments, the reference sequence is a consensus sequence or other combination derived from multiple individuals. However, in certain applications, the reference sequence may be taken from a particular individual.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein, the term "fetal fraction" refers to the fraction of fetal nucleic acids present in a sample comprising fetal and maternal nucleic acid. Fetal fraction is often used to characterize the cfDNA in a mother's blood.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

The term "complete" when used in reference to a chromosomal aneuploidy herein refers to a gain or loss of an entire chromosome.

The term "partial" when used in reference to a chromosomal aneuploidy herein refers to a gain or loss of a portion, i.e., segment, of a chromosome.

The term "mosaic" herein refers to denote the presence of two populations of cells with different karyotypes in one individual who has developed from a single fertilized egg. Mosaicism may result from a mutation during development which is propagated to only a subset of the adult cells.

The term "non-mosaic" herein refers to an organism, e.g., a human fetus, composed of cells of one karyotype.

The term "sensitivity" as used herein is equal to the number of true positives divided by the sum of true positives and false negatives.

The term "specificity" as used herein is equal to the number of true negatives divided by the sum of true negatives and false positives.

The term "enrich" herein refers to the process of separating or selectively amplifying a subset of nucleic acids contained in a sample. Enrichment includes specific enrichment that targets specific sequences, e.g., polymorphic sequences, and non-specific enrichment that amplifies the whole genome of the DNA fragments of the sample.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

The term "polymorphism" or "genetic polymorphism" is used herein in reference to the occurrence in the same population of two or more alleles at one genetic locus. Various forms of polymorphism include single nucleotide polymorphisms, tandem repeats, micro-deletions, insertions, indels, and other polymorphisms.

The term "training set" and "training sequences" are used interchangeably herein and refer to a set of genetic sequences obtained to derive quantitative estimates for one or more sequences of interest. Examples of the estimates derivable include the probability distribution of quantities or properties of the sequences of interest (e.g., mean and standard deviation of allele counts or sequence coverage), relations among sequences of interest (e.g., differences of coverages).

Introduction

In various embodiments, the method can determine one or more sequences of interest in a test sample that comprises a mixture of single-genome cellular DNA and mother-and-fetus cfDNA. In some embodiments, the single-genome cellular DNA is maternal DNA; in other embodiments, the single-genome cellular DNA is fetus DNA. In particular embodiments, single-genome cellular nucleic acid material (e.g. genomic DNA) is obtained from fetal cells that are isolated from the blood of a pregnant female, and also mother-and-fetus cell free nucleic acid material (e.g. genomic cfDNA) is obtained from blood of the same female. Typically, fetal cells are in relatively low abundance in maternal blood, such that relatively low quantities of fetal nucleic acids are available from the amount of blood that is comfortably drawn from a pregnant mother. However, fetal cells provide a convenient 'package' for separating fetal nucleic acids from the relatively high background of maternal nucleic acid that is found in the blood of a pregnant female. Conversely, relatively large amounts of cell-free fetal nucleic acid can be obtained from a standard blood draw, albeit along with a relatively high background of maternal nucleic acid material. The present disclosure provides methods and compositions that exploit the relatively high yield of fetal nucleic acids obtained from cell-free fractions and the relatively pure fetal nucleic acid obtained from fetal cells to provide a combined method with emergent benefits that are greater than the benefits provided by the methods when carried out individually. By way of more specific example, nucleic acids, once obtained from cellular and cell-free fractions, respectively, can be re-combined for analytical steps in a method set forth herein, The relatively abundant nucleic acids in the mixed mother-and-fetus fraction can be detected robustly and with high technical/statistical confidence in this combined analytical process and the relatively pure fetal nucleic acid can be used as an internal reference to distinguish characteristics of the fetal nucleic acid that may otherwise have been difficult to distinguish in the mixed mother-and-fetus fraction.

Methods, apparatus, and systems are disclosed herein for determining at least one sequence of interest of a fetus of a pregnant mother. In some embodiments involving analyses of mother-only cellular DNA, the disclosed embodiments permit determining the zygosity case (e.g., homozygous in a minor allele) of fetal DNA obtained from cfDNA. In some embodiments, the method can determine one or more sequences of interest in a test sample that contains a mixture of mother-only cellular DNA and mother-and-fetus cfDNA. The sequences of interest determined by the methods and apparatus disclosed herein may include one or more of the following: single nucleotide polymorphisms, tandem repeats, micro-deletions, insertions, and other polymorphisms. In some embodiments, the method may determine copy number of sequence of interests, including gains or losses of entire chromosomes, alterations involving very large chromosomal segments that are microscopically visible, and an abundance of sub-microscopic copy number variation of DNA segments ranging from single nucleotide, to kilobases (kb), to megabases (Mb) in size.

In some embodiments, methods are provided for determining whether the fetus has a genetic condition, or more specifically, for determining whether the fetus is homozygous in a disease causing allele when the mother is heterozygous of the same allele. When the mother is a carrier for a recessive genetic condition, the fetus has a 25% chance of developing the genetic condition if the father is also a carrier. In such case, the mother is heterozygous of the gene for the condition, having one causative allele and one normal allele; the fetus is homozygous of the gene, having two copies of the causative allele. It is desirable to determine if the fetus has inherited particular alleles (e.g. disease causing alleles) from both parents and to do so in a non-invasive manner using maternal plasma cfDNA. However, it is difficult to differentiate if the fetus is homozygous or heterozygous when the mother is heterozygous using conventional method of non-invasive prenatal diagnosis (NIPD) because only those SNPs for which the mother is homozygous and the fetus is heterozygous were considered "informative SNPs." SNPs where the mother may be heterozygous and the fetus is homozygous cannot be used without understanding the inherent "noise" in the heterozygous calls for the mother.

By genotyping mother-only DNA, the current disclosure provides methods to use the majority component of genetic materials that contributes to the data from the mixed genome cfDNA. One can then evaluate multiple SNPs or other polymorphisms from the maternal cellular DNA to assist the zygosity call for a polymorphism of interest. This may be done with or without explicitly determining the fetal fraction in the cfDNA.

Processing Workflow Involving Analyses of Mother-only Cellular DNA

To detect if a fetus of a carrier mother will manifest a recessive genetic trait, one can determine if the fetus is homozygous for the disease-causing alleles in a background where the mother is heterozygous. In some embodiments, one takes advantage of the fact that, in maternal blood, mother-only cellular DNA can be obtained from the white blood cells of the buffy coat and the mother-and-fetus mixed cfDNA can be obtained from the plasma. Information from the mother-only cellular DNA can be used to reduce the noise in the data, thereby helping to differentiate the homozygous fetus case from heterozygous fetus case (when mother is heterozygous). In some embodiments, a targeted amplification and sequencing method can be used for this purpose. To reduce processing biases and otherwise permit reliable comparison of the cfDNA sequences and the cellular DNA sequences, the two DNA sources are processed similarly; for example, they are amplified and/or sequenced by multiplexing. In some embodiments, the cellular DNA and cfDNA are obtained from the same sample but then separated and indexed (or otherwise uniquely identified) and then pooled for locus specific amplification, sequencing, and the like. In some implementations, the separately indexed cellular DNA and cfDNA are made similar with regard to size and concentration prior to pooling for multiplexed amplification, sequencing, and other downstream processing. It will be understood that the methods exemplified herein for use with DNA can use other nucleic acids such as mRNA.

FIG. 1 shows a process flow of a method 100 for determining a sequence of interest of a fetus. In some embodiments, the method 100 involves obtaining mother-only cellular DNA of the pregnant mother (e.g. from isolated maternal cells). See block 102. The mother-only cellular DNA includes at least a sequence that maps to the sequence of interest. In some embodiments, the sequence of interest includes polymorphic sequences of a disease related gene. In some embodiments, the sequence of interest comprises a site of an allele associated with a disease. In some embodiments, the sequence of interest comprises one or more of the following: single nucleotide polymorphism, tandem repeat, micro-deletion, and insertion.

In some embodiments, the cellular DNA is obtained from the white blood cells fractionated into the buffy coat of a blood sample from the pregnant mother. The cellular DNA may also be obtained from cells that are lysed after removal from other tissues and fluid as described hereinafter.

In some embodiments, the method also involves obtaining mother-and-fetus mixed cfDNA from the pregnant mother. See block 104. The cfDNA includes at least one sequence that maps to the at least one sequence of interest. In some embodiments, the cfDNA is obtained from the plasma of a blood sample from the mother. In some embodiments, the blood sample also provides the buffy coat as the source of the cellular DNA.

In some embodiments, the method employs an indicator of the source of DNA as being from the mother-only cellular DNA or from the cfDNA. See block 106. In some embodiments, this indicator is provided by preparing a first sequencing library of the mother-only cellular DNA and a second sequencing library of the cfDNA. In preparing sequence libraries, the method may involve incorporating indexes to one or both of said sequencing libraries. When indexes are incorporated into both libraries, the indexes incorporated to the first library will differ from the indexes incorporated to the second library. Typically the indexes contain unique sequences (e.g., bar codes) that are identifiable in downstream sequencing steps, thereby providing an indicator of the source of the nucleic acids.

In some embodiments, the method proceeds by combining at least a portion of the mother-only cellular DNA and a least a portion of the cfDNA to provide a sample of combined cellular DNA and cfDNA. See block 108. In some embodiments, the cellular DNA and cfDNA are of similar quantity and/or concentration. However, the methods can accommodate a relative skew in quantity, for example where the amount of cellular DNA is less than the amount of cfDNA. In some embodiments, the method involves further processing the combined sample to prepare or modify sequencing libraries. In some embodiments, this involves incorporating sequencing adaptors (e.g., paired end primers) for massively parallel sequencing.

In some embodiments, the method then proceeds with sequencing at least a portion of the sample of combined cellular and cfDNA to provide a plurality of sequence reads. See block 110. The sequence reads are then mapped to a reference sequence containing the sequence of interest or compared to the sequence of interest, thereby providing sequence tags mapped to the sequence of interest. The sequence of interest may identify the presence of an allele. In many embodiments, the sample has been selectively enriched for the sequence of interest.

In some embodiments, the sample has not been selectively enriched for the sequence of interest before sequencing, wherein the sample may be amplified by whole genome amplification. In these embodiments, the sequence reads are aligned to a reference genome comprising a sequence of interest (e.g., chromosome, chromosome segment) that are typically longer than in the embodiment with selective enrichment targeting shorter sequences of interest (e.g., SNPs, STRs, and sequences of up to kb in size). The sequence reads mapping to the sequence of interest provide sequence tags for the sequence of interest, which can be used to determine a genetic condition related to the sequence of interest.

In some embodiments, the method applies massively parallel sequencing. Various sequencing techniques may be used, including but not limited to, sequencing by synthesis and sequencing by ligation. In some embodiments, sequencing by synthesis uses reversible dye terminators. In some embodiments, single molecule sequencing is used.

In some embodiments, the method further involves analyzing a plurality of sequence tags to determine at least one sequence of interest. See block 112. At least a portion of the plurality of sequence tags map to the at least one sequence of interest. In some embodiments, the method determines the presence or abundance of sequence tags mapping to the sequence of interest. Particularly, the method may determine the relative amounts of two alleles in each of the cfDNA and cellular DNA. In some embodiments, the method may detect that the fetus has a genetic disorder by determining that the fetus is homozygous of a disease causing allele of a disease related gene wherein the mother is heterozygous of the allele. In some embodiments, the at least one sequence of interest comprises a site of an allele associated with a disease. In some embodiments, the method further includes determining if the fetus is homozygous or heterozygous for the disease associated allele.

In some embodiments, the method starts with cellular DNA and cfDNA in separate reaction environments, e.g., test tubes. The method involves enriching wild-type and mutant regions using probes that target both alleles of disease related gene(s) and have different indices for cellular DNA and cfDNA, the indices are incorporated into the targeted sequences in the separate reaction environment. The method further involves mixing the cellular DNA and cfDNA with enriched targeted regions and amplifying the DNA using universal PCR primers. The amplified product will be sequencing-ready targeted libraries of both cellular DNA for the mother and cfDNA for the mother and fetus. The sequencing results may then be used to determine a sequence of interest for the fetus. The method may determine the zygosity of the fetus and/or fetal fraction of the cfDNA.

In some embodiments, the method further involves determining the sequence of interest from the cfDNA and the cellular DNA. It also involves determining at least one or a plurality of training sequence from the cfDNA and the cellular DNA. The training sequences may be any sequences with ascertainable zygosity, such as sequences in the sex chromosomes or other sequences having polymorphisms whose zygosity cases correlate with observable phenotypes. Some embodiments further determine a zygosity case of the sequence of interest for the fetus. In some embodiments, the zygosity case is determined by comparing the relative amounts of two alleles in the cellular DNA and cfDNA mapping to the sequence of interest and mapping to training sequences. In some embodiments, the zygosity case for the fetus is determined by comparing the relative amounts of DNA mapping to two or more alleles.

Figure 2:
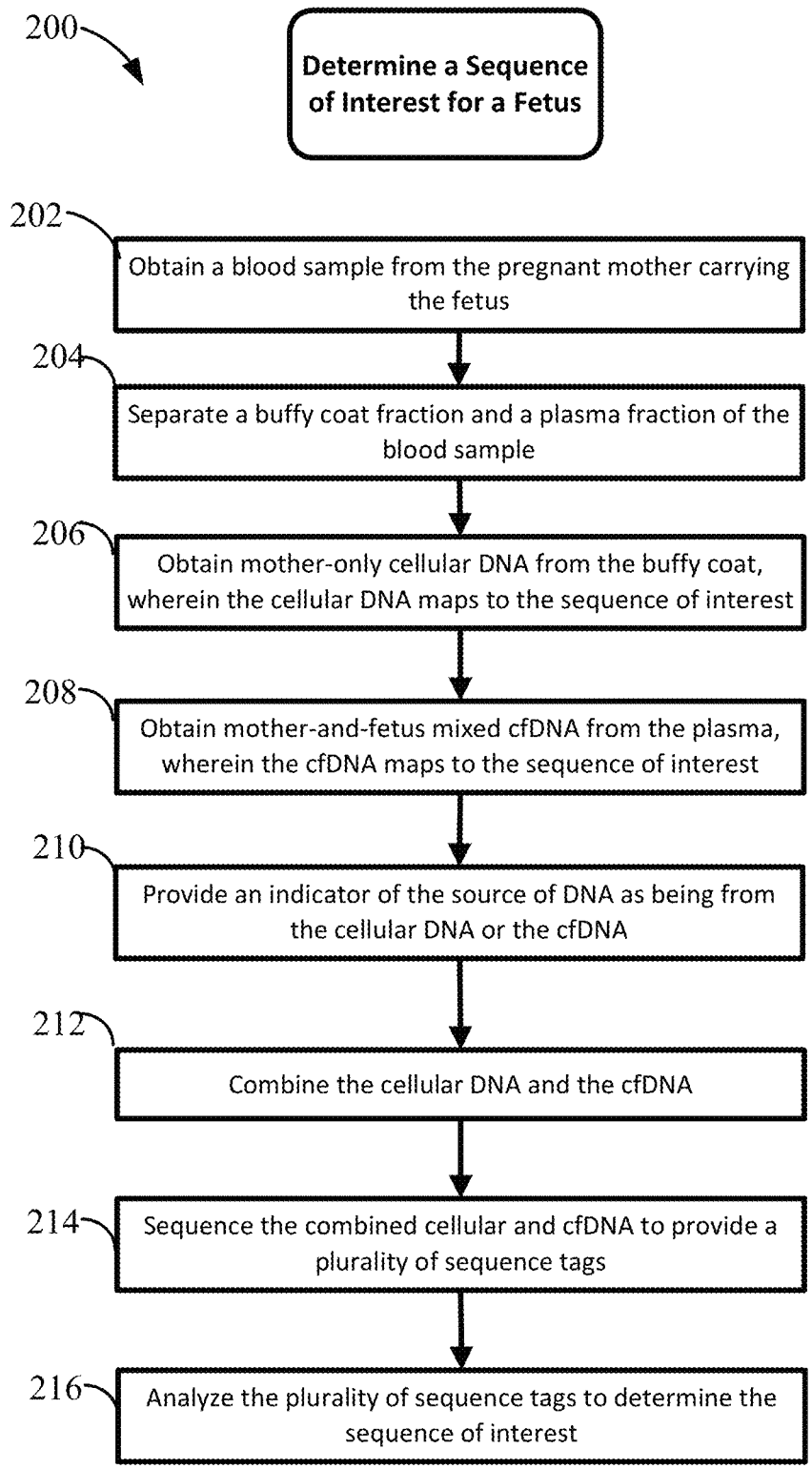
FIG. 2 shows a process of a method for determining conditions related to a sequence of interest for a fetus using a blood sample from the pregnant mother including mother-only cellular DNA.

FIG. 2 shows a workflow of a method for determining conditions related to a sequence of interest for a fetus as in some embodiments of the disclosure. The method involves obtaining a blood sample from the pregnant mother carrying the fetus. See block 202. In some embodiments, it is assumed that the mother is the genetic mother of the fetus. This assumption determines the possible zygosity cases of the fetus given the zygosity of the mother. For instance, if the mother is homozygous of allele a (i.e., a/A) for a biallelic gene having allele a and allele A, the genetic fetus of the mother can only be homozygous a/a, or heterozygous a/A. But for a homozygous (a/a) surrogate mother who is not the genetic mother of the fetus, the fetus may be homozygous a/a, A/A, or heterozygous a/A. The analysis of described herein elsewhere can change its zygosity assumption depending on whether or not the mother is the genetic mother of the fetus.

In some embodiments, the method separates a buffy coat component and a plasma component of the blood sample. See block 204. Separation may be accomplished by fractionation, centrifugation, etc. as described hereinafter. In some embodiments, the method involves obtaining mother-only cellular DNA from the buffy coat. The cellular DNA maps to the sequence of interest. See block 206. In some embodiments, the method also involves obtaining mother-and-fetus mixed cfDNA from the plasma, where the cfDNA maps to the sequence of interest. See block 208. In some embodiments, the method provides an indicator of the source of DNA as being from the cellular DNA or the cfDNA. See block 210. In some embodiments, the indicator is provided by two or more different index sequences for the cellular DNA or the cfDNA. In some embodiments, the method involves combining the cellular DNA and the cfDNA. See block 212. Then the method involves sequencing the combined cellular and cfDNA to provide a plurality of sequence tags. See block 214. In some embodiments, the method involves analyzing the plurality of sequence tags to determine the sequence of interest. See block 216.

Example Workflow using Two Primers when Incorporating Indexes

Plasma cfDNA from a pregnant woman is a mixture comprised mostly of mother DNA with a certain fraction of fetal DNA. An accurate and precise determination of the % fetal DNA in maternal plasma cfDNA is desirable in non-invasive prenatal testing, especially for samples with low fetal fractions. One commonly used method for determining fetal fraction interrogates a plurality of high heterozygocity SNPs and studies allelic frequency differences between mother and fetus. Data analysis can be challenging when one studies SNPs only in mixed maternal plasma cfDNA, since "true" genotype of the mother alone or the fetus alone is not known.

In NIPD, it is difficult to get pure fetal DNA. However, determination of fetal fraction in maternal plasma cfDNA samples can be simplified if one is able to account for known mother-only SNP allelic frequencies from the mixture, since the mother DNA constitutes the majority of the cfDNA. Mother-only cellular DNA can be obtained from the buffy coat of the patient blood sample. In order to correctly account for the mother-only SNP data from the mixed plasma cfDNA SNP data, the biochemical steps to which the two DNAs (buffy coat and plasma) are subjected can be carried out together in the same processing system(s) at the same time, to reduce the risk of introducing process bias.

Figure 3:
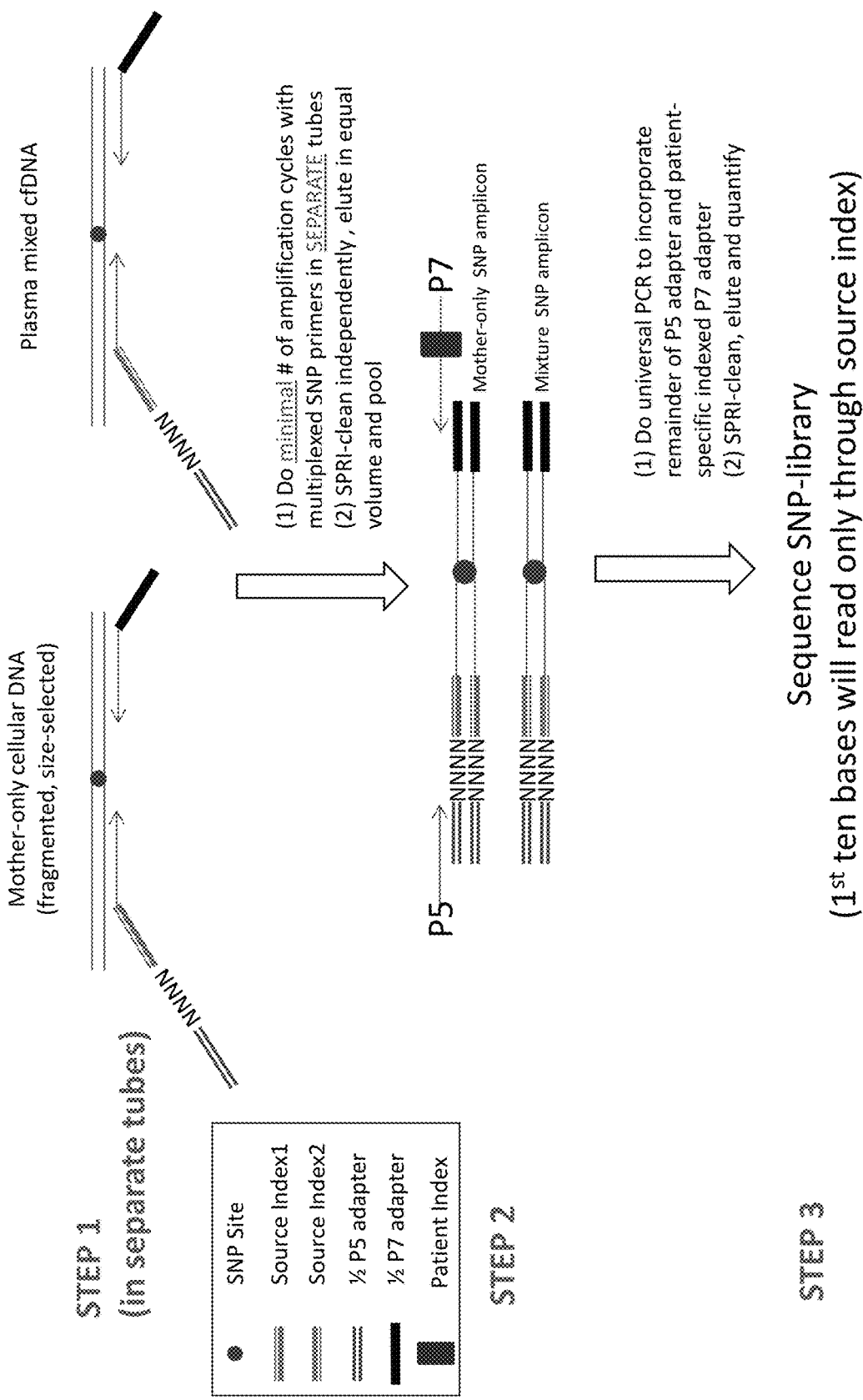
FIG. 3 shows a diagram of a workflow according to some embodiments involving analyses of mother-only cellular DNA, wherein the incorporation of index sequences uses two primers to introduce two adaptor segments.

FIG. 3 shows a diagram of a workflow according to some embodiments of the invention, wherein the incorporation of index sequences occur with two primers introducing two adaptor segments. The figure presents a workflow where the mother and the plasma mixture DNAs are indexed independently during an early PCR step that also interrogates a plurality of SNP-sites in a multiplexed manner. The indexing at this stage is called "source index" since it differentiates between mother-only DNA (e.g. maternal cellular DNA) and the mixed maternal-fetal cfDNA within the same patient sample.

As shown in FIG. 3, the source index 1 sequence is incorporated into the mother-only cellular DNA, and the source index 2 is incorporated into the cfDNA, when the cellular DNA and the cfDNA are processed separately. In this indexing stage, two primers are applied, both targeting the SNP of interest, which is shown as a dot at the center of the two sequences. The primers to the left of the SNP include a sequence index as well as about one half of a paired end adaptor (e.g., the P5 adaptor for the Illumina sequencing platform). Only about half of a sequencing adaptor is introduced by the primer to avoid a long overhang, which could dehybridize too easily in some conditions. The remaining portion of the adaptor is introduced at later processing stages. The primers to the right of the SNP in the depicted example include about one half of second paired end adaptor (e.g., a P7 adaptor for the Illumina sequencing platform). The P5 and P7 adaptors allow library fragments to anneal to their complementary oligos on the flowcell surface of the Illumina sequencer, which adaptors facilitate performance of bridge amplification (e.g. clustering).

One point to consider at the indexing stage is to keep the number of amplification cycles minimal, so as to minimize bias between the two samples. In the depicted workflow, amplicons are independently cleaned using Solid Phase Reversible Immobilization (SPRI), then eluted in equal volume and pooled. The amplicons are then mixed together and subjected to universal PCR at the same time in a single tube. The universal PCR introduces a second index at the P7 end, which second index can be used to multiplex patient samples during sequencing. During the universal PCR, P5 and P7 adaptors are extended to full length. By the end of PCR, library fragments are prepared to include all sequences necessary for multiplexed sequencing. Library fragments are SPRI-cleaned and ready for sequencing.

Since each kind of DNA from the same patient sample is source-indexed uniquely, the downstream data from a given patient can be identified as arising from mother-only DNA (e.g. maternal cellular DNA) and from mixed mother-fetus DNA (e.g. cfDNA). The mother data can then be subtracted from the mixed DNA data. The resulting data provides a means to determine the zygosity and the fetal fraction of the SNPs of interest, which means is associated with lower noise and higher discrimination power between different zygosity cases.

In some prior methods, only those SNPs for which the mother is homozygous and the fetus is heterozygous constitute "informative SNPs." SNPs where the mother may be heterozygous and the fetus is homozygous are not easily used without understanding the inherent "noise" in the heterozygous calls for the mother. By genotyping mother-only DNA, the majority component of that contributes to the data from the mixed plasma cfDNA is now known using the method of the current disclosure. One can then use all SNPs where there is a difference between mother and fetus to calculate fetal fraction.

It will be understood, that biochemical steps and analytical steps exemplified above for processing maternal only DNA with mixed maternal-fetal DNA from a patient sample can be similarly carried out using fetal only DNA (e.g. fetal cellular DNA) with the mixed maternal-fetal DNA. For example, the method can include a step of isolating fetal cells from maternal blood using, for example, antibodies to fetal cell surface antigens. The antibodies can be attached to solid phase to allow separation and/or the antibodies can be used to detect fetal cells separated using known cell isolation techniques. Exemplary techniques that can be used to isolate fetal cells from maternal blood are set forth in U.S. Pat. Nos. 8,071,395 and 8,168,389, each of which is incorporated herein by reference. The methods can also be carried out with nucleic acids other than DNA, for example, mRNA.

Example Workflow using One Primer when Incorporating Indexes

Figure 4:
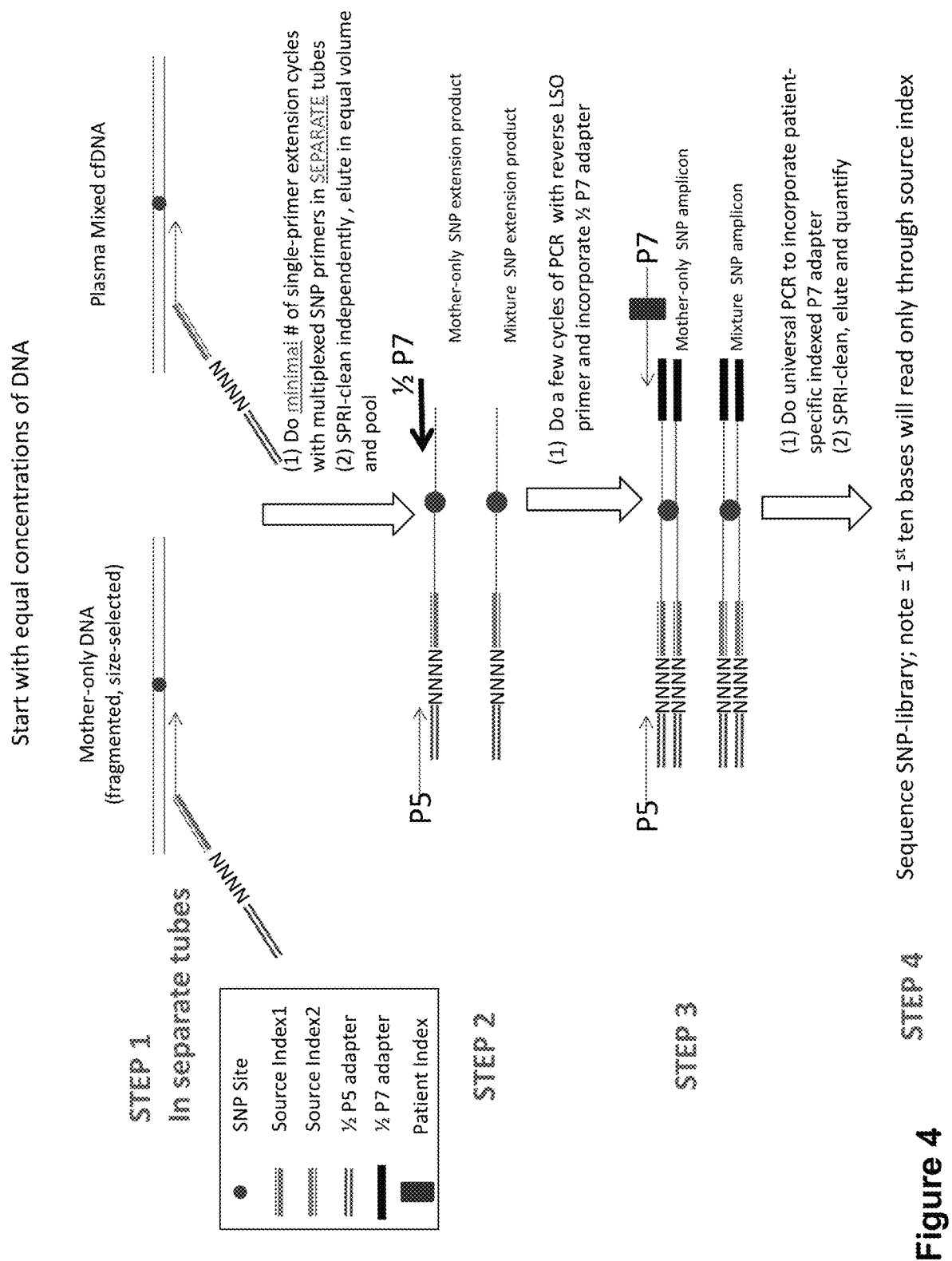
FIG. 4 shows a workflow that uses only one primer when incorporating indexes, and introduces only one sequencing adaptor (P5) instead of two adaptors.

FIG. 4 presents a workflow similar to that of example 2, but it uses only one primer and introduces only one sequencing adaptor (P5) when incorporating indexes. The workflow introduces a second adaptor (P7) after two samples have been indexed and combined. The mother DNA and the plasma mixture DNA are indexed independently with a "source-index" at a first step extension. A single-primer based cyclic extension reaction is done in two separate tubes using multiplexed locus-specific extension oligos (F-LSO) which introduce the source-index and ½ of the P5 adapter. A separate locus-specific extension oligo is used for each SNP (training and otherwise) under consideration. After a relatively small number single extension cycles, the samples are pooled and subjected to PCR with the reverse LSO (R-LSO) which also introduces ½ of the P7 adapter and the remainder of the P5 adapter. A final universal PCR introduces all of the necessary sequencing adapters along with a patient-specific index at the P7 end. The workflow is otherwise comparable to that of Example 2. Again, the methods can be carried out using fetal-only DNA instead of maternal-only DNA. Alternatively or additionally, other nucleic acids, such as mRNA can be used.

Example Workflow using Ligation to Incorporate Index

Figure 5A:
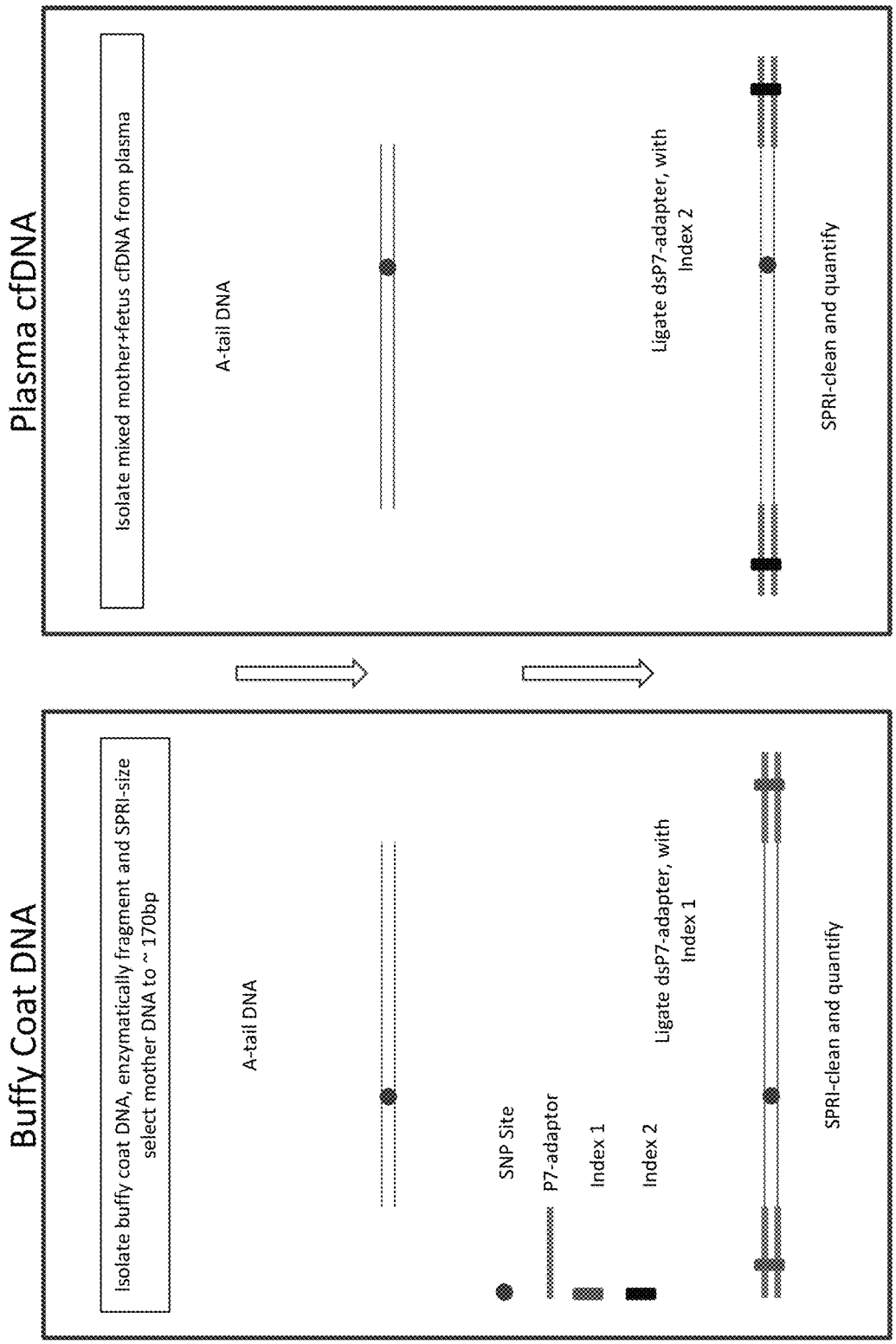
FIGS. 5A and 5B describe a workflow where the mother-only cellular DNA and mixture cfDNA are indexed independently, mixed together, and then subjected to the multiplexed SNP-interrogation at the same time in a single tube.
Figure 5B:
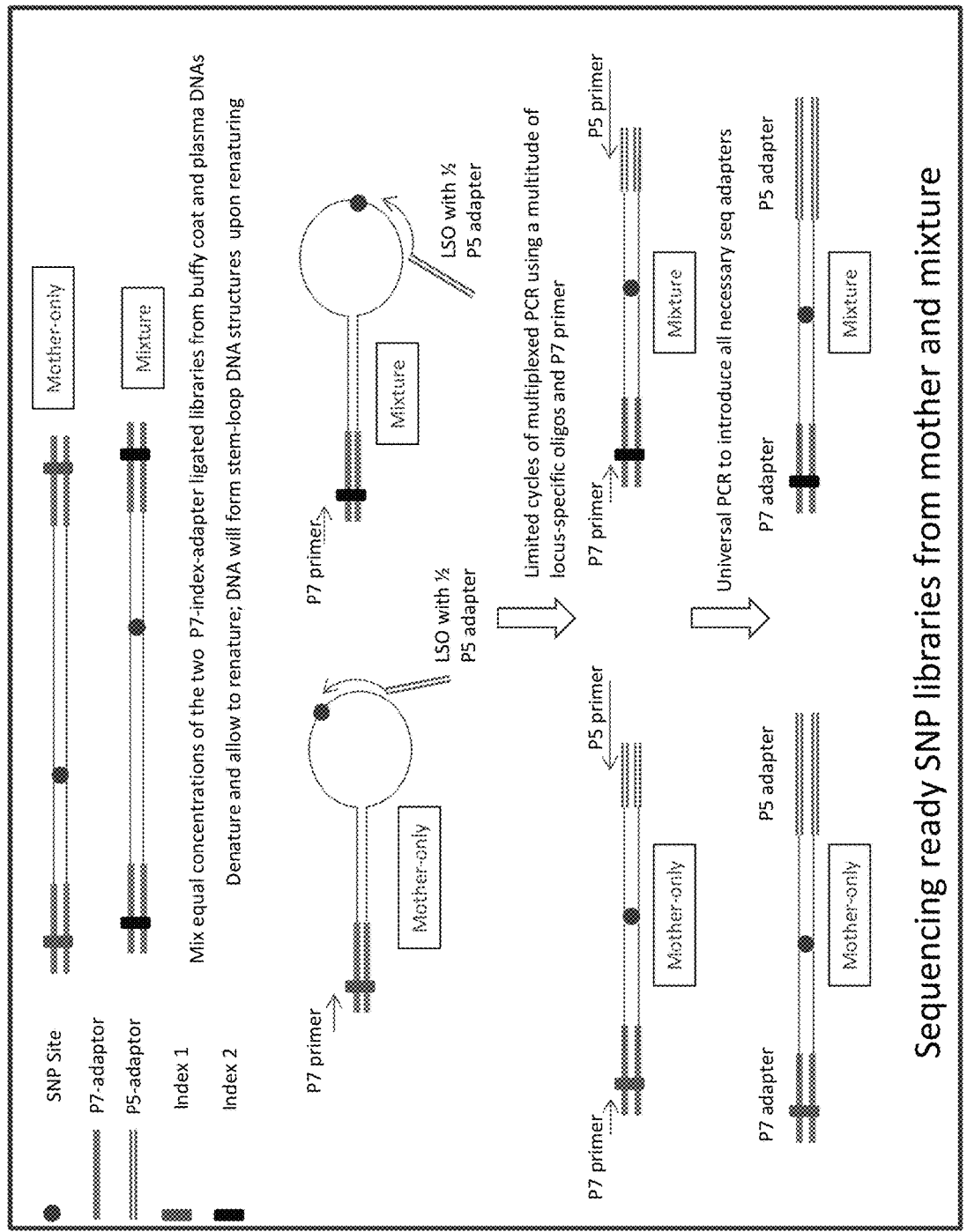

FIGS. 5A and 5B describe a workflow where the maternal only and the plasma mixture DNAs are indexed independently, mixed together and then subjected to the multiplexed SNP-interrogation at the same time in a single tube. The workflow uses ligation to incorporate two copies of the same index sequence into two ends of a fragment, which index sequence copies on two ends of the fragment then self-hybridize and form a stem-loop structure when the single strand fragment is denatured.

FIG. 5A shows the indexing operation that ligates a double stranded P7 adaptor and an index to the A-tailed fragments. The cellular DNA obtained from the buffy coat and the cfDNA from the plasma are indexed separately in separate tubes. The cellular DNA is enzymatically fragmented and SPRI-size selected to have fragments of about 170 bp before index ligation. The ligated fragments are then SPRI-cleaned and quantified.

FIG. 5B shows the indexed fragments are combined and further processed to selectively enrich and amplify the sequence of interest. The workflow proceeds by mixing approximately equal concentration and amount of indexed cellular DNA and cfDNA. After denaturing and renaturing, DNA fragments form stem-loop structures upon renaturing. Then the process applies two primers: a P7 primer and LSO primer that includes one half of P5 sequence. These primers are used in limited cycles of multiplex PCR, to pull down multiple locus-specific polymorphisms, and incorporate the P5 primer to the DNA fragments. Then universal PCR is performed to amplify the library fragments and to complete the extension of the P7 and P5 adaptors.

At the end of the universal PCR, all necessary sequences are available for multiplexed sequencing. Since each kind of DNA from the same patient sample is source-indexed uniquely, the downstream data from a given patient can be identified as arising as from mother-only and from the mixed DNA populations. The maternal only data can then be subtracted from the mixed DNA data. The methods exemplified in this workflow can be carried out using fetal-only DNA instead of maternal-only DNA. Alternatively or additionally, other nucleic acids, such as mRNA can be used.

Sequencing Library Preparation Involving Mother-only Cellular DNA

In some embodiments, the method for determining a sequence of interest for a fetus uses a step of incorporating indexes into sequence fragments. Indexes are identifiable during downstream processing and analyses, providing indicators to identify the source of the genetic materials. In some embodiments, the indexes indicate whether the material is derived from a cellular nucleic acid fraction or cell-free nucleic acid fraction. In some embodiments, the indexes are incorporated into the sequences by hybridizing and extending primer sequences comprising the indexes. In some embodiments, the primer sequences also comprise locus-specific extension oligonucleotides. This allows the primer to target sequence of interest, thereby allowing selective enrichment of the sequence of interest before further amplification and/or sequencing. In some embodiments, the locus-specific extension oligonucleotides are selective to two or more alleles of a disease related gene, thereby allowing the primer to target the two alleles of the disease related gene. In some embodiments, the primer sequences also include adaptors, or portions of adaptors, for next generation sequencing. In some embodiments, indexes are incorporated by ligation instead of primer extension, which may involve ligating sequences comprising the indexes. In some embodiments, the indexes may be incorporated ligating sequences that also contain sequencing adaptors, or portions thereof, for next generation sequencing. In some embodiments, indexes and/or adaptors are mediated by Tn5 transposase, and the sequencing libraries are transposon insertion libraries.

In some embodiments, the method also involves incorporating an individual-specific index to the sequencing libraries. The individual-specific index indicates the identity of the pregnant mother that provides the sample. This allows the pregnant mother's nucleic acids to be processed with other individuals' nucleic acids for parallel sequencing.

In some embodiments, the method involves starting with substantially the same size and/or substantially the same concentration of cellular DNA and cfDNA in separate reaction environments, e.g., testing tubes. In various embodiments, the sizes and/or concentrations for two reactions are within about 5%, 10%, 15%, 20%, 30%, 40%, or 50% of one another. The method involves enriching wild-type and mutant regions using probes that target both alleles of disease related gene(s) and have different indices for cellular DNA and cfDNA, the indices are incorporated into the targeted sequences in the separate reaction environment. The method further involves mixing the cellular DNA and cfDNA with enriched targeted regions and amplifying the DNA using universal PCR primers. The amplified product will be sequencing-ready targeted libraries of both cellular DNA for the mother and cfDNA for the mother and fetus. The sequencing results may then be used to determine a sequence of interest for the fetus. The method may determine the zygosity of the fetus and/or fetal fraction of the cfDNA.

In some embodiments, the method further comprises amplifying a plurality of training sequences before sequencing the combined sample. In some embodiments, the plurality of training sequences comprises more than 10, 50, 60, 100, 500, 1000, or 5000 sequences. In some embodiments, some or all of the training sequences contain polymorphisms, e.g., one polymorphism per training sequence. In some embodiments, the method further comprises obtaining distribution statistics of sequence tag counts for the training sequences. In some embodiments, the method further involves using the distribution statistics to determine the zygosity of the sequence of interest for the fetus.

In some embodiments, the cellular DNA and cfDNA are also enriched for training sequences or sites. In some embodiments, more than about 10, 50, 60, 100, 500, 1000, or 5000 SNP sites are used as training sites to understand distribution counts of SNPs sequence tags in the assay where the mother is heterozygous and the fetus is homozygous.

In some embodiments, the methods described herein can utilize next generation sequencing technologies (NGS), that allow multiple samples to be sequenced individually as genomic molecules (i.e., singleplex sequencing) or as pooled samples comprising indexed nucleic acids (e.g., multiplex sequencing) on a single sequencing run. These methods can generate up to several hundred million reads of nucleic acid sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Solid Phase Reversible Immobilization (SPRI) beads are widely used for purification of PCR amplified colonies in several DNA sequencing protocols. SPRI beads are paramagnetic (magnetic only in a magnetic field) and this prevents them from clumping and falling out of solution. Each bead is made of polystyrene surrounded by a layer of magnetite, which is coated with carboxyl molecules, which reversibly bind DNA in the presence of the "crowding agent" polyethylene glycol (PEG) and salt (20% PEG, 2.5M NaCl is the magic mix).

In some embodiments, the sequencing libraries are transposon insertion libraries. Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in U.S. patent application Ser. No. 13/555,037 filed on Jul. 20, 2012, which is incorporated by reference by its entirety.

Processing Workflow Involving Analyses of Fetus-Only Cellular DNA

Overall Workflow Involving Analyses of Fetus-Only Cellular DNA

This section describes how biological samples from a pregnant mother is obtained to extract fetal cellular DNA and fetus-and-mother cfDNA, which are then used to prepare libraries that provide DNA to derive information for analysis of a sequence of interest. In some embodiments the sequence of interest includes a single nucleotide polymorphism that is related to a medical condition or biological trait. In the embodiments that involve chromosomes or segments of chromosomes, the methods disclosed herein may be used to identify monosomies or trisomies, e.g. trisomy 21 that causes Down Syndrome.

In some embodiments, fetal cellular DNA can be obtained from fetal nucleated red blood cells circulating in the maternal blood, and mother-and-fetus mixed cfDNA can be obtained from the plasma of the maternal blood. The two sources of DNA are then combined and further processed together to obtain two sequencing libraries having indexes identifying the sources of the DNA. The sequencing information obtained from the two libraries is used to determine a sequence of interest. For instance, in some embodiments, sequence information from the fetal cellular DNA can be used to validate a mosaicism call obtained from cfDNA analysis. Additionally, the combination of sequence information from both the fetal cellular DNA and the cfDNA may provide a higher confidence interval and/or reduce noise in calls for copy number variation, fetal fraction, and/or fetal zygosity. For instance, information from the fetal cellular DNA can be used to reduce the noise in the data, thereby helping to differentiate a homozygous fetus from a heterozygous fetus case (when the mother is heterozygous).

In some embodiments, a targeted amplification and sequencing method can be used. In other embodiments, whole genome amplification may be applied before sequencing. To reduce processing biases and otherwise permit reliable comparison of the cell free nucleic acid sequences and the cellular nucleic acid sequences, the two nucleic acid samples are processed similarly in some embodiments. For example, they can be sequenced in a mixture of the nucleic acids from both samples by a multiplexing technique. In some embodiments, cellular nucleic acids and cell free nucleic acids are obtained from the same sample but then separated and indexed (or otherwise uniquely identified) in the separated fractions and then the fractions are pooled for amplification, sequencing, and the like. In some implementations, the fetal cellular nucleic acid fraction is enhanced before being combined with mother-and-fetus cell free nucleic acid fraction, such that the separately indexed cellular nucleic acid and cell free nucleic acid are made similar with regard to size and concentration prior to pooling for sequencing and other downstream processing.

Figure 6:
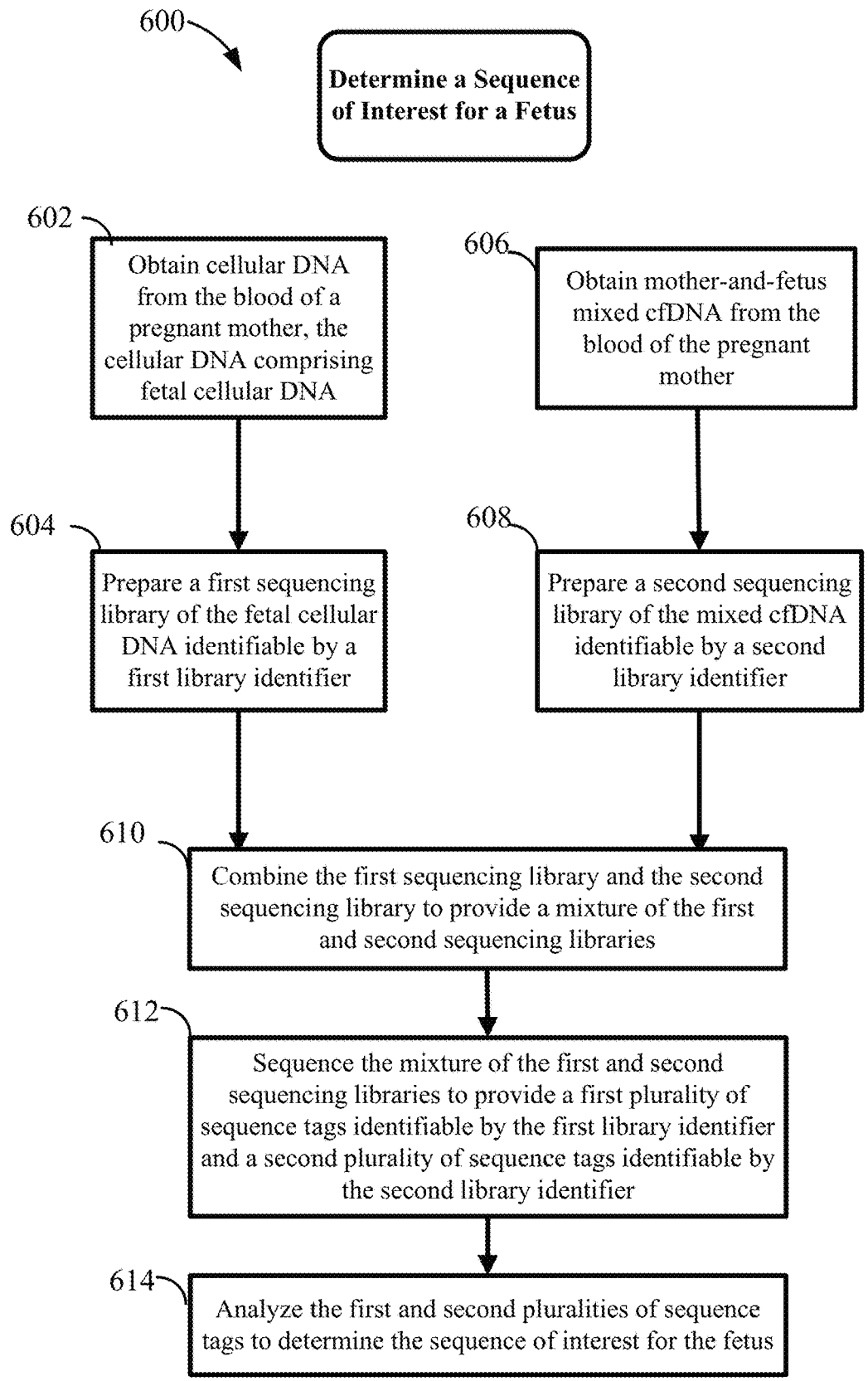
FIG. 6 is a flowchart showing a process for determining a sequence of interest for the fetus using fetal cellular DNA and mother-and-fetus cfDNA according to some embodiments of the disclosure.

FIG. 6 shows a process flow of a method 600 for determining a sequence of interest of a fetus according to some embodiments of the disclosure. FIGS. 7-12 are specific implementations of various components of the process flow depicted in FIG. 6. In some embodiments, method 600 involves obtaining cellular DNA from a maternal blood sample of a pregnant mother. See block 602. In some embodiments, the cellular DNA includes both maternal cellular DNA and fetal cellular DNA. In some embodiments, the fetal cellular DNA is isolated from maternal cellular DNA before further downstream processing. The fetal cellular DNA includes at least a sequence that maps to the sequence of interest. In some embodiments, the sequence of interest includes polymorphic sequences of a disease related gene. In some embodiments, the sequence of interest comprises a site of an allele associated with a disease. In some embodiments, the sequence of interest comprises one or more of the following: single nucleotide polymorphism, tandem repeat, deletion, insertion, a chromosome or a segment of a chromosome.

In some embodiments, fetal cellular DNA is obtained from fetal nucleated red blood cells (NRBCs) circulating in the maternal blood sample. The fetal cellular DNA and the fetal NRBCs may be obtained from maternal peripheral blood as described herein. In some embodiments, the fetal NRBCs are obtained from an erythrocyte fraction of a maternal blood sample. In some embodiments, the fetal cellular DNA may be obtained from other fetal cell types circulating in the maternal blood.

In some embodiments, the method also involves obtaining mother-and-fetus mixed cfDNA from the pregnant mother. See block 606. The cfDNA includes at least one sequence that maps to the at least one sequence of interest. In some embodiments, the cfDNA is obtained from the plasma of a blood sample from the mother. In some embodiments, the same blood sample also provides the fetal NRBC as the source of the fetal cellular DNA. Of course, the cellular DNA and cfDNA may also be obtained from different samples of the same mother.

In some embodiments, the method applies an indicator of the source of DNA as being from the fetal cellular DNA or from the cfDNA. In some embodiments, this indicator comprises a first library identifier and a second library identifier. In some embodiments, the process involves preparing a first sequencing library of fetal cellular DNA obtained from operation 602, wherein the first sequencing library is identifiable by a first library identifier. Block 604. In some embodiments, the first library identifier is a first index sequence that is identifiable in downstream sequencing steps. In some embodiments, the indicator of the source of DNA also comprises a second sequencing library of the cfDNA identifiable by a second library identifier. Block 608. In preparing sequence libraries, the method may involve incorporating indexes to each of said sequence libraries, wherein the indexes incorporated to said first library differ from the indexes incorporated to said second library. The indexes contain unique sequences (e.g., bar codes) that are identifiable in downstream sequencing steps, thereby providing an indicator of the source of the nucleic acids.

In some embodiments, the indicator of the source of DNA may be provided by other methods such as size separation.

In some embodiments, the method proceeds by combining at least a portion of the fetal cellular DNA of the first sequencing library and at least a portion of the cfDNA of the second sequencing library to provide a mixture of the first and second sequencing libraries. See block 610.

In FIG. 6, preparation of the first sequencing library and the second sequencing library is shown as two separate branches of the workflow, and the prepared libraries are combined to obtain a mixture of the first and second sequencing libraries. However, in some embodiments the two libraries are indexed separately at the beginning, then further processed in a combined sample. In some embodiments, the method involves further processing the combined sample to prepare or modify sequencing libraries. In some embodiments, the further processing involves incorporating sequencing adaptors (e.g., paired end primers) for massively parallel sequencing.

In some embodiments, the method then proceeds with sequencing at least a portion of the mixture of the first and second sequencing libraries to provide a first plurality of sequence tags identifiable by the first library identifier and a second plurality of sequence tags identifiable by second library identifier. See block 612. In some embodiments, the sequence reads are then mapped to a reference sequence containing the sequence of interest, thereby providing sequence tags mapped to the sequence of interest. In some embodiments, the sequence of interest may identify the presence of an allele. In some embodiments, the sample has been selectively enriched for the sequence of interest.

In some embodiments, instead of or in addition to selective enrichment of the sequence of interest before sequencing, the sample may be amplified by whole genome amplification. In some of these embodiments, the sequence reads are aligned to a reference genome comprising a sequence of interest (e.g., chromosome, chromosome segment) that are typically longer than in the embodiment with selective enrichment targeting shorter sequences of interest (e.g., SNPs, STRs, and sequences of up to kb in size). The sequence reads mapping to the sequence of interest provide sequence tags for the sequence of interest, which can be used to determine a genetic condition, e.g., aneuploidy, related to the sequence of interest.

In some embodiments, the method applies massively parallel sequencing. Various sequencing techniques may be used, including but not limited to, sequencing by synthesis and sequencing by ligation. In some embodiments, sequencing by synthesis uses reversible dye terminators. In some embodiments, single molecule sequencing is used.

In some embodiments, the method further involves analyzing the first and second pluralities of sequence tags to determine the at least one sequence of interest. See block 614. At least a portion of the plurality of sequence tags map to the at least one sequence of interest. In some embodiments, the method determines the presence or abundance of sequence tags mapping to the sequence of interest. This may include determining CNV (e.g., aneuploidy) and non-NCV abnormality. Particularly, the method may determine the relative amounts of two alleles in each of the cfDNA and cellular DNA. In some embodiments, the method may detect that the fetus has a genetic disorder by determining that the fetus is homozygous of a disease causing allele of a disease related gene wherein the mother is heterozygous of the allele.

In some embodiments, the method starts with cellular DNA and cfDNA in separate reaction environments, e.g., test tubes. In some embodiments, the method involves enriching wild-type and mutant regions using probes that target both alleles of disease related gene(s) and have different indices for cellular DNA and cfDNA, the indices are incorporated into the targeted sequences in the separate reaction environment. The method further involves mixing the cellular DNA and cfDNA with enriched targeted regions and amplifying the DNA using universal PCR primers. In some embodiments, whole genome amplification instead of targeted sequence amplification is applied. The amplified product will be sequencing-ready libraries of both cellular DNA of the fetus and cfDNA for the mother and fetus. The sequencing results may then be used to determine a sequence of interest for the fetus. In some embodiments, determining the sequence of interest provides information for detecting a CNV or non-CNV chromosomal anomaly involving the sequence of interest. In some embodiments, the method may determine the zygosity of the fetus and/or fetal fraction of the cfDNA.

In some embodiments, the method further involves determining a plurality of training sequences from the cfDNA and the cellular DNA, which can be used to determine a CNV or non-CNV chromosomal anomaly involving a sequence of interest. Some embodiments further use the sequence information obtained from the cellular DNA to determine the fetal fraction of the cfDNA. The methods exemplified in FIG. 6 and set forth above with respect to DNA can be carried out for other nucleic acids (e.g. mRNA) as well.

Obtain cfDNA and Fetal Cellular DNA

In various embodiments, mother-and-fetus mixed cfDNA and fetal cellular DNA are obtained from maternal peripheral blood to provide the genetic materials, as respectively shown in block 602 and block 606 of FIG. 6. The genetic materials are used to generate two identifiable libraries as respectively shown in block 604 and block 608 of FIG. 6. The two libraries are then combined for further downstream processing and analyses. Various methods may be used to obtain cfDNA and fetal cellular DNA. Two processes are described below as examples to illustrate applicable methods for obtaining cfDNA and fetal cellular DNA for downstream processing and analyses.

A Process of Obtaining DNA Using Fixed Blood

Fetal cellular DNA and mixed cfDNA may be obtained from fixed or unfixed blood samples. Maternal peripheral blood samples can be collected using any of a number of various different techniques. Techniques suitable for individual sample types will be readily apparent to those of skill in the art. For example, in certain embodiments, blood is collected in specially designed blood collection tubes or other container. Such tubes may include an anti-coagulant such as ethylenediamine tetracetic acid (EDTA) or acid citrate dextrose (ACD). In some cases, the tube includes a fixative. In some embodiments, blood is collected in a tube that gently fixes cells and deactivates nucleases (e.g., Streck Cell-free DNA BCT tubes). See US Patent Application Publication No. 2010/0209930, filed Feb. 11, 2010, and US Patent Application Publication No. 2010/0184069, filed Jan. 19, 2010 each previously incorporated herein by reference.

Figure 7:
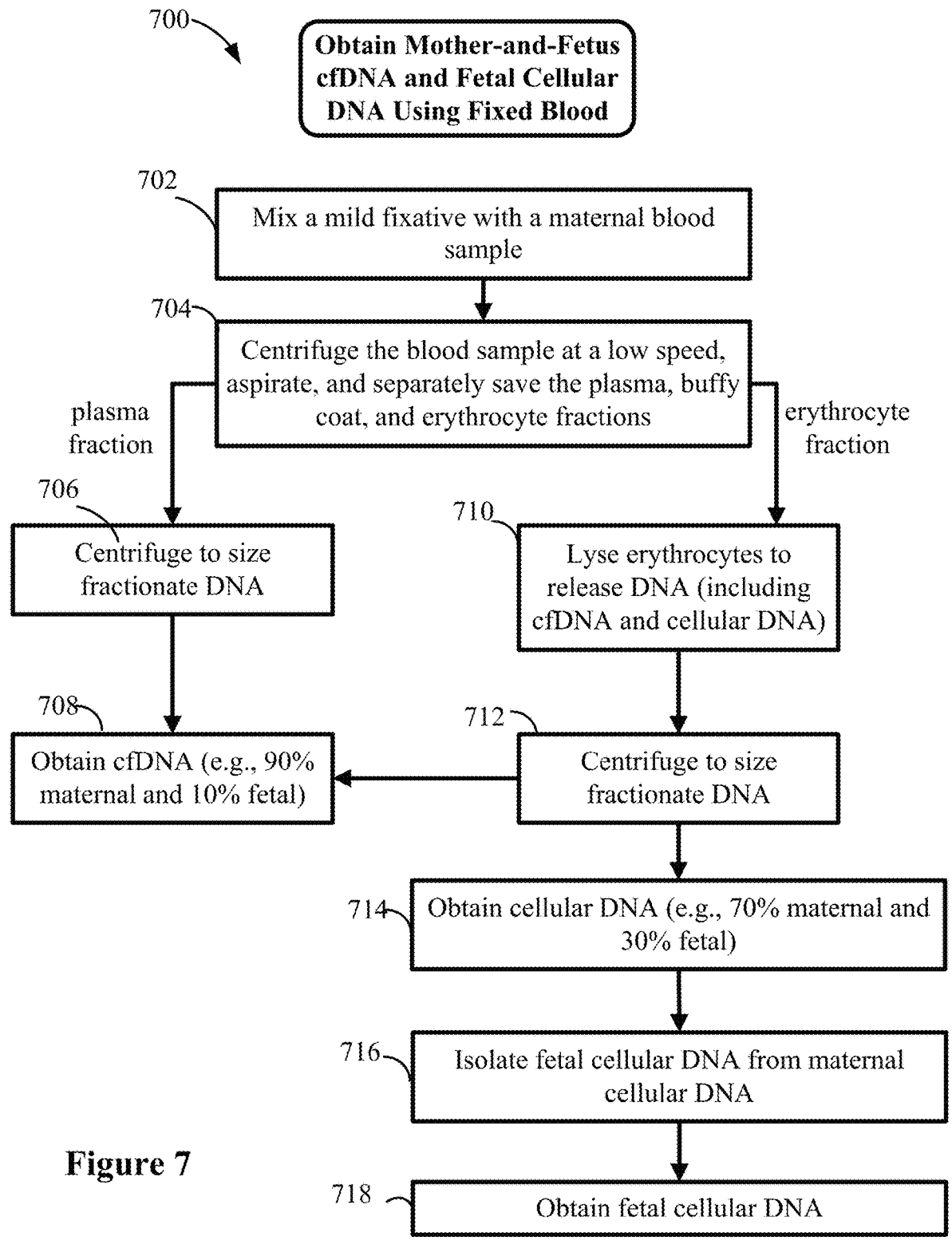
FIG. 7 is a flowchart showing a process of obtaining mother-and-fetus cfDNA and fetal cellular DNA using fixed blood.

FIG. 7 depicts a flowchart of a process 700 to obtain mother-and-fetus cfDNA and fetal cellular DNA using a fixed whole blood sample obtained from a pregnant mother. Of course, the process may be modified to use two samples from the same pregnant mother, with one sample providing cfDNA and one providing cellular DNA. Process 700 begins with mixing a mild fixative with a maternal blood sample that includes cellular DNA and cfDNA. Block 702. The cellular DNA may originate from maternal cells and/or fetal cells. The blood sample can be collected by any one of many available techniques. Such techniques should collect a sufficient volume of sample to supply enough cfDNA to satisfy the requirements of the sequencing technology, and account for losses during the processing leading up to sequencing.

In certain embodiments, blood is collected in specially designed blood collection tubes or other container. Such tubes may include an anti-coagulant such as ethylenediamine tetracetic acid (EDTA) or acid citrate dextrose (ACD). In some cases, the tube includes a fixative. In some embodiments, blood is collected in a tube that gently fixes cells and deactivates nucleases (e.g., Streck Cell-free DNA BCT tubes). See US Patent Application Publication No. 2010/0209930, filed Feb. 11, 2010, and US Patent Application Publication No. 2010/0184069, filed Jan. 19, 2010 each previously incorporated herein by reference.

Generally, it is desirable to collect and process cfDNA that is uncontaminated with DNA from other sources such as white blood cells. Therefore, white blood cells can be removed from the sample and/or treated in a manner that reduces the likelihood that they will release their DNA.

Process 700 then proceed to separate a plasma fraction from an erythrocyte fraction of the fixed blood sample. In some embodiments, to separate the plasma fraction from the erythrocyte fraction, the process centrifuges the blood sample at a low speed, then aspirates and separately saves the plasma, buffy coat, and erythrocyte fractions. See block 704.

In some embodiments, the blood sample is centrifuged, sometimes for multiple times. The first centrifugation step applies a low speed to produce three fractions: a plasma fraction on top, a buffy coat containing leukocytes, and an erythrocyte fraction on the bottom. This first centrifugation process is performed at relatively low g-force in order to avoid disrupting the hematocytes (e.g. leukocytes, nucleated erythrocytes, and platelets) to a point where their nuclei break apart and release DNA into the plasma fraction. Density gradient centrifugation is typically used. If this first centrifugation step is performed at too high of an acceleration, some DNA from the leukocytes would likely contaminate the plasma fraction. After this centrifugation step is completed, the plasma fraction and erythrocyte fraction are separated from each other and can be further processed.

The plasma fraction can be subjected to a second higher speed centrifugation to size fractionate DNA, removing larger particulates from the plasma, leaving cfDNA in the plasma. See block 706. In this step, additional particulate matter from the plasma is pelleted as a solid phase and removed. This additional solid material may include some additional cells that also contain DNA that would otherwise contaminate the cell free DNA that is to be analyzed. In some embodiments, the first centrifugation is performed at an acceleration of about 1600 g and the second centrifugation is performed at an acceleration of about 16,000 g.

While a single centrifugation process from normal blood is possible to obtain cfDNA, such process has been found to sometimes produce plasma contaminated with white blood cells. Any DNA isolated from this plasma will include some cellular DNA. Therefore, for cfDNA isolation from normal blood, the plasma may be subjected to a second centrifugation at high-speed to pellet out any contaminating cells.

After removing larger sized particulates from the plasma by size fractionation, the process 700 proceeds to isolate/purify cfDNA from the plasma. See block 708. In some embodiments, the isolation can be performed by the following operations.

A. Denature and/or degrade proteins in plasma (e.g. contact with proteases) and add guanidine hydrochloride or other chaotropic reagent to the solution (to facilitate driving cfDNA out of solution)

B. Contact treated plasma with a support matrix such as beads in a column. cfDNA comes out of solution and binds to matrix.

C. Wash the support matrix.

D. Release cfDNA from matrix and recover the cfDNA for downstream process (e.g., indexed library preparation) and statistical analyses.

After a plasma fraction is collected as described, the cfDNA is extracted. Extraction is actually a multistep process that involves separating DNA from the plasma in a column or other solid phase binding matrix. The extracted cfDNA usually includes both maternal and fetal cfDNA. Depending on the pregnancy stage and physiological condition of the mother and the fetus, the cfDNA can include up to 10% of fetal DNA in some examples.

The first part of this cfDNA isolation procedure involves denaturing or degrading the nucleosome proteins and otherwise taking steps to free the DNA from the nucleosome. A typical reagent mixture used to accomplish this isolation includes a detergent, protease, and a chaotropic agent such as guanine hydrochloride. The protease serves to degrade the nucleosome proteins, as well as background proteins in the plasma such as albumin and immunoglobulins. The chaotropic agent disrupts the structure of macromolecules by interfering with intramolecular interactions mediated by non-covalent forces such as hydrogen bonds. The chaotropic agent also renders components of the plasma such as proteins negative in charge. The negative charge makes the medium somewhat energetically incompatible with the negatively charged DNA. The use of a chaotropic agent to facilitate DNA purification is described in Boom et al., "Rapid and Simple Method for Purification of Nucleic Acids", J. Clin. Microbiology, v. 28, No. 3, 1990.

After this protein degradation treatment, which frees, at least partially, the DNA coils from the nucleosome proteins, the resulting solution is passed through a column or otherwise exposed to support matrix. The cfDNA in the treated plasma selectively adheres to the support matrix. The remaining constituents of the plasma pass through the binding matrix and are removed. The negative charge imparted to medium components facilitates adsorption of DNA in the pores of a support matrix.

After passing the treated plasma through the support matrix, the support matrix with bound cfDNA is washed to remove additional proteins and other unwanted components of the sample. After washing, the cfDNA is freed from the matrix and recovered. Notably, this process loses a significant fraction of the available DNA from the plasma. Generally, support matrixes have a high capacity for cfDNA, which limits the amount of cfDNA that can be easily separated from the matrix. As a consequence, the yield of cfDNA extraction step can be quite low. Typically, the efficiency is well below 50% (e.g., it has been found that the typical yield of cfDNA is 4-12 ng/ml of plasma from the available ~30 ng/ml plasma).

Other methods may be used to obtain cfDNA from a maternal blood sample with higher yield. One example is further described here. For instance, in one embodiment, a device can be used to collect 2-4 drops of patient/donor blood (100-200 ul) and then separate the plasma from the hematocrit using a specialized membrane. The device can be used to generate the required 50-100 μl of plasma for NGS library preparation. Once the plasma has been separated by the membrane, it can be absorbed into a pretreated medical sponge. In certain embodiments, the sponge is pretreated with a combination of preservatives, proteases and salts to (a) inhibit nucleases and/or (b) stabilize the plasma DNA until downstream processing. Products such as Vivid Plasma Separation Membrane (Pall Life Sciences, Ann Arbor, Mich.) and Medisponge 50PW (Filtrona technologies, St. Charles, Mich.) can be used. The plasma DNA in the medical sponge can be accessed for NGS library generation in a variety of ways. (a) Reconstitute and extract that plasma from the sponge and isolate DNA for downstream processing. Of course, this approach may have limited DNA recovery efficiency. (b) Utilize the DNA-binding properties of the medical sponge polymer to isolate the DNA. (c) Conduct direct PCR-based library preparation using the DNA that is bound to the sponge. This may be conducted using any of the cfDNA library preparation techniques described herein.

The purified cfDNA obtained from operation 708 can be used to prepare a library for sequencing. To sequence a population of double-stranded DNA fragments using massively parallel sequencing systems, the DNA fragments must be flanked by known adapter sequences. A collection of such DNA fragments with adapters at either end is called a sequencing library. Two examples of suitable methods for generating sequencing libraries from purified DNA are (1) ligation-based attachment of known adapters to either end of fragmented DNA, and (2) transposase-mediated insertion of adapter sequences. There are many suitable massively parallel sequencing techniques. Some of these are described below.

Note that operations 702-708 described so far for process 700 depicted in FIG. 7 largely overlap with operations 802-808 in process 800 of FIG. 8 described below.

Process 700 also provides fetal cellular DNA from the maternal blood sample, which makes use of the erythrocyte fraction obtained from the low-speed centrifugation of operation 704. In some embodiments, the process involves lysing the erythrocytes in the erythrocyte fraction DNA, the product from which includes both cfDNA and cellular DNA. See block 710. Next, process 700 proceeds by centrifuging the sample to size fractionate DNA, allowing the separation of cfDNA and cellular DNA, since cfDNA is much smaller in size than cellular DNA as described above. See block 712.

In some embodiments, this centrifugation operation may be similar to the centrifugation of operation 706, performed at 16,000 g. In some implementations, the cfDNA obtained from the erythrocyte fraction may optionally be combined with the cfDNA obtained from the plasma fraction for downstream processing. See block 708.

Process 700 allows obtaining cellular DNA from the erythrocyte fraction. See block 714. The cellular DNA obtained from the erythrocytes fraction largely originates from NRBCs. During pregnancy, most of the NRBC that are present in the maternal blood stream are those that have been produced by the mother herself. See Wachtel, et al., Prenat. Diagn. 18: 455-463 (1998). In some instances, the cellular DNA include up to 50% of fetal cellular DNA. For example, the cellular DNA may include 70% of maternal DNA and 30% of fetal DNA as shown by Wachtel et al.

In some embodiments, process 700 proceeds by isolating the fetal cellular DNA from maternal cellular DNA. See block 706. Various methods may be applied to separate the two sources of cellular DNA by taking advantage of the different characteristics of the two sources of DNA. See block 716. For instance, it has been shown that fetal DNA tends to have a higher state of methylation than maternal DNA. Therefore, mechanisms that differentiate methylation may be used to separate fetal cellular DNA from maternal cellular DNA. See, e.g., Kim et al., Am J Reprod Immunol. 2012 July; 68(1):8-27, for different methylation characteristics of maternal versus fetal cells.

Additionally, FISH can be used to detect and localize specific DNA or RNA targets from fetal cells. Some embodiments may ascertain fetal origin by FISH that identifies fetal specific DNA markers. Therefore, process 700 allows one to obtain fetal cellular DNA, which can then be further processed and analyzed. See block 718.

A Process of Obtaining DNA Using Unfixed Blood

The disclosure also provides methods for obtaining fetal cellular DNA and mixed cfDNA using unfixed blood samples. FIG. 8 is a flowchart showing a process of such a method. The operations for obtaining cfDNA depicted in FIG. 8 largely overlap with those in the process depicted in FIG. 7. Therefore blocks 704, 706 and 708 mirror blocks 804, 806 and 808.

Briefly, process 800 starts by mixing an anti-coagulant such as EDTA or ACD with the maternal blood sample without using a fixative. See block 802. Process 800 proceeds by separating a plasma fraction and an erythrocyte fraction from the blood sample by centrifugation. See block 804. As in block 804, the centrifugation may be performed at a lower-speed, such as 1600 g. The sample is then aspirated, and plasma, buffy coat, and the erythrocyte fractions are separately saved. The plasma fraction obtained from operation 804 and then undergo a second centrifugation at a higher speed such as 16,000 g to size fractionate DNA, spinning out larger particulates and leaving smaller cfDNA in the plasma. See block 806. Process 800 provides means to obtain cfDNA from the plasma that can be used for further processing and analysis. See block 808.

Operations 810-818 of process 800 allow isolation of fetal NRBCs form the erythrocyte fraction, and obtaining fetal cellular DNA from the isolated fetal NRBCs. Operation 810 involves adding isotonic buffer to the erythrocyte fraction. Then the process proceeds by centrifugation to pellet intact erythrocytes. See block 814. In some embodiments, this centrifugation is performed at a lower speed than that in operation 806 in order to avoid rupturing the erythrocytes. The supernatant from this centrifugation includes cfDNA that can be combined with the cfDNA obtained from the plasma fraction for downstream processing and analysis. See block 808. The pellet, or compacted precipitant, includes intact erythrocytes from both the mother and the fetus, wherein the erythrocytes from the mother include a large portion of enucleated RBCs and a small number of NRBCs.

In some embodiments, process 800 proceeds by washing erythrocyte pellet with isotonic buffer, then centrifuging to collect maternal enucleated RBCs and NRBCs. The NRBCs include both maternal and fetal NRBCs, with up to 30% of fetal cells in some embodiments as discussed above. Process 800 then proceeds by isolating fetal NRBCs from maternal cells. See block 818. One can then obtain fetal cellular DNA from the isolated fetal NRBCs. See block 820.

Isolate Fetal NRBC and Fetal Cellular DNA

Figure 8:
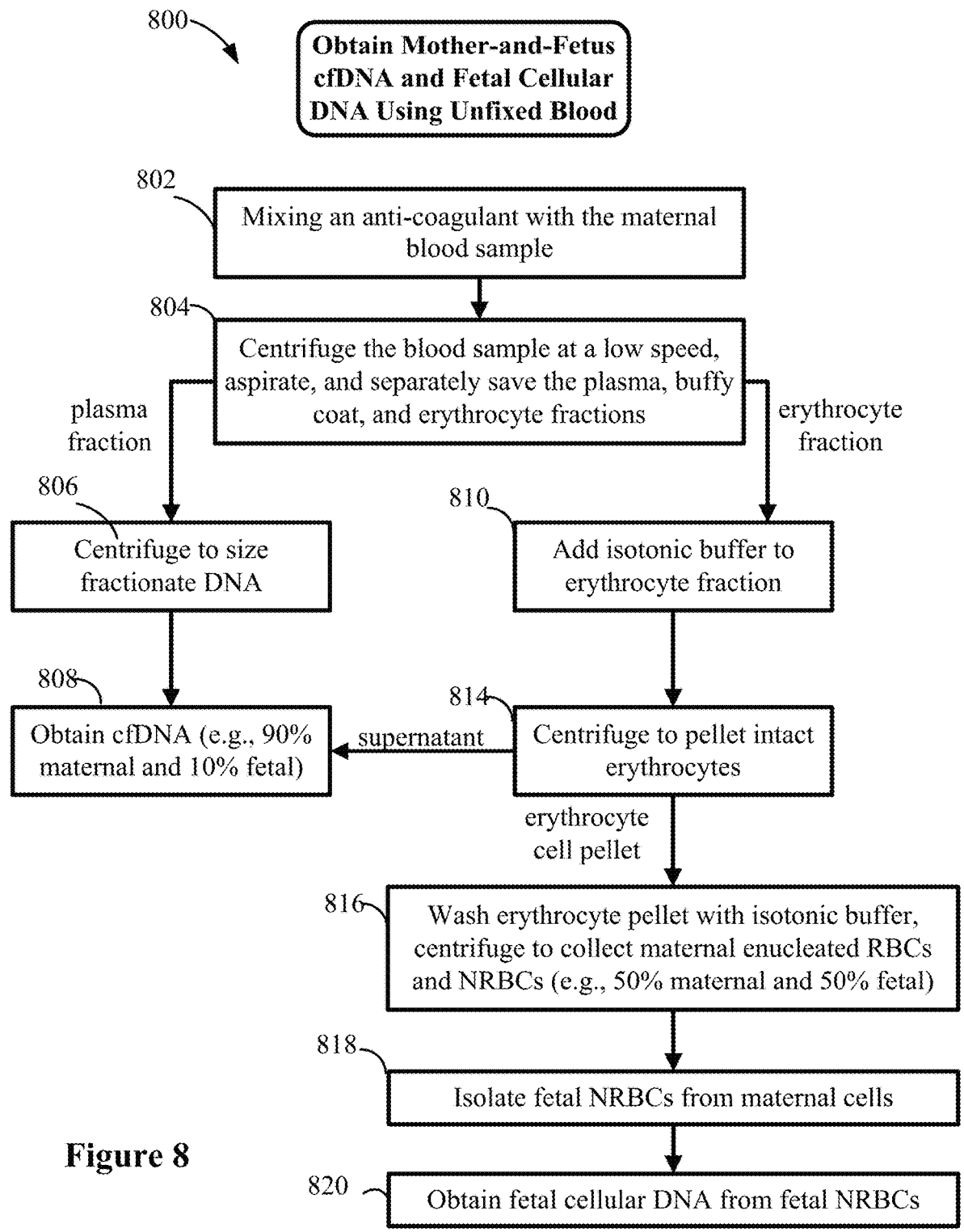
FIG. 8 is a flowchart showing a process of obtaining mother-and-fetus cfDNA and fetal cellular DNA using unfixed blood.

In various embodiments, such as operations 818 and 820 of process 800 depicted in FIG. 8, fetal NRBCs are isolated from maternal cells, and fetal cellular DNA is obtained from the isolated fetal NRBCs. Various combinations of methods may be applied to isolate NRBCs from maternal cells. In some embodiments, the methods can include various combinations of cell sorting with magnetic particles or flow cytometry, density gradient centrifugation, size-based separation, selective cell lysis, or depletion of unwanted cell populations. Often, these methods alone are not effective because each method may be able to remove some unwanted cells but not all. Therefore combination of methods can be used to isolate the desired fetal NRBCs.

In some embodiments, isolation of fetal NRBCs is combined with enrichment of the fetal NRBCs by one or more methods known in the art or described herein. The enrichment increases the concentration of rare cells or ratio of rare cells to non-rare cells in the sample. In some embodiments, when enriching fetal cells from a maternal peripheral venous blood sample, the initial concentration of the fetal cells may be about 1:50,000,000 and it may be increased to at least 1:5,000 or 1:500. Enrichment can be achieved by one or more types of separation modules described herein or in the prior art. See, e.g., U.S. Pat. No. 8,137,912 for some techniques for enrichment of fetal cells, which is incorporated by reference in its entirety. Multiple separation modules may be coupled in series for enhanced performance.

In some embodiments, the fetal cellular DNA used for downstream processing is obtained from one or more fetal NRBCs in the blood of the pregnant mother. In some embodiments, the method separates the fetal NRBCs from maternal erythrocytes in a cellular component of a blood sample of the pregnant mother. In some embodiments, separating the fetal NRBCs from the maternal erythrocytes comprises differentially lysing maternal erythrocytes. In some embodiments, separating the fetal NRBCs from the maternal erythrocytes comprises size-based separation and/or capture-based separation. The capture-based separation may comprise capturing the fetal NRBCs through binding one or more cellular markers expressed by fetal NRBCs. Preferably, the one or more cellular markers comprise a surface marker expressed by fetal NRBCs but not, or to a lesser degree, by maternal NRBCs. In some embodiments, the capture-based separation comprise binding magnetically responsive particles to fetal NRBCs, wherein the magnetically responsive particles have an affinity to one or more cellular markers expressed by fetal NRBCs. In some embodiments, the capture-based separation is performed by an automated immunomagnetic separation device, for example, as described in U.S. Pat. No. 8,071,395, which is incorporated herein by reference. In some embodiments, the capture-based separation comprises binding fluorescent labels to fetal NRBCs, wherein the fluorescent labels have an affinity to one or more cellular markers expressed by fetal NRBCs.

In various embodiments, cell surface markers expressed on fetal NRBCs are used for affinity based separation. For instance, some embodiments may use anti-CD71 to attach magnetic or fluorescent probes to transferrin receptors, which probes provide a mechanism for magnetic-activated cell sorting (MACS) or fluorescence-activated cell sorting (FACS). Cells from very early developmental stages can be isolated from umbilical cord blood using CD34. To enrich and identify erythroid cells from later developmental stages, surface markers such as CD71, glycophorin A, CD36, antigen-i, and intracellularly expressed hemoglobins may be used. Soybean agglutinin (SBA) may be used to isolate fetal NRBCs from the blood of pregnant mothers.

Many of the above surface markers are not exclusive to fetal NRBCs. Instead, they are also expressed to various degrees on maternal cells. Recently, monoclonal anti-bodies have been identified with affinity to fetal NRBCs but not to maternal bloods. For instance, Zimmermann et al. identified monoclonal antibody clones 4B8 and 4B9 that has specific affinity to fetal NRBCs. Experimental Cell Research, 319 (2013), 2700-2707. The mAb 4B8,4B9 and other similar mABs may be used to provide binding mechanism for MACS or FACS to isolate fetal NRBCs. Magnetism based cell separation may be implemented as a MagSweeper device, which is an automated immunomagnetic separation technology as disclosed in U.S. Pat. No. 8,071,395, which is incorporated by reference in its entirety. In some implementations, the MagSweeper can enrich circulating rare cells, e.g., fetal NRBCs in maternal blood, by an order of $10^8$-fold increase in concentration.

The fetal origin of isolated cells can be indicated by PCR amplification of Y chromosome specific sequences, by fluorescence in situ hybridization (FISH), by detecting ε-globin and γ-globin, or by comparing DNA-polymorphisms with STR-markers from mother and child. Some embodiments may use these indicators to separate fetal NRBCs from other cells, e.g., implemented as imaging-based separation mechanism by visualizing the indicator or as affinity-based separation mechanism by hybridizing with the indicator.

Figure 9:
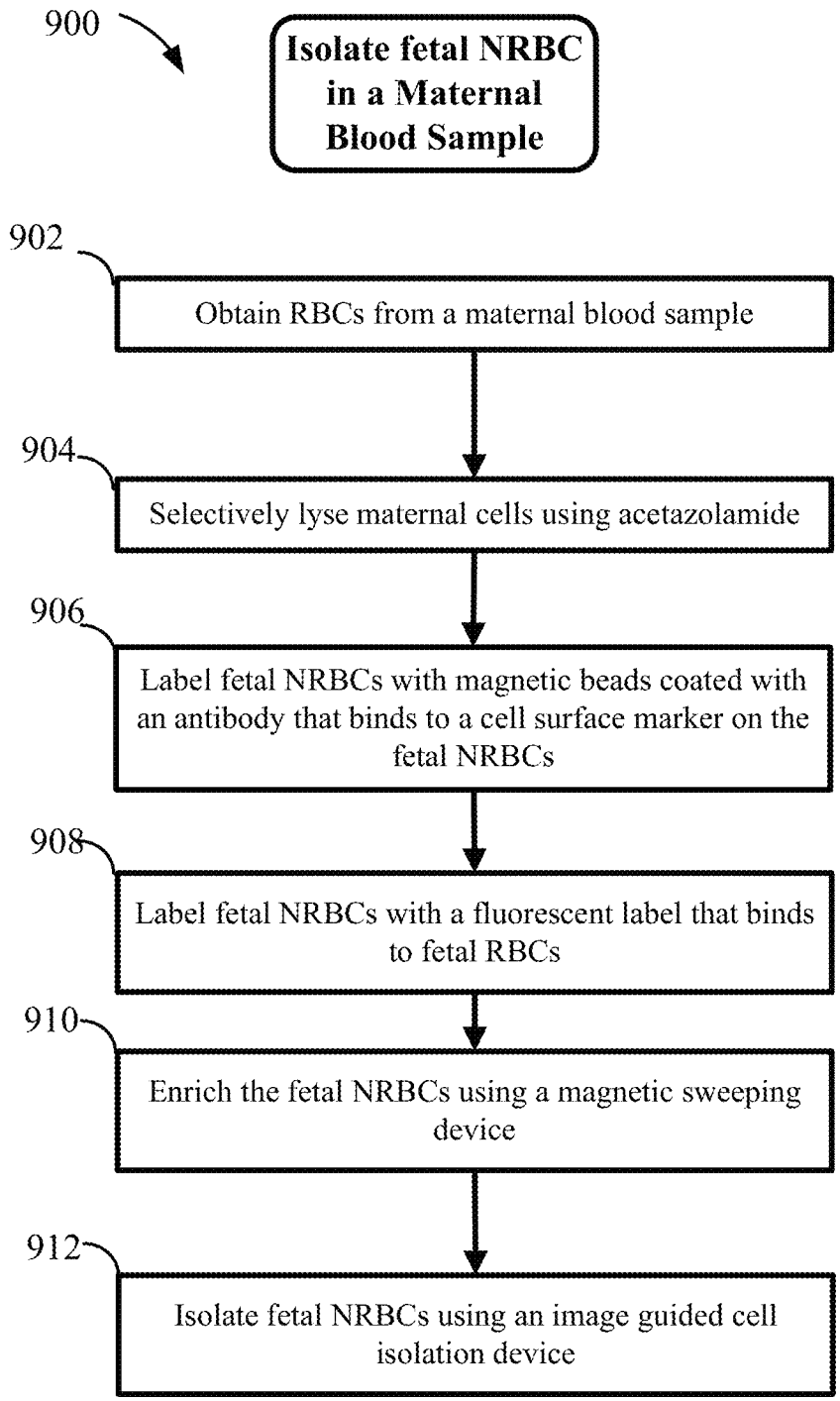
FIG. 9 is a flowchart showing a process for isolating fetal nucleated red blood cells (fetal NRBCs) from a maternal blood sample according to some embodiments.

FIG. 9 is a flowchart showing process 900 for isolating fetal NRBCs from a maternal blood sample according to some embodiments of the disclosure. Process 900 relates to process 800 in that process 900 provides one example of how operation 818 in FIG. 8 may be accomplished. Process 900 starts by obtaining RBCs from maternal blood sample, see block 902, such as using one or more density gradient centrifugations as described in the steps leading to step 816.

The process then proceeds to remove maternal enucleated RBCs and NRBCs from the RBCs by selectively lysing maternal erythrocytes using acetazolamide and lysing solutions containing $NH_4^+$ and $HCO_3^+$. See block 904. Erythrocytes can be quickly disrupted in lysing solutions containing $NH_4^+$ and $HCO_3^+$. Carbonic anhydrase catalyzes this hemolysis reaction, and is at least 5-fold lower in fetal cells than adult cells. Therefore the hemolytic rate is slower for fetal cells. This differential of hemolysis is augmented by acetazolamide, which is an inhibitor of carbonic anhydrase, and which penetrates fetal cell about 10 times faster than adult cells. Therefore the combination of acetazolamide and lysing solutions containing $NH_4^+$ and $HCO_3^+$ selectively lyses the maternal cells while sparing the fetal cells.

In one embodiment, the differential lyses may be performed as in the following example. The RBCs are centrifuged (e.g., 300 g, 10 min), re-suspended in phosphate-buffered saline (PBS) with acetazolamide, and incubated at room temperature for 5 min. Two and one half milliliters of lysis buffer (10 mM $NaHCO_3$, 155 mM $NH_4Cl$) is added and the cells are incubated for 5 min, centrifuged, re-suspended in lysis buffer, incubated for 3 min, and centrifuged.

After the selectively lysing maternal RBCs, lysed cells may be removed by centrifugation. In some embodiments, the process proceeds to label fetal NRBCs with magnetic beads coated with an antibody that binds to a cell surface marker expressed on the fetal NRBCs. See block 906. One or more of the surface markers expressed on fetal NRBCs described above may be the target for binding. In some embodiments, mAb 4B8, mAb 4B9, or anti-CD71 may be used as the antibody that binds to the surface of fetal NRBCs. The magnetic beads provides a means for magnetic separation mechanism to capture the fetal NRBCs, which are then selectively enriched. In some embodiments, the process proceeds to label the fetal NRBCs with a fluorescent label, e.g., oligonucleotides ("oligos") bound to fluorescein or rhodamine, which oligos bind to mRNA of markers of fetal NRBCs. In some embodiments, the fluorescent label binds to the mRNA of fetal hemoglobin, e.g., ε-globin and γ-globin.

Process 900 proceeds to enrich the fetal NRBCs using magnetic separation device such as the MagSweeper described above, which captures the NRBCs through the magnetic beads selectively attached to the NRBCs. See block 910. Finally, process 900 achieves isolation of fetal NRBCs using an image guided cell isolation device such as a FACS sensitive to the fluorescent label attached to the fetal NRBCs in operation 908. See block 912. The isolated fetal NRBCs may then be used to prepare an indexed fetal cellular DNA library. Some embodiments of the preparation of the indexed library are further described below.

In many embodiments, fetal NRBCs are first isolated from maternal RBCs and other cell types. Then fetal cellular DNA is obtained from the isolated fetal NRBCs. However, in some embodiments, fetal cellular DNA may be obtained by selectively lysing fetal NRBCs (as opposed to lysing the maternal cells). For example, fetal cells can be selectively lysed releasing their nuclei when a blood sample including fetal cells is combined with deionized water. Such selective lysis of the fetal cells allows for the subsequent enrichment of fetal DNA using, e.g., size or affinity based separation.

Sequence Library Preparation Involving Fetus-only Cellular DNA

The preparation of sequencing Libraries involving fetus-only cellular DNA is similar to that involving mother-only cellular DNA described above. However, some aspects are specific to preparing fetus-only cellular DNA, which are further described below.

In some embodiments, the method involves enriching wild-type and mutant regions using probes that target both alleles of disease related gene(s) and have different indices for cellular DNA and cfDNA, the indices are incorporated into the targeted sequences in the separate reaction environment. The method further involves mixing the cellular DNA and cfDNA with enriched targeted regions and amplifying the DNA using universal PCR primers. The amplified product will be sequencing-ready targeted libraries of both cellular DNA for the mother and cfDNA for the mother and fetus. In some embodiments, whole genome amplification is performed without selective enrichment of target sequences. The sequencing results may then be used to determine a sequence of interest for the fetus. The method may determine CNV or zygosity of the fetus. In some embodiments, the method determines the fetal fraction of the cfDNA.

Figure 10:
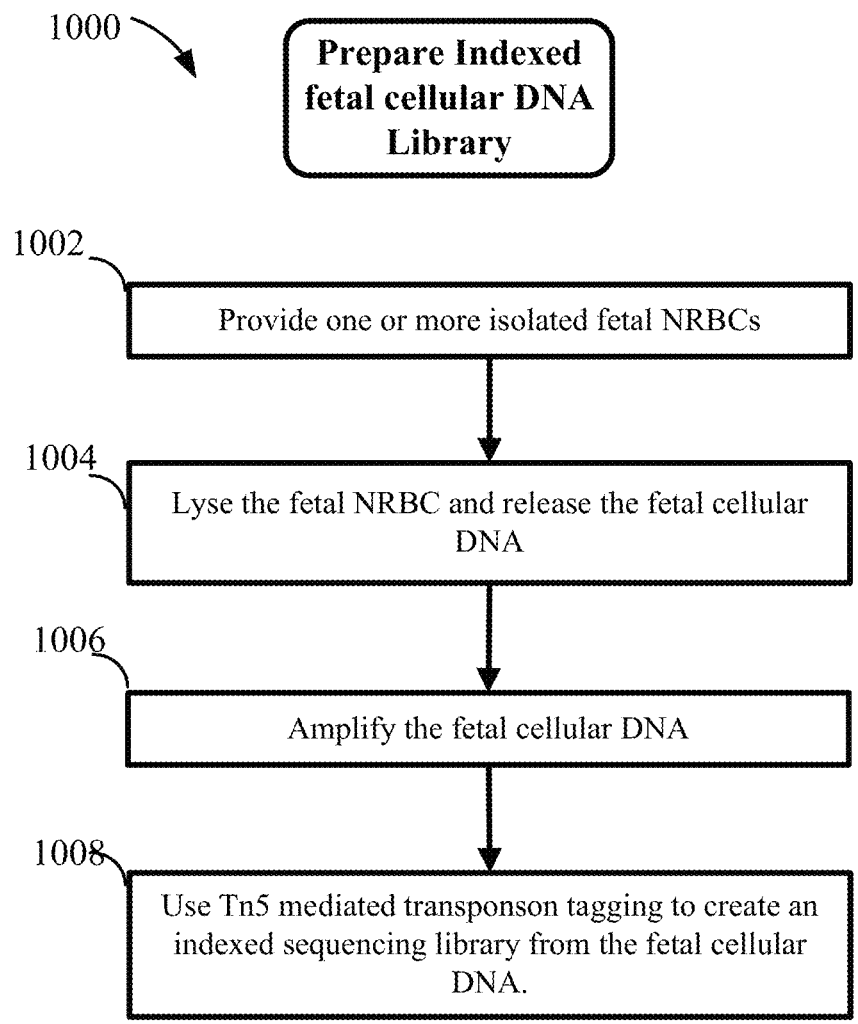
FIG. 10 is a flowchart showing a process for preparing an indexed library using fetal cellular DNA.

In some embodiments, fetal NRBCs are first isolated using various methods. Then the embodiments use the isolated fetal NRBCs to prepare an indexed library. FIG. 10 is a flowchart showing a process 1000 for preparing an indexed library of fetal cellular DNA. In some embodiments, process 1000 starts by providing one or more isolated fetal NRBCs. See block 1002. The fetal NRBCs may be isolated and obtained using methods such as the one described in FIG. 9. Then process 1000 proceeds by lysing the fetal NRBCs to release the fetal cellular DNA. See block 1004. In some embodiments, process 1000 optionally includes amplifying the fetal cellular DNA using methods described herein or known in the art. See block 1006. In some embodiments, process 1000 applies Tn5 transposase-mediated transposon tagging to create a second indexed sequencing library from the fetal cellular DNA. See block 1008. In some embodiments, the index sequence for the sequencing library may be incorporated by alternative methods as described elsewhere herein or known in the art. An example using a site selective extension primer to incorporate the index sequence is described below.

Figure 11:
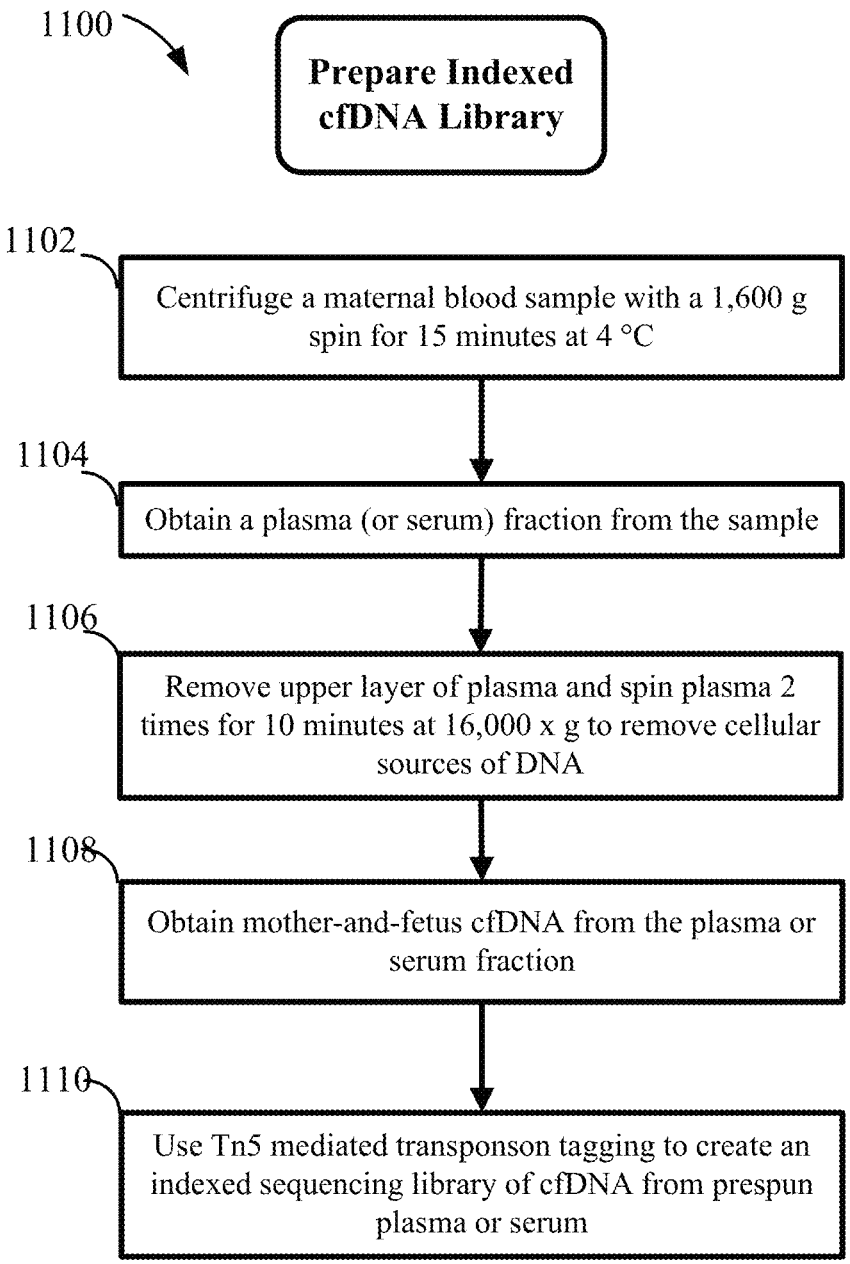
FIG. 11 is a flowchart showing a process for preparing an indexed library using mother-and-fetus cfDNA.

In some embodiments, the method for determining a sequence of interest for the fetus involves preparing an indexed library using the cfDNA obtained from a maternal blood sample. The sequencing library of the cfDNA has a different index than the library of the fetal cellular DNA. FIG. 11 is a flowchart showing a process 1100 for preparing an indexed library of cfDNA, including steps for obtaining the cfDNA from a maternal blood sample, which blood sample may also provide fetal cellular DNA in some embodiments. Process 1100 starts by centrifuging a maternal blood sample with a low-speed spin for 15 min. at 4° C. The centrifugation may be performed and 16,000 g. See block 1102. The centrifugation separates the blood sample into a plasma fraction, a buffy coat fraction, and an erythrocyte fraction. The process proceeds by obtaining the plasma or serum from the sample. See block 1104. The process further involves removing the upper layer of plasma, and spinning the plasma twice for 10 min. at 16,000 g to remove cellular sources of DNA, which are larger in size than cfDNA and are pelleted by the high-speed centrifugation. See block 606. The process then proceeds by obtaining mother-and-fetus cfDNA from the plasma or serum fraction using methods described herein or known in the art. See block 1108. In some embodiments, process 1100 applies Tn5 mediated transposon tagging to create an indexed sequencing library from the cfDNA. See block 1110. In the preferred embodiments, the sequencing library of the cfDNA has a different index sequence from that of the fetal cellular DNA library. In some embodiments, the index sequence for the sequencing library may be incorporated by alternative methods such as the method shown in FIG. 12.

Example Workflow for Preparing Sequence libraries

Various methods may be used to prepare libraries indexed separately for mother-and-fetus cfDNA and fetal cellular DNA. Plasma cfDNA from a pregnant woman is a mixture comprising mostly of mother DNA with a certain fraction of fetal DNA. An accurate and precise determination of the % fetal DNA in maternal plasma cfDNA is desirable in non-invasive prenatal testing, especially for samples with low fetal fractions. One commonly used method for determining fetal fraction interrogates a plurality of high heterozygocity SNPs and studies allelic frequency differences between mother and fetus. Data analysis can be challenging when one studies SNPs only in cfDNA, since "true" genotype of the mother alone or the fetus alone is not known. Some embodiments disclosed herein provide a means to determine the fetal zygosity genotype of the fetus, at least for some SNPs that are detectable from the relatively rare fetal NRBCs.

Figure 12:
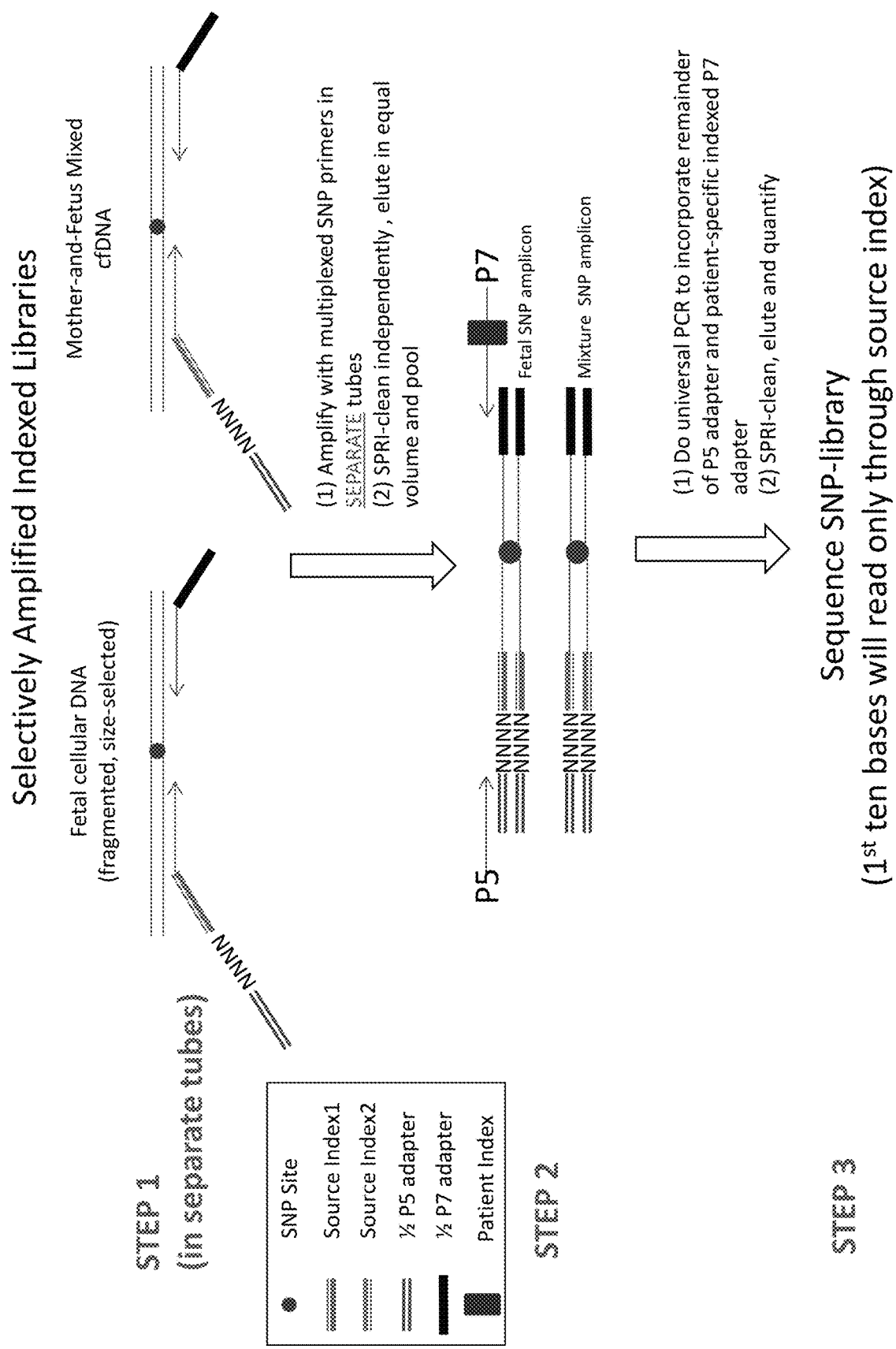
FIG. 12 shows a diagram of a workflow according to some embodiments of the invention, wherein the incorporation of index sequences occur with two primers introducing two adaptor segments.

FIG. 12 shows a diagram of a workflow according to some embodiments of the invention, wherein the incorporation of index sequences occur with two primers introducing two adaptor segments. This workflow presents an alternative to the workflow of using Tn5 transposase-mediated transposon tagging to incorporate indexes, such as those depicted in FIGS. 10 and 11. FIG. 12 presents a workflow where the cellular and cell-free DNAs are indexed independently during an early PCR step that also interrogates a plurality of SNP-sites in a multiplexed manner. The indexing at this stage is called "source index" since it differentiates between fetal cellular DNA and the mixed cfDNA within the same patient sample.

As shown in FIG. 12, the source index 1 sequence is incorporated into the fetal cellular DNA, and the source index 2 is incorporated into the cfDNA, when the cellular DNA and the cfDNA are processed separately. In this indexing stage, two primers are applied, both targeting the SNP of interest diagram, which is shown as a dot at the center of the two sequences. The primers to the left of the SNP include a sequence index as well as about one half of a paired end adaptor (e.g., the P5 adaptor for the Illumina sequencing platform). Only about half of a sequencing adaptor is introduced by the primer to avoid a long overhang, which could dehybridize too easily. The remaining portion of the adaptor is introduced at later processing stages. The primers to the right of the SNP in the depicted example include about one half of second paired end adaptor (e.g., a P7 adaptor for the Illumina sequencing platform). The P5 and P7 adaptors allow library fragments to anneal to their complementary oligos on the flowcell surface of the Illumina sequencer, which adaptors are necessary to perform bridge amplification and clustering.

One option to consider at the indexing stage is to keep the number of amplification cycles minimal, so as to minimize or avoid introduction of bias between the two samples. In the depicted workflow, amplicons are independently cleaned using Solid Phase Reversible Immobilisation (SPRI), then eluted in equal volume and pooled. The amplicons are then mixed together and then subjected to universal PCR at the same time in a single tube. The universal PCR introduces a second index at the P7 end, which second index can be used to multiplex patient samples during sequencing. During the universal PCR, P5 and P7 adaptors are extended to full length. By the end of PCR, library fragments are prepared to include all sequences necessary for multiplexed sequencing. Library fragments are then SPRI-cleaned and ready for sequencing.

Since each kind of DNA from the same patient sample is source-indexed uniquely, the downstream data from a given patient can be identified as arising from fetal cellular DNA or from the mixed mother-fetus cfDNA.

In conventional methods using only cfDNA, only those SNPs for which the mother is homozygous and the fetus is heterozygous constitute "informative SNPs." SNPs where the mother may be heterozygous and the fetus is homozygous are not easily used without understanding the inherent "noise" in the heterozygous calls for the mother. By genotyping fetal cellular DNA, the zygosity of a fetus may be obtained using data from the fetal cellular DNA. This zygosity can help to determine fetal fraction (FF) of cfDNA using both "informative" and "uninformative" data. The fetal fraction determined this way has higher confidence interval than methods using cfDNA alone. Furthermore, this more accurate measure of FF allows for better estimate of CNV.

Samples

Samples that are used for determining one or more sequences of interest can include samples taken from any cell, tissue, or organ. In some embodiments, samples are used to determine the presence, abundance, copy number or copy number variation of a sequence of interest. In some embodiments, the samples contain nucleic acids that are that are present in cells and/or nucleic acids that are "cell-free" (e.g., cfDNA). In some embodiments, the nucleic acids contain cellular DNA of the mother only and cfDNA of both the mother and the fetus carried by the mother. In some embodiments, the mother-only cellular DNA is obtained from a buffy coat component of a blood sample of the mother, the cellular DNA being from maternal white blood cells or leukocytes. In some embodiments, the mother-and-fetus mixed cfDNA is obtained from a plasma component of a blood sample of the mother.

In some embodiments, the mother-only cellular DNA and the mixed cfDNA are first processed separately to incorporate different index sequences, thereby providing an indicator of the source of the nucleic acids. The indexed nucleic acids are then combined for further processing. In some embodiments, similar quantities of cellular DNA and cfDNA are combined.

Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind.; Qiagen, Valencia, Calif.; or Macherey-Nagel, Duren, Del.). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the cfDNA present in the sample can be enriched specifically or non-specifically prior to use (e.g., prior to preparing a sequencing library). Specific enrichment of sample DNA refers to amplification of specific sequences contained in the sample, e.g. polymorphic sequences or sites. Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that contain more than one genome. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above. In some embodiments, the nucleic acid(s) to be screened for one or more sequence of interest is purified or isolated by any of a number of well-known methods.

Accordingly, in certain embodiments the sample contains a purified or isolated polynucleotide, or it can contain samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential genetic diseases or chromosomal abnormalities in the fetus. The maternal sample can be a tissue sample, a biological fluid sample, or a cell sample.

In another illustrative, but non-limiting embodiment, the maternal sample is a mixture of two or more biological samples, e.g., the biological sample can comprise two or more of a biological fluid sample, a tissue sample, and a cell culture sample. In some embodiments, the sample is a sample that is easily obtainable by non-invasive procedures, e.g., blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, as achieved, for example, using mechanical shearing, or it can be sequence-specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from cfDNA, which is not subjected to fragmentation in vitro.

In some illustrative embodiments, the sample nucleic acid(s) are obtained as genomic DNA, which is subjected to fragmentation into fragments of approximately 150 or more, approximately 300 or more, approximately 400 or more, or approximately 500 or more base pairs, and to which NGS methods can be readily applied.

Determine Fetal Zygosity and Fetal Fraction

In some embodiments, the sequence information obtained from mother-only cellular DNA and mother-fetus mixed cfDNA are used to determine fetal zygosity or fetal fraction. In some embodiments, the method may detect that the fetus has a genetic disorder by determining that the fetus is homozygous of a disease causing allele of a disease related gene wherein the mother is heterozygous of the allele.

In certain implementations described herein, methods are provided for determining fetal fraction of maternal DNA using multiple DNA sequence readings at sequence sites known to harbor one or more polymorphisms. Typically, though not necessarily, such polymorphisms are single nucleotide polymorphisms (SNP). Other types of suitable polymorphisms include deletions, STRs (Short Tandem Repeats), insertions, indels (including microindels), etc. In certain embodiments, the polymorphism sites are found on a "reference sequence" as described below. In some embodiments, the polymorphism sites are discovered while aligning sequence tags to one another and/or a reference sequence.

Certain disclosed methods make use of the fact that a fetus's DNA sequences at the polymorphism sites under consideration may not correspond to those of its mother. For example, the mother's DNA at the site of a particular SNP may be homozygous, while the fetus's version of the SNP will be heterozygous. Hence, a collection of sequence samples taken for the SNP in question will be heterogeneous with the majority of the sequences containing the major allele and the remaining fraction containing the minor allele. The relative amounts of the major and minor alleles are determined by the fraction of fetal DNA in the sample.

It should be mentioned that in a homozygous sample both copies of a given SNP or other polymorphism contain the same allele, while a heterozygous SNP or other polymorphism contains one copy of the major allele and one copy of the minor allele. One knows, therefore, that DNA taken exclusively from a heterozygous individual should contain 50% of the major allele and 50% of the minor allele. This knowledge can be used in elucidating the fraction of fetal DNA.

In some implementations, the DNA taken from the mother's blood is read many times, with the total number of reads mapping to a particular site of a polymorphism being deemed the "coverage" of the polymorphism, and the number of reads mapping to the minor allele for that polymorphism being deemed the minor allele count. The ratio of minor allele count to coverage is useful for determining fetal fraction in various implementations.

Table 1 shows hypothetical data that can be obtained using the processes introduced herein. The data assumes the following: (1) 10% fetal fraction, (2) measured maternal genomic DNA yields a 48% reading of b allele in heterozygous mothers, (3) maternal and fetal cfDNA have the same % as the corresponding maternal genomic DNAs, and (4) maternal genomic DNA yields 100% or 0% reading of b allele in homozygous mother (b and a respectively). Table 1 below shows the fraction of allele b for the hypothetical data that can be obtained from training sequences. While one might expect that the cellular DNA sample would give a 50% reading for allele b in the heterozygous case, this is not often the case. Biases introduced in the amplification and sequence techniques frequently cause the reading to vary from 50%. Such biases may be addressed by using a training set of polymorphisms and data from cellular DNA.

TABLE 1

Fraction of allele b for training sequences

| Training SNP | Mat. genomic DNA | mixed cfDNA (measured) | mixed cfDNA (actual) | Zygosity case Mother fetus |
|---|---|---|---|---|
| 1. | 48% | 48% | 50% | Heterozygous Heterozygous |
| 2. | 48% | 48(0.9) + 100(0.1) = 53.2% | 50(0.9) + 100(.1) = 55% | Heterozygous Heterozygous b |
| 3. | 100% | 100(0.9) + 48(0.1) = 94.8% | 100(0.9) + 50(0.1) = 95% | Heterozygous b Heterozygous |
| 4. | 100% | 100% | 100% | Heterozygous b Heterozygous b |
| 5. | 0% | 0(0.9) + (48)(0.1) = 4.8% | 0(0.9) + (50)(0.1) = 5% | Heterozygous a Heterozygous |
| 6. | 0% | 0% | 0% | Heterozygous a Heterozygous a |

In some embodiments, the method de-convolves the sequencing data based on indices, trained data analysis on the targeted control sites and deduce fetal zygosity for a disease causing alleles. In some embodiments, the zygosity case is determined by comparing the relative amounts of each of two alleles in cellular DNA and in cfDNA for the sequence of interest and training sequences. In some implementations, the training sequences may be any sequences with ascertainable zygosity, such as sequences in the sex chromosomes or other sequences having polymorphisms whose zygosity cases correlate with observable phenotypes. In some embodiments, the zygosity case for the fetus is determined by comparing the relative amounts of DNA mapping to two or more alleles. In general, neither the fetal fraction of the cfDNA nor the zygosity cases of the sequence of interest and the training set sequences are known at the beginning of the method. This information may be determined by modeling the training set zygosities and fetal fraction and determining which set of zygosities and fetal fraction best fit the data. Various techniques may be employed for this purpose. For example, a mixture model may be employed to determine a mean and optionally the variance for each of the four zygosity cases encountered in the training set. In specific embodiments, this is the mean and variance associated with the frequency of the minor allele in relation to the total number of counts for a polymorphism under consideration (coverage). The mean values for certain zygosity cases are directly related to the fetal fraction in the cfDNA. The application of mixture models to a training set of polymorphisms and thereby determine fetal fraction is described in U.S. patent application Ser. No. 13/445,778, [ARTEP002US] filed Apr. 12, 2012, which is incorporated herein by reference in its entirety.

Figure 13:
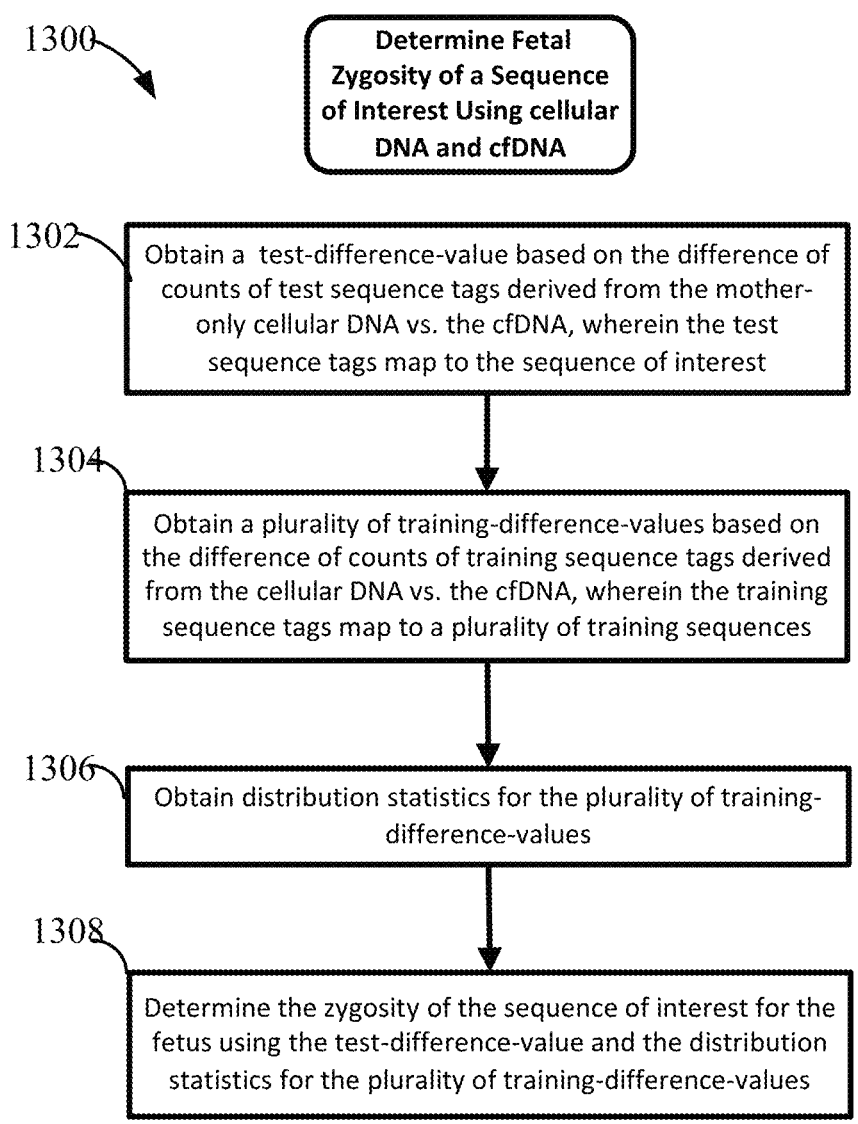
FIG. 13 shows a process for determine fetal zygosity of a sequence of interest using mother-only cellular DNA and mother-and-fetus cfDNA.

FIG. 13 shows a process for determining fetal zygosity of a sequence of interest using cellular DNA and cfDNA. This process may be used to determine the fetus zygosity when the mother is heterozygous, which is difficult with conventional method because the major allele and minor allele have similar counts in the cfDNA. The method uses cellular DNA and cfDNA sequence data obtained from two sequencing libraries processed together, which equalizes processing bias between two sequencing libraries for the cellular DNA and cfDNA. The two libraries include different indexes to identify the source of the genetic materials. This allows for comparison of data from the two libraries, which helps to improve discrimination power between the fetus zygosity when the mother is heterozygous.

In some embodiments, the sequencing libraries are processed starting with substantially the same or similar size and concentration cellular DNA and cfDNA in separate reaction environments, e.g., test tubes. This allows comparison of sequence tags from cellular DNA and cfDNA. In some embodiments this allows the subtraction of sequence tags obtained from the two libraries. In some embodiments, wild-type and mutant regions of disease related gene(s) are enriched using probes that target both alleles of disease related gene(s) and have different indices for cellular DNA and cfDNA, the indices are incorporated into the targeted sequences in the separate reaction environment (e.g., separate tubes). Then the cellular DNA and cfDNA with enriched targeted regions are mixed together and amplified using universal PCR primers. The amplified product will be sequencing-ready targeted libraries of both cellular DNA for the mother and cfDNA for the mother and fetus. The sequencing results may then be used to determine the zygosity of the fetus and/or fetal fraction of the cfDNA.

In some embodiments, process 1300 for determining fetal zygosity involves obtaining a test-difference-value based on the difference of counts of test sequence tags derived from the mother-only cellular DNA vs. the cfDNA for each of or at least one of the two alleles, where the test sequence tags map to the sequence of interest. See block 1302. In various embodiments, the test-difference-value may be obtained by subtraction, division, or other operations that reflect the difference of sequence tag counts. In some embodiments, the test-difference-value may be normalized.

In some embodiments, process 1300 also involves obtaining a plurality of training-difference-values based on the difference of counts of training sequence tags derived from the cellular DNA vs. the cfDNA, wherein the training sequence tags map to a plurality of training sequences. In some implementations, the training sequences may be any sequences with ascertainable zygosity, such as sequences in the sex chromosomes or other sequences having polymorphisms whose zygosity cases correlate with observable phenotypes. See block 1304. In some embodiments, sequencing library preparation allows the acquisition of the plurality of training sequence tags. In some embodiments, library preparation comprises amplifying a plurality of training sequences before sequencing the combined sample. In some embodiments, the plurality of training sequences comprises more than 10, 50, 60, 100, 500, 1000, or 5000 sequences. Similar to the test-difference-value, the training-difference-values may also be obtained by different operations and or normalized.

In some embodiments, process 1300 also involves obtaining distribution statistics for the plurality of training-difference-values. See block 1306. In some embodiments, the distribution statistics include a mixture model that describes the data as having two or more separate underlying distributions, each distribution corresponding to data associated with a zygosity case. In some embodiments, the distribution statistics include the central tendency (e.g., mean) and spread (e.g., standard deviation) of two or more underlying distributions.

In some embodiments, process 1300 also involves determining the zygosity of the sequence of interest for the fetus using the test-difference-value and the distribution statistics for the plurality of training-difference-values. See block 1308. In some embodiments, for instance, if the test-difference-value falls within 1, 2, or 3 standard deviations of the mean of one distribution that corresponding to a fetal/maternal zygosity case, it is determined that the sequence of interest has such a zygosity case. Other criteria may be used, which can be adjusted according to the empirical information obtained for the distribution.

In some embodiments, instead of, or in addition to, examining the difference value for one allele of a bi-allelic gene, the method examines the difference value for two alleles. The method involves obtaining a difference of the difference value between two alleles. This difference value between two alleles is obtained for the sequence of interest and the plurality of training sequences. The method also involves obtaining the distribution statistics for the difference value between the two alleles for the training sequence, which is then used to determine whether the sequence of interest belongs to a distribution corresponding to a zygosity case as described above.

Figure 14A:
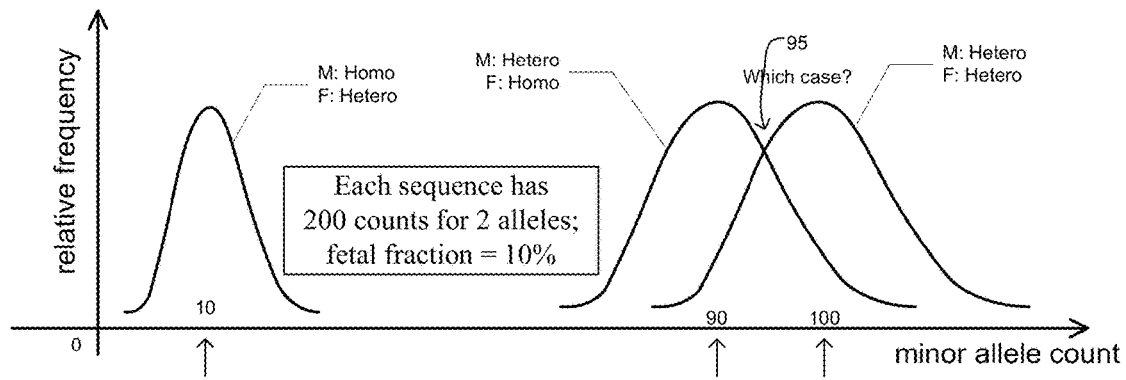
FIGS. 14A-14D illustrates a hypothetical example of some embodiments involving analyses of mother-only cellular DNA and mother-and-fetus cfDNA and a comparison to a conventional method.

FIGS. 14A-14D illustrates a hypothetical example of the advantages of some embodiments involving analyses of mother-only cellular DNA over conventional method. FIG. 14A shows the distributions of minor allele counts for three different zygosity cases: mother homozygous and fetus heterozygous (case 2), mother heterozygous and fetus homozygous (case 3), and mother heterozygous and fetus heterozygous (case 4). The distribution for the zygosity case that both mother and fetus are homozygous (case 1) is omitted because the minor allele should be absent. It is difficult to differentiate cases 3 and 4 using conventional methods, which discrimination is particularly important to determine if the fetus is homozygous when the mother is a carrier of a disease related gene.

FIG. 14A shows hypothetical distributions of minor allele counts for multiple sequences, each sequence having two alleles and a total of 200 sequence tags for the two alleles. The hypothetical data assumes a fetal fraction of 10%. For sequences in the mother heterozygous and fetus homozygous case (case 3), the expected mean of the minor allele count is 90. For sequences in the mother heterozygous and fetus heterozygous case (case 4), the expected mean of the minor allele count is 100. Because the large spread and the small separation of the two distributions, for a test sequence with a 95 minor allele count it is difficult or impossible to determine if the sequence belongs to one or the other zygosity case. As such, some conventional methods consider both zygosity cases "uninformative" for determining zygosity case. Such method can only use data from the mother homozygous and fetus heterozygous case (case 2) to determine zygosity of the sequence. Fetal fraction (FF) may be calculated after the zygosity case is determined as FF=2A/D for case 2, wherein A is the minor allele count, and D is the total allele counts.

Some conventional methods used both cellular DNA and cfDNA to determine fetal sequences. For instance, Bischoff et al. compared the efficacy of assays using fetal cellular DNA and cfDNA for non-invasive prenatal screening, and found that the cfDNA assay was at least four times more sensitive. Bischoff et al. (2002), Human Reproduction Update, Vol. 8, No. 6, pp. 439-500. Bischoff et al. thus concluded: "Cell-free fetal DNA may be a more robust approach than intact cell analysis." Moreover, Bischoff found no correction between the frequency of detecting fetal cellular DNA and the concentration of cfDNA. The lack of correlation argues against combining cellular DNA and cfDNA assays. As such, conventional methods did not provide means to combine both cellular DNA and cfDNA to achieve sensitivity and specificity even higher than using cfDNA alone, or address case 3 above that is difficult to resolve using conventional cfDNA methods. Some implementations described below combine both cellular DNA and cfDNA to achieve advantages over conventional methods using cfDNA alone.

Some embodiments, such as method 1300, use the maternal cellular DNA to factor out the noise in the cfDNA, thereby increasing the power to discriminate case 3 from case 4. Using the hypothetical data of Table 1, also assuming 200 sequence tags for each training sequence, one may deduce the cellular DNA and cfDNA allele counts for both alleles for heterozygous mother and homozygous fetus (case 3) and heterozygous mother and heterozygous fetus (case 4). Although the hypothetical examples illustrated here involve maternal cellular DNA, The processes disclosed here may also be applied using fetal cellular DNA.

TABLE 2

Allele counts for allele a and b for case 3 (mother heterozygous and fetus homozygous)

| | Cellular DNA (maternal) | cfDNA (mixed) | Difference values |
|---|---|---|---|
| Allele a (minor) | 104 | 95.6 | $\Delta a = -9.4$ (cfDNA − cellular DNA) |
| Allele b (major) | 96 | 106.4 | $\Delta b = 10.4$ (cfDNA − cellular DNA) |
| | | | $\Delta b - \Delta a = 19.8$ |

TABLE 3

Allele counts for allele a and b for case 4 (mother and fetus heterozygous)

| | Cellular DNA (maternal) | cfDNA (mixed) | Difference values |
|---|---|---|---|
| Allele a | 104 | 104 | $\Delta a = 0$ (cfDNA − cellular DNA) |
| Allele b | 96 | 96 | $\Delta b = 0$ (cfDNA − cellular DNA) |
| | | | $\Delta b - \Delta a = 0$ |

Some embodiments, such as method 1300, use the maternal cellular DNA to factor out the empirical noise in the cfDNA, thereby increasing the power to discriminate case 3 from case 4. Using the hypothetical data of Table 1, also assuming 200 sequence tags for each training sequence, one can deduce the cellular DNA and cfDNA allele counts for both alleles for heterozygous mother and homozygous fetus (case 3) and heterozygous mother and heterozygous fetus (case 4).

Because the difference of allele counts cfDNA—cellular DNA is obtained from sequencing libraries having the same empirical and processing conditions, it is expected that the variation common to both cfDNA and cellular DNA is removed by the subtraction (or other operations that indicate the difference between the two libraries). This expectation, however, does not limit or determine the utility or patentability of the method disclosed herein.

In some embodiments, the method involves obtaining the difference by subtracting the sequence tag counts (or normalized counts) between the cfDNA versus the cellular DNA. Table 2 shows the difference value by subtraction for case 3 data. $\Delta a$ shows the difference value for allele a (minor allele), $\Delta b$ shows the difference value for allele b (major allele), and $\Delta b - \Delta a$ shows the difference between $\Delta b$ and $\Delta a$. Similarly, Table 3 shows the difference value by subtraction for case 4 data. In this example, only data from case 3 and case 4 are shown because these two cases present challenge to conventional methods. In fact, the embodiments disclosed herein are also applicable to case 2 data.

Figure 14B:
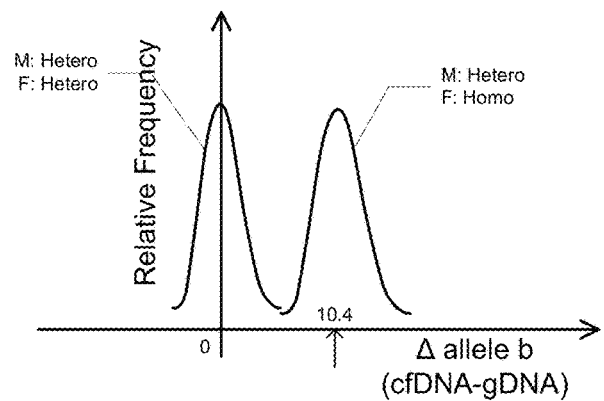
Figure 14C:
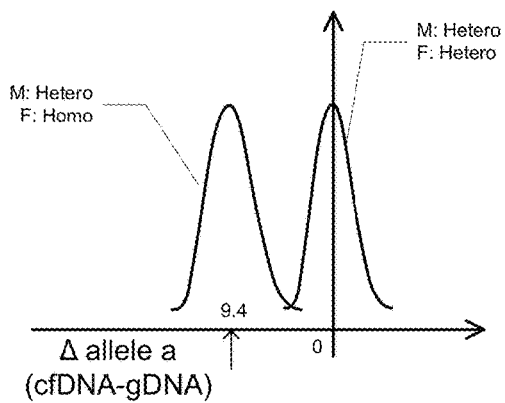
Figure 14D:
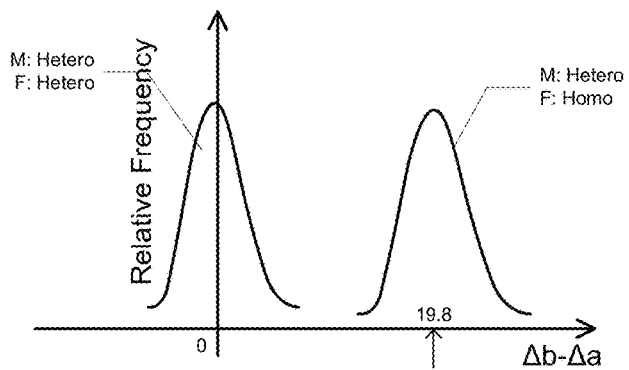

FIGS. 14B-14C show the hypothetical distribution to the hypothetical data. FIG. 14B shows the distributions for $\Delta b$ for case 3 and case 4. FIG. 14C shows the distributions for $\Delta a$ for case 3 and case 4. FIG. 14D shows the distributions for $\Delta b - \Delta a$ for case 3 and case 4. Because the subtraction of cellular DNA (labeled as gDNA in the figures) from the cfDNA removes empirical noise from the data, the spread of the distributions are smaller as compared to the spread of the distribution of the minor allele count shown in FIG. 14A. This allows discrimination between the two distributions for the case 3 and case 4. Using a method disclosed herein, one may obtain distribution statistics of $\Delta a$, $\Delta b$, and $\Delta b - \Delta a$ for training sequences. Using the distribution statistics and the difference value for a sequence of interest, as disclosed above, one can determine whether the sequence of interest belongs to case 3 or 4. Therefore, methods disclosed herein allow one to determine if a fetus is homozygous or heterozygous when the mother is heterozygous. Given a zygosity case, one may calculate fetal fraction (FF) using the allele counts, such as determining FF=1-2A/D for case 3, wherein A is the minor allele count and D is the total count. Other methods known in the art also may be used to calculate fetal fraction. In some embodiments, this calculation may adjust for the estimate of fetal fraction by considering the empirical bias observed in the maternal cellular DNA In a conventional method using only cfDNA, the zygosity of the fetus is unknown. Therefore, only those SNPs for which the mother is homozygous and the fetus is heterozygous constitute "informative SNPs." In this case, fetal fraction (FF) may be calculated as FF=2A/D, wherein A is the minor allele count, and D is the total allele counts.

In a conventional method using only cfDNA, SNPs where the mother may be heterozygous and the fetus is homozygous are not easily used without understanding the inherent "noise" in the heterozygous calls for the mother. This is so because the minor allele frequency for mother-hetero-fetus-homo zygosity case (case 3 above) is similar to that for mother-hetero-fetus-hetero case (case 4 above), both of which were considered "uninformative" for determining FF.

In some embodiments involving analysis of fetal cellular DNA, by genotyping fetal cellular DNA, the zygosity of a fetus may be obtained using data from fetal cellular DNA. This zygosity can help to determine fetal fraction (FF) of cfDNA using both "informative" and "uninformative" data. Fetal fraction may be calculated for mother-hetero-fetus-homo zygosity case as FF=1-2A/D, wherein A is the minor allele count, and D is the total allele counts. The zygosity case is ascertained by fetal zygosity determined from fetal cellular DNA and maternal zygosity determined from allele frequencies of cfDNA. Therefore, some embodiments provide methods to obtain FF with high accuracy by availing more data for the calculation.

Furthermore, this measure of FF allows a good estimate of CNV. If the FF of a particular sequence differs significantly from the normal FF, CNV may be inferred for the sequence. For instance, if the fetal fraction is 10%, when the mother is homozygous, and fetus heterozygous, then the minor allele frequency is expected to be 5%. However, if the fetus has an extra copy of the sequence, then the minor allele frequency will be 10%, which may be determined as significantly different from the expected 5%.

The expected minor allele frequency may be obtained from training sequences obtained from the same sample, which training sequences are different from the sequence of interest being tested. Therefore, some embodiments of the disclosure involve processing and analyzing a plurality of training sequences. In some embodiments, the cellular DNA and cfDNA are enriched for training sequences or sites. In some embodiments, more than about 10, 50, 60, 100, 500, 1000, or 5000 SNP sites are used as training sites to understand distribution counts of SNPs sequence tags in the assay where the mother is heterozygous and the fetus is homozygous. In some embodiments, when a sequence of interest has a minor allele frequency different from the training sequence by a criterion, a CNV call is determined.

The CNV call uses a first sequence from the fetal cellular DNA to determine the zygosity of the fetus. The fetal cfDNA may also provide the CNV for the first sequence. However, the same method may also be applied to obtain the CNV for a second sequence, which may not be available from the fetal cellular DNA due to the scarcity of the fetal cellular DNA. Therefore, the disclosed methods combining cellular DNA and cfDNA provide an advantage relative to using cellular DNA alone.

Evaluating Copy Number Variation (CNV)

Particularly useful methods for evaluating CNV using mother-and-fetus cfDNA are further described below. Some embodiments of this disclosure provide methods using both mother cellular DNA and mother-and-fetus cfDNA for validation of the CNV obtained from cfDNA alone, boosting the confidence of CNV evaluation. Some embodiments use both fetus cellular DNA and mother-and-fetus cfDNA, for example, as a mixture in multiplex detection formats, to evaluate CNV. Some embodiments provide methods for directly calculating CNV using both cellular DNA and cfDNA.

Using sequence coverage values for mother-and-fetus cfDNAs, e.g., according to the methods described below, one can determine copy number and CNV of sequences, chromosomes, or chromosome segments. In some embodiments, the method for determining the presence or absence of any complete fetal chromosomal aneuploidies using cfDNA from a maternal test sample comprises (a) obtaining sequence information for fetal and maternal nucleic acids in the maternal test sample; (b) using the sequence information and the method described herein to identify a number of sequence tags or sequence coverage quantity derived therefrom for each of the chromosomes of interest selected from chromosomes 1-22, X and Y and to identify a number of sequence tags for one or more normalizing chromosome sequences; (c) using the number of sequence tags identified for each of the chromosomes of interest and the number of sequence tags identified for each of the normalizing chromosomes to calculate a single chromosome dose for each of the chromosomes of interests; and (d) comparing each chromosome dose to a threshold value, and thereby determining the presence or absence of any complete fetal chromosomal aneuploidies in the maternal test sample.

In some embodiments, step (a) described above can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing chromosome sequence(s), where a normalizing sequence is a robust chromosome that is unlikely to be aneuploid. In some other embodiments, chromosome dose is based on processed sequence coverage quantities derived from the number of sequence tags. In some embodiments, only unique, non-redundant sequence tags are used to calculate the processed sequence coverage quantities. In some embodiments, the processed sequence coverage quantity is a sequence tag density ratio, which is the number of sequence tags standardized by sequence length. In some embodiments, the processed sequence coverage quantity is a normalized sequence tag, which is the number of sequence tags of a sequence of interest divided by all or a substantial portion of the genome.

In some embodiments, a chromosome dose is calculated as the ratio of the processed sequence coverage quantities for each of the chromosomes of interest and processed sequence coverage quantities for the normalizing chromosome sequence(s).

In any one of the embodiments above, one or more steps of the method are repeated for test samples from different maternal subjects. In any one of the embodiments above, the method can further comprise calculating a normalized chromosome value (NCV), wherein the NCV relates the chromosome dose to the mean of the corresponding chromosome dose in a set of qualified samples as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In some embodiments, NCV can be calculated "on the fly" by relating the chromosome dose of a chromosome of interest in a test sample to the median of the corresponding chromosome dose in multiplexed samples sequenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_i$ is the observed j-th chromosome dose for test sample i. In this embodiment, test sample i is one of the multiplexed samples sequenced on the same flow cell from which $M_j$ is determined.

In some embodiments, a method is provided for determining the presence or absence of different partial fetal chromosomal aneuploidies in a maternal test sample comprising fetal and maternal nucleic acids. The method involves procedures analogous to the method for detecting complete aneuploidy as outlined above. However, instead of analyzing a complete chromosome, a segment of a chromosome is analyzed. Accordingly, instead of a NCV, a normalized segment value (NSV) is obtained for evaluation of the chromosome segment. See US Patent Application Publication No. 2013/0029852, and U.S. Patent Application No. 61/893,830, which are incorporated by reference.

In some embodiments, the determination of CNV comprises calculating a NCV or NSV that relates the chromosome or segment dose to the mean of the corresponding chromosome or segment dose in a set of qualified samples as described above. Then CNV can be determined by comparing the NCV/NSV to a predetermined copy number evaluatiom threshold value.

In some embodiments, the FF for a chromosome can be calculated according to the following equation.

$$FF_{ij} = 2 \times \left| \frac{NCV_{ij} \times \hat{\sigma}_j}{\hat{\mu}_j} \right| = 2 \times NCV \times CV$$

Namely, for every NCV of a chromosome of interest, an expected fetal fraction associated with the given NCV value can be calculated from the CV based on the mean and standard deviation of the chromosome ratio for the chromosome of interest across a population of unaffected samples.

Some embodiments of the disclosure provide a method for validating the NCV obtained using only cfDNA. For instance, a plurality of estimates of FF from various zygosity cases obtained using both mixed cfDNA and maternal cellular DNA as described elsewhere herein may be combined to obtain distribution statistics of FF. Then the FF obtained using only cfDNA can be compared to the FF distribution using both cfDNA and cellular DNA. If the FF obtained with cfDNA falls outside a decision criterion, the NCV obtained using cfDNA only may need to be retested for experimental error or mosaicism.

Some embodiments of the disclosure provide methods for directly determining CNV using both cfDNA and maternal cellular DNA, which CNV estimate has a higher sensitivity and lower noise than using cfDNA alone. In these embodiments, the methods take advantage of the FF obtained using both the cellular DNA and cfDNA as described above to reduce noise in the estimate. In some embodiments, a chromosome dose of sequence j is calculated as:

$$x_j = m_j - \text{average}(n_i) \times (1 - FF)$$

wherein $m_j$ is a standardized coverage of sequence j standardized by sequence length obtained using cfDNA data, $n_i$ is a standardized coverage of a normalizing sequence i using cfDNA data, and FF is the fetal fraction obtained using both cellular DNA and cfDNA as described above. This chromosome dose of sequence j has the maternal DNA coverage subtracted from the data. Then NCV may be calculated as described as described above:

$$NCV_{ij} = \frac{x_{ij} - \hat{\mu}_j}{\hat{\sigma}_j}$$

Here $\hat{\mu}_j$ is the chromosome dose for control pregnant women for sequence j calculated in the same way as $x_j$. The chromosome dose of sequence j in this method has the maternal DNA coverage subtracted from the data, thereby decreasing the baseline of comparison and increasing the signal to noise ratio of the NCV estimate. Then a CNV call may be based on this more accurate NCV compared to method using cfDNA only. Other embodiments may use different methods to combine the data from both cfDNA and cellular DNA to improve the signal and reduce the noise for CNV calls.

Marker Nucleic Acids for Tracking and Verifying Sample Integrity

In various embodiments verification of the integrity of the samples and sample tracking can be accomplished by sequencing mixtures of sample genomic nucleic acids, e.g., cfDNA, and accompanying marker nucleic acids that have been introduced into the samples, e.g., prior to processing.

Marker nucleic acids can be combined with the test sample (e.g., biological source sample) and subjected to processes that include, for example, one or more of the steps of fractionating the biological source sample, e.g., obtaining an essentially cell-free plasma fraction from a whole blood sample, purifying nucleic acids from a fractionated, e.g., plasma, or unfractionated biological source sample, e.g., a tissue sample, and sequencing. In some embodiments, sequencing comprises preparing a sequencing library. The sequence or combination of sequences of the marker molecules that are combined with a source sample is chosen to be unique to the source sample. In some embodiments, the unique marker molecules in a sample all have the same sequence. In other embodiments, the unique marker molecules in a sample are a plurality of sequences, e.g., a combination of two, three, four, five, six, seven, eight, nine, ten, fifteen, twenty, or more different sequences.

In one embodiment, the integrity of a sample can be verified using a plurality of marker nucleic acid molecules having identical sequences. Alternatively, the identity of a sample can be verified using a plurality of marker nucleic acid molecules that have at least two, at least three, at least four, at least five, at least six, at least seven, at least eight, at least nine, at least ten, at least 11, at least 12, at least 13, at least 14, at least 15, at least 16, at least 17m, at least 18, at least 19, at least 20, at least 25, at least 30, at least 35, at least 40, at least 50, or more different sequences. Verification of the integrity of the plurality of biological samples, i.e., two or more biological samples, requires that each of the two or more samples be marked with marker nucleic acids that have sequences that are unique to each of the plurality of test sample that is being marked. For example, a first sample can be marked with a marker nucleic acid having sequence A, and a second sample can be marked with a marker nucleic acid having sequence B. Alternatively, a first sample can be marked with marker nucleic acid molecules all having sequence A, and a second sample can be marked with a mixture of sequences B and C, wherein sequences A, B and C are marker molecules having different sequences.

The marker nucleic acid(s) can be added to the sample at any stage of sample preparation that occurs prior to library preparation (if libraries are to be prepared) and sequencing. In one embodiment, marker molecules can be combined with an unprocessed source sample. For example, the marker nucleic acid can be provided in a collection tube that is used to collect a blood sample. Alternatively, the marker nucleic acids can be added to the blood sample following the blood draw. In one embodiment, the marker nucleic acid is added to the vessel that is used to collect a biological fluid sample, e.g., the marker nucleic acid(s) are added to a blood collection tube that is used to collect a blood sample. In another embodiment, the marker nucleic acid(s) are added to a fraction of the biological fluid sample. For example, the marker nucleic acid is added to the plasma and/or serum fraction of a blood sample, e.g., a maternal plasma sample. In yet another embodiment, the marker molecules are added to a purified sample, e.g., a sample of nucleic acids that have been purified from a biological sample. For example, the marker nucleic acid is added to a sample of purified maternal and fetal cfDNA. Similarly, the marker nucleic acids can be added to a biopsy specimen prior to processing the specimen. In some embodiments, the marker nucleic acids can be combined with a carrier that delivers the marker molecules into the cells of the biological sample. Cell-delivery carriers include pH-sensitive and cationic liposomes.

In various embodiments, the marker molecules have antigenomic sequences, that are sequences that are absent from the genome of the biological source sample. In an exemplary embodiment, the marker molecules that are used to verify the integrity of a human biological source sample have sequences that are absent from the human genome. In an alternative embodiment, the marker molecules have sequences that are absent from the source sample and from any one or more other known genomes. For example, the marker molecules that are used to verify the integrity of a human biological source sample have sequences that are absent from the human genome and from the mouse genome. The alternative allows for verifying the integrity of a test sample that comprises two or more genomes. For example, the integrity of a human cell-free DNA sample obtained from a subject affected by a pathogen, e.g., a bacterium, can be verified using marker molecules having sequences that are absent from both the human genome and the genome of the affecting bacterium. Sequences of genomes of numerous pathogens, e.g., bacteria, viruses, yeasts, fungi, protozoa etc., are publicly available on the World Wide Web at ncbi.nlm.nih.gov/genomes. In another embodiment, marker molecules are nucleic acids that have sequences that are absent from any known genome. The sequences of marker molecules can be randomly generated algorithmically.

In various embodiments the marker molecules can be naturally-occurring deoxyribonucleic acids (DNA), ribonucleic acids or artificial nucleic acid analogs (nucleic acid mimics) including peptide nucleic acids (PMA), morpholino nucleic acid, locked nucleic acids, glycol nucleic acids, and threose nucleic acids, which are distinguished from naturally-occurring DNA or RNA by changes to the backbone of the molecule or DNA mimics that do not have a phosphodiester backbone. The deoxyribonucleic acids can be from naturally-occurring genomes or can be generated in a laboratory through the use of enzymes or by solid phase chemical synthesis. Chemical methods can also be used to generate the DNA mimics that are not found in nature. Derivatives of DNA are that are available in which the phosphodiester linkage has been replaced but in which the deoxyribose is retained include but are not limited to DNA mimics having backbones formed by thioformacetal or a carboxamide linkage, which have been shown to be good structural DNA mimics. Other DNA mimics include morpholino derivatives and the peptide nucleic acids (PNA), which contain an N-(2-aminoethyl)glycine-based pseudopeptide backbone (Ann Rev Biophys Biomol Struct 24:167-183 [1995]). PNA is an extremely good structural mimic of DNA (or of ribonucleic acid [RNA]), and PNA oligomers are able to form very stable duplex structures with Watson-Crick complementary DNA and RNA (or PNA) oligomers, and they can also bind to targets in duplex DNA by helix invasion (Mol Biotechnol 26:233-248 [2004]. Another good structural mimic/analog of DNA analog that can be used as a marker molecule is phosphorothioate DNA in which one of the non-bridging oxygens is replaced by a sulfur. This modification reduces the action of endo- and exonucleases2 including 5' to 3' and 3' to 5' DNA POL 1 exonuclease, nucleases S1 and P1, RNases, serum nucleases and snake venom phosphodiesterase.

The length of the marker molecules can be distinct or indistinct from that of the sample nucleic acids, i.e., the length of the marker molecules can be similar to that of the sample genomic molecules, or it can be greater or smaller than that of the sample genomic molecules. The length of the marker molecules is measured by the number of nucleotide or nucleotide analog bases that constitute the marker molecule. Marker molecules having lengths that differ from those of the sample genomic molecules can be distinguished from source nucleic acids using separation methods known in the art. For example, differences in the length of the marker and sample nucleic acid molecules can be determined by electrophoretic separation, e.g., capillary electrophoresis. Size differentiation can be advantageous for quantifying and assessing the quality of the marker and sample nucleic acids. Preferably, the marker nucleic acids are shorter than the genomic nucleic acids, and of sufficient length to exclude them from being mapped to the genome of the sample. For example, as a 30 base human sequence is needed to uniquely map it to a human genome. Accordingly in certain embodiments, marker molecules used in sequencing bioassays of human samples should be at least 30 bp in length.

The choice of length of the marker molecule is determined primarily by the sequencing technology that is used to verify the integrity of a source sample. The length of the sample genomic nucleic acids being sequenced can also be considered. For example, some sequencing technologies employ clonal amplification of polynucleotides, which can require that the genomic polynucleotides that are to be clonally amplified be of a minimum length. For example, sequencing using the Illumina GAII sequence analyzer includes an in vitro clonal amplification by bridge PCR (also known as cluster amplification) of polynucleotides that have a minimum length of 110 bp, to which adaptors are ligated to provide a nucleic acid of at least 200 bp and less than 600 bp that can be clonally amplified and sequenced. In some embodiments, the length of the adaptor-ligated marker molecule is between about 200 bp and about 600 bp, between about 250 bp and 550 bp, between about 300 bp and 500 bp, or between about 350 and 450. In other embodiments, the length of the adaptor-ligated marker molecule is about 200 bp. For example, when sequencing fetal cfDNA that is present in a maternal sample, the length of the marker molecule can be chosen to be similar to that of fetal cfDNA molecules. Thus, in one embodiment, the length of the marker molecule used in an assay that comprises massively parallel sequencing of cfDNA in a maternal sample to determine the presence or absence of a fetal chromosomal aneuploidy, can be about 150 bp, about 160 bp, 170 bp, about 180 bp, about 190 bp or about 200 bp; preferably, the marker molecule is about 170 pp. Other sequencing approaches, e.g., SOLiD sequencing, Polony Sequencing and 454 sequencing use emulsion PCR to clonally amplify DNA molecules for sequencing, and each technology dictates the minimum and the maximum length of the molecules that are to be amplified. The length of marker molecules to be sequenced as clonally amplified nucleic acids can be up to about 600 bp. In some embodiments, the length of marker molecules to be sequenced can be greater than 600 bp.

Single molecule sequencing technologies, that do not employ clonal amplification of molecules, and are capable of sequencing nucleic acids over a very broad range of template lengths, in most situations do not require that the molecules to be sequenced be of any specific length. However, the yield of sequences per unit mass is dependent on the number of 3' end hydroxyl groups, and thus having relatively short templates for sequencing is more efficient than having long templates. If starting with nucleic acids longer than 1000 nt, it is generally advisable to shear the nucleic acids to an average length of 100 to 200 nt so that more sequence information can be generated from the same mass of nucleic acids. Thus, the length of the marker molecule can range from tens of bases to thousands of bases. The length of marker molecules used for single molecule sequencing can be up to about 25 bp, up to about 50 bp, up to about 75 bp, up to about 100 bp, up to about 200 bp, up to about 300 bp, up to about 400 bp, up to about 500 bp, up to about 600 bp, up to about 700 bp, up to about 800 bp, up to about 900 bp, up to about 1000 bp, or more in length.

The length chosen for a marker molecule is also determined by the length of the genomic nucleic acid that is being sequenced. For example, cfDNA circulates in the human bloodstream as genomic fragments of cellular genomic DNA. Fetal cfDNA molecules found in the plasma of pregnant women are generally shorter than maternal cfDNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). DNA isolated from urine with a standard silica-based method consists of two fractions, high molecular weight DNA, which originates from shed cells and low molecular weight (150-250 base pair) fraction of transrenal DNA (Tr-DNA) (Botezatu et al., Clin Chem. 46: 1078-1084, 2000; and Su et al., J Mol. Diagn. 6: 101-107, 2004). The application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). In embodiments, wherein cfDNA is the genomic nucleic acid that is sequenced, marker molecules that are chosen can be up to about the length of the cfDNA. For example, the length of marker molecules used in maternal cfDNA samples to be sequenced as single nucleic acid molecules or as clonally amplified nucleic acids can be between about 100 bp and 600. In other embodiments, the sample genomic nucleic acids are fragments of larger molecules. For example, a sample genomic nucleic acid that is sequenced is fragmented cellular DNA. In embodiments, when fragmented cellular DNA is sequenced, the length of the marker molecules can be up to the length of the DNA fragments. In some embodiments, the length of the marker molecules is at least the minimum length required for mapping the sequence read uniquely to the appropriate reference genome. In other embodiments, the length of the marker molecule is the minimum length that is required to exclude the marker molecule from being mapped to the sample reference genome.

In addition, marker molecules can be used to verify samples that are not assayed by nucleic acid sequencing, and that can be verified by common bio-techniques other than sequencing, e.g., real-time PCR.

Sample Controls (e.g., in Process Positive Controls for Sequencing and/or Analysis).

In various embodiments marker sequences introduced into the samples, e.g., as described above, can function as positive controls to verify the accuracy and efficacy of sequencing and subsequent processing and analysis.

Accordingly, compositions and method for providing an in-process positive control (IPC) for sequencing DNA in a sample are provided. In certain embodiments, positive controls are provided for sequencing cfDNA in a sample comprising a mixture of genomes are provided. An IPC can be used to relate baseline shifts in sequence information obtained from different sets of samples, e.g., samples that are sequenced at different times on different sequencing runs. Thus, for example, an IPC can relate the sequence information obtained for a maternal test sample to the sequence information obtained from a set of qualified samples that were sequenced at a different time.

Similarly, in the case of segment analysis, an IPC can relate the sequence information obtained from a subject for particular segment(s) to the sequence obtained from a set of qualified samples (of similar sequences) that were sequenced at a different time. In certain embodiments an IPC can relate the sequence information obtained from a subject for particular cancer-related loci to the sequence information obtained from a set of qualified samples (e.g., from a known amplification/deletion, and the like).

In addition, IPCs can be used as markers to track sample(s) through the sequencing process. IPCs can also provide a qualitative positive sequence dose value, e.g., NCV, for one or more aneuploidies of chromosomes of interest, e.g., trisomy 21, trisomy 13, trisomy 18 to provide proper interpretation, and to ensure the dependability and accuracy of the data. In certain embodiments IPCs can be created to comprise nucleic acids from male and female genomes to provide doses for chromosomes X and Y in a maternal sample to determine whether the fetus is male.

The type and the number of in-process controls depends on the type or nature of the test needed. For example, for a test requiring the sequencing of DNA from a sample comprising a mixture of genomes to determine whether a chromosomal aneuploidy exists, the in-process control can comprise DNA obtained from a sample known comprising the same chromosomal aneuploidy that is being tested. In some embodiments, the IPC includes DNA from a sample known to comprise an aneuploidy of a chromosome of interest. For example, the IPC for a test to determine the presence or absence of a fetal trisomy, e.g., trisomy 21, in a maternal sample comprises DNA obtained from an individual with trisomy 21. In some embodiments, the IPC comprises a mixture of DNA obtained from two or more individuals with different aneuploidies. For example, for a test to determine the presence or absence of trisomy 13, trisomy 18, trisomy 21, and monosomy X, the IPC comprises a combination of DNA samples obtained from pregnant women each carrying a fetus with one of the trisomies being tested. In addition to complete chromosomal aneuploidies, IPCs can be created to provide positive controls for tests to determine the presence or absence of partial aneuploidies.

An IPC that serves as the control for detecting a single aneuploidy can be created using a mixture of cellular genomic DNA obtained from a two subjects one being the contributor of the aneuploid genome. For example, an IPC that is created as a control for a test to determine a fetal trisomy, e.g., trisomy 21, can be created by combining genomic DNA from a male or female subject carrying the trisomic chromosome with genomic DNA with a female subject known not to carry the trisomic chromosome. Genomic DNA can be extracted from cells of both subjects, and sheared to provide fragments of between about 100-400 bp, between about 150-350 bp, or between about 200-300 bp to simulate the circulating cfDNA fragments in maternal samples. The proportion of fragmented DNA from the subject carrying the aneuploidy, e.g., trisomy 21, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. The IPC can comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18. The mixture of fragmented DNA is prepared for sequencing. Processing of the mixture of fragmented DNA can comprise preparing a sequencing library, which can be sequenced using any massively parallel methods in singleplex or multiplex fashion. Stock solutions of the genomic IPC can be stored and used in multiple diagnostic tests.

Alternatively the IPC can be created using cfDNA obtained from a mother known to carry a fetus with a known chromosomal aneuploidy. For example, cfDNA can be obtained from a pregnant woman carrying a fetus with trisomy 21. The cfDNA is extracted from the maternal sample, and cloned into a bacterial vector and grown in bacteria to provide an ongoing source of the IPC. The DNA can be extracted from the bacterial vector using restriction enzymes. Alternatively, the cloned cfDNA can be amplified by, e.g., PCR. The IPC DNA can be processed for sequencing in the same runs as the cfDNA from the test samples that are to be analyzed for the presence or absence of chromosomal aneuploidies.

While the creation of IPCs is described above with respect to trisomies, it will be appreciated that IPCs can be created to reflect other partial aneuploidies including for example, various segment amplification and/or deletions. Thus, for example, where various cancers are known to be associated with particular amplifications (e.g., breast cancer associated with 20Q13) IPCs can be created that incorporate those known amplifications.

Sequencing Methods

As indicated above, the prepared samples (e.g., Sequencing Libraries) are sequenced as part of the procedure for determining a sequence of interest and for evaluating copy number variation(s). Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample, e.g., cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample, e.g., cfDNA in a maternal test sample, using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample, e.g., cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the test sample, e.g., cfDNA in a maternal test sample, by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing 1,000 copies of the same template. In one embodiment, the randomly fragmented genomic DNA, e.g., cfDNA, is amplified using PCR before it is subjected to cluster amplification. Alternatively, an amplification-free genomic library preparation is used, and the randomly fragmented genomic DNA, e.g., cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp, e.g., 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length, e.g., 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105).

Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between 20 and 40 bp reads, e.g., 36 bp, are obtained from mapping the reads to the reference genome per sample. In one embodiment, all the sequence reads are mapped to all regions of the reference genome. In one embodiment, the tags that have been mapped to all regions, e.g., all chromosomes, of the reference genome are counted, and the CNV, i.e., the over- or under-representation of a sequence of interest, e.g., a chromosome or portion thereof, in the mixed DNA sample is determined. The method does not require differentiation between the two genomes.

The accuracy required for correctly determining whether a CNV, e.g., aneuploidy, is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. Other variations can result from using different protocols for the extraction and purification of the nucleic acids, the preparation of the sequencing libraries, and the use of different sequencing platforms. The present method uses sequence doses (chromosome doses, or segment doses) based on the knowledge of normalizing sequences (normalizing chromosome sequences or normalizing segment sequences), to intrinsically account for the accrued variability stemming from interchromosomal (intra-run), and inter-sequencing (inter-run) and platform-dependent variability. Chromosome doses are based on the knowledge of a normalizing chromosome sequence, which can be composed of a single chromosome, or of two or more chromosomes selected from chromosomes 1-22, X, and Y. Alternatively, normalizing chromosome sequences can be composed of a single chromosome segment, or of two or more segments of one chromosome or of two or more chromosomes. Segment doses are based on the knowledge of a normalizing segment sequence, which can be composed of a single segment of any one chromosome, or of two or more segments of any two or more of chromosomes 1-22, X, and Y.

Apparatus and Systems for Determining Sequence of Interest

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for determining one or more conditions of a fetus related to a sequence of interest. The computer product may contain instructions for performing any one or more of the above-described methods for determining a sequence of interest for the fetus. As explained, the computer product may include a non-transitory and/or tangible computer readable medium having a computer executable or compilable logic (e.g., instructions) recorded thereon for enabling a processor to determine chromosome doses and, in some cases, whether a fetal aneuploidy is present or absent. In one example, the computer product comprises (1) a computer readable medium having a computer executable or compilable logic (e.g., instructions) recorded thereon for enabling a processor to diagnose a fetal aneuploidy comprising: a receiving procedure for receiving sequencing data from at least a portion of nucleic acid molecules from a maternal biological sample, wherein said sequencing data comprises a calculated sequence tag counts for libraries obtained from maternal cellular DNA and cfDNA; (2) computer assisted logic for analyzing a sequence of interest from said received data; and (3) an output procedure for generating an output indicating the conditions related to the sequence of interest.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable aneuploidy calls generally require mapping thousands (e.g., at least about 10,000) or even millions of reads to one or more chromosomes.

The methods disclosed herein can be performed using a system for evaluating a genetic sequence of interest for a fetus using cellular and cell free DNA from the mother. The system comprising: (a) a sequencer for receiving nucleic acids from the test sample providing nucleic acid sequence information from the sample; (b) a processor; and (c) one or more computer-readable storage media having stored thereon instructions for execution on said processor to evaluate sequence of interest for a fetus using cellular and cell free DNA from the mother. The instructions can specify one or more of the methods set forth herein. Accordingly, a system of the present disclosure can provide an automated system for carrying out a method set forth herein.

In some embodiments, the methods are instructed by a computer-readable medium having stored thereon computer-readable instructions for carrying out a method for determining conditions of a fetus related to a sequence of interest, e.g. carrying two copies of a disease causing allele. Thus one embodiment provides a computer program product comprising one or more computer-readable non-transitory storage media having stored thereon computer-executable instructions that, when executed by one or more processors of a computer system, cause the computer system to implement a method for determining a condition of a fetus related to a sequence of interest. The method includes: (a) obtaining sequence reads of mother-only cellular DNA obtained from the mother carrying the fetus, the cellular DNA having been specifically enriched for a sequence of interest; (b) computing a count of sequence tags mapping to the sequence of interest for the cellular DNA; (c) obtaining sequence reads of mother-and-fetus mixed cfDNA obtained from the mother, the cfDNA having been specifically enriched for the sequence of interest; (d) computing a count of sequence tags mapping to the sequence of interest for the cfDNA; (e) comparing the sequence tag counts mapping to the sequence of interest between the cellular DNA and the cfDNA; and (f) determining the condition of the fetus related to the sequence of interest.

In some embodiments, the method includes: obtaining sequence reads of fetal cellular DNA obtained from the mother carrying the fetus; computing a count of sequence tags mapping to the sequence of interest for the fetal cellular DNA; obtaining sequence reads of mother-and-fetus mixed cfDNA obtained from the mother; computing a count of sequence tags mapping to the sequence of interest for the mixed cfDNA; and determining the condition of the fetus related to the sequence of interest based on the sequence tag counts mapping to the sequence of interest for the fetal cellular DNA and the mixed cfDNA.

In some embodiments, the instructions may further include automatically recording information pertinent to the method such as fetal fraction and the presence or absence of a genetic disorder in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

Disclosed methods can also be performed using a computer processing system which is adapted or configured to perform a method for determining a fetal condition related to a sequence of interest, e.g., a genetic disorder or a fetal fraction. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:
 Reads obtained by sequencing nucleic acids in a test sample;
 Tracking information that correlates indexes with the identity of samples or subfractions of samples;
 Tags obtained by aligning reads to a reference genome or other reference sequence or sequences;
 The reference genome or sequence;
 Sequence tag density—Counts or numbers of tags for each of two or more regions (typically chromosomes or chromosome segments) of a reference genome or other reference sequences;
 Diagnoses (clinical condition associated with the calls);
 Recommendations for further tests derived from the calls and/or diagnoses;
 Quality metrics for samples, sequence data derived therefrom or diagnoses; and/or
 Treatment and/or monitoring plans derived from the calls and/or diagnoses.

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to determine conditions related to the sequence of interest. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate aneuploidy calls.

Among the processing operations that may be employed at distinct locations are the following:
 Sample collection;
 Sample processing preliminary to sequencing;
 Sequencing;
 Analyzing sequence data and deriving aneuploidy calls;
 Diagnosis;
 Reporting a diagnosis and/or a call to patient or health care provider;
 Developing a plan for further treatment, testing, and/or monitoring;
 Executing the plan; and/or
 Counseling.

Any one or more of these operations may be automated as described elsewhere herein. Typically, the sequencing and the analyzing of sequence data and deriving aneuploidy calls will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of aneuploidy analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of aneuploidy analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an aneuploidy analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., the fetus has Downs syndrome or the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of aneuploidy operation. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 15:
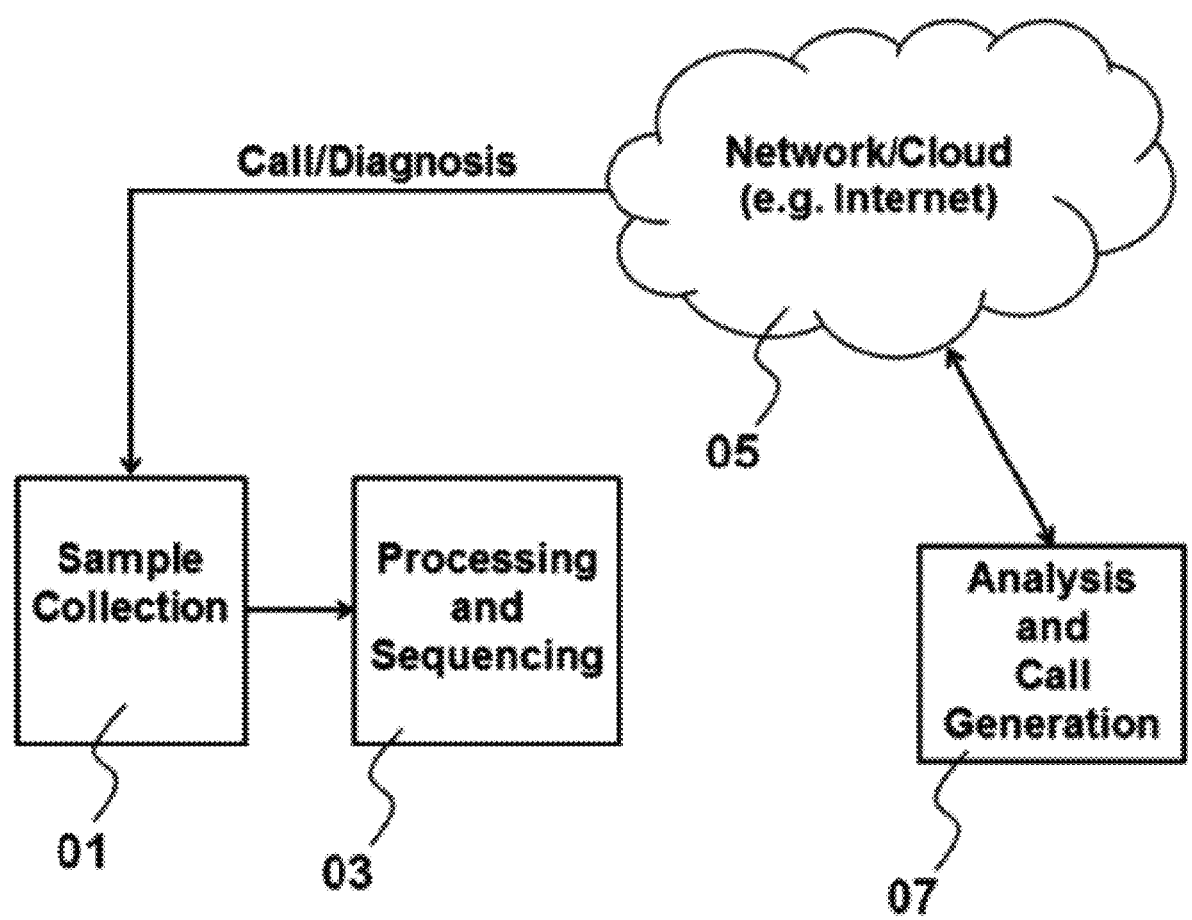
FIG. 15 is a block diagram of a dispersed system for processing a test sample and ultimately making a diagnosis.

FIG. 15 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 15.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 15. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 16:
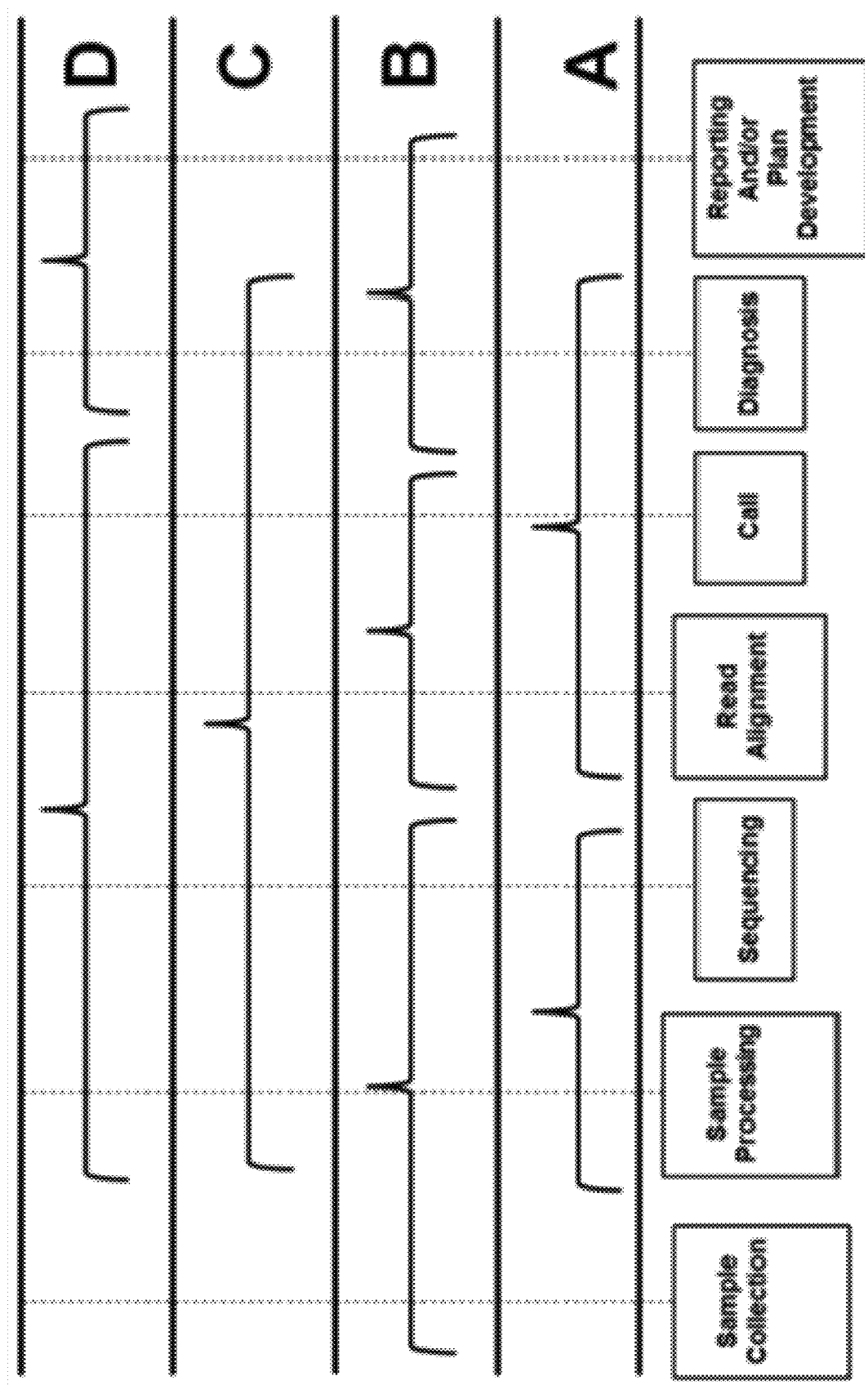
FIG. 16 schematically illustrates how different operations in processing test samples may be grouped to be handled by different elements of a system.

FIG. 16 elaborates on the options for performing various operations at distinct locations. In the most granular sense depicted in FIG. 16, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 16 identified by reference character A. In another implementation, which is identified by character B in FIG. 16, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 16, sample collection is performed at a first location, sample processing, sequencing, read alignment, calling, and diagnosis are all performed together at a second location, and reporting and/or plan development are performed at a third location. Finally, in the implementation labeled D in FIG. 16, sample collection is performed at a first location, sample processing, sequencing, read alignment, and calling are all performed at a second location, and diagnosis and reporting and/or plan management are performed at a third location.

One embodiment provides a system for use in determining a condition of a fetus related to a sequence of interest using maternal-only nucleic acid (e.g. maternal cellular DNA) and mixed maternal-fetal nucleic acid (e.g. cfDNA) from a maternal sample, the system including a sequencer for receiving a nucleic acid sample and providing fetal and maternal nucleic acid sequence information from the sample; a processor; and a machine readable storage medium comprising instructions for execution on said processor, the instructions comprising: (a) code for obtaining sequence reads of maternal-only nucleic acid obtained from the mother carrying the fetus, the maternal-only nucleic acid having been optionally enriched for a specific sequence of interest; (b) code for computing a count of sequence tags mapping to the sequence of interest for the maternal-only nucleic acid; (c) code for obtaining sequence reads of maternal-fetal mixed nucleic acid obtained from the mother, the maternal-fetal mixed nucleic acid having, optionally, been specifically enriched for the sequence of interest; (d) code for computing a count of sequence tags mapping to the sequence of interest for the maternal-fetal mixed nucleic acid; (e) code for comparing the sequence tag counts mapping to the sequence of interest between the cellular maternal-only nucleic acid and the maternal-fetal mixed nucleic acid; and (f) code for determining the condition of the fetus related to the sequence of interest.

In some alternative embodiments, the instructions comprise: (a) code for obtaining sequence reads of fetal cellular DNA obtained from the mother carrying the fetus; (b) code for computing a count of sequence tags mapping to the sequence of interest for the fetal cellular DNA; (c) code for obtaining sequence reads of mother-and-fetus mixed cfDNA obtained from the mother; (d) code for computing a count of sequence tags mapping to the sequence of interest for the mixed cfDNA; and (e) code for determining the condition of the fetus related to the sequence of interest based on the sequence tag counts mapping to the sequence of interest for the fetal cellular DNA and the mixed cfDNA.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

EXAMPLE 1

Preparation and Sequencing of Primary and Enriched Sequencing Libraries a. Preparation of Sequencing Libraries—Abbreviated Protocol (ABB)

All sequencing libraries, i.e., primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl 1 deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl l of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl l of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA (25 µl) using Phusion® High-Fidelity Master Mix (25 µl; Finnzymes, Woburn, Mass.) and Illumina's PCR primers (0.5 µM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Preparation of Sequencing Libraries—Full-Length Protocol

The full-length protocol described here is essentially the standard protocol provided by Illumina, and only differs from the Illumina protocol in the purification of the amplified library. The Illumina protocol instructs that the amplified library be purified using gel electrophoresis, while the protocol described herein uses magnetic beads for the same purification step. Approximately 2 ng of purified cfDNA extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt magnetic beads and reagents instead of the purification column, were performed according to the protocol accompanying the NEBNext™ Reagents for Sample Preparation for a genomic DNA library that is sequenced using the Illumina® GAII. The NEBNext™ protocol essentially follows that provided by Illumina, which is available at grcf.jhml.edu/hts/protocols/11257047_ChIP_Sample Prep.pdf.

Figure 17A:
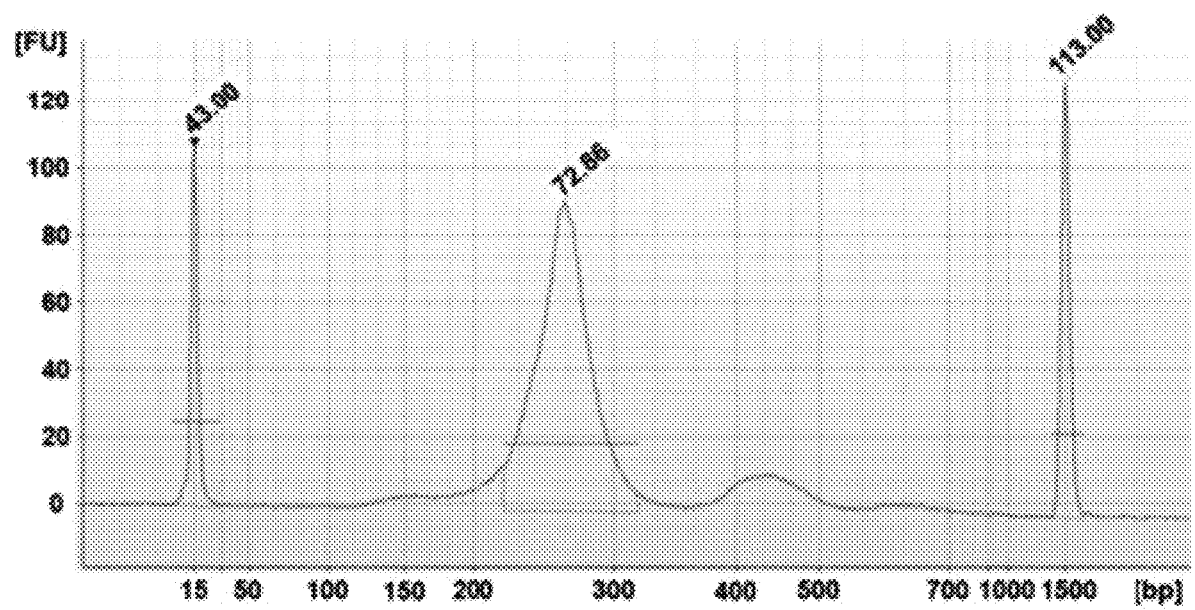
FIGS. 17A and 17B show electropherograms of a cfDNA sequencing library prepared according to the abbreviated protocol described in Example 1a (FIG. 17A), and the protocol described in Example 1b (FIG. 17B).
Figure 17B:
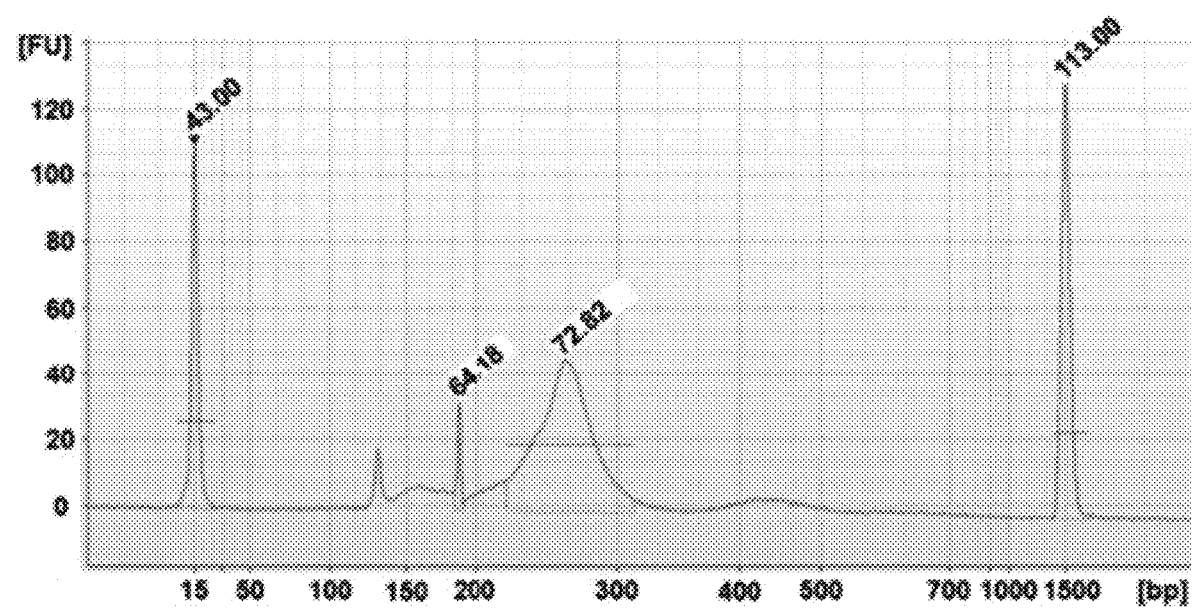

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µl reaction was transferred to 1.5 ml microfuge tube, and 250 µl of Qiagen Buffer PB were added. The resulting 300 µl were transferred to a QlAquick column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEBNext® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.).

c. Analysis of Sequencing Libraries Prepared According to the Abbreviated (a) and the Full-Length (b) Protocols The electropherograms generated by the Bioanalyzer are shown in FIGS. 17A and 17B. FIG. 17A shows the electropherogram of library DNA prepared from cfDNA purified from plasma sample M24228 using the full-length protocol described in (a), and FIG. 17B shows the electropherogram of library DNA prepared from cfDNA purified from plasma sample M24228 using the full-length protocol described in (b). In both figures, peaks 1 and 4 represent the 15 bp Lower Marker, and the 1,500 Upper Marker, respectively; the numbers above the peaks indicate the migration times for the library fragments; and the horizontal lines indicate the set threshold for integration. The electropherogram in FIG. 17A shows a minor peak of fragments of 187 bp and a major peak of fragments of 263 bp, while the electropherogram in FIG. 17B shows only one peak at 265 bp. Integration of the peak areas resulted in a calculated concentration of 0.40 ng/µl for the DNA of the 187 bp peak in FIG. 17A, a concentration of 7.34 ng/µl for the DNA of the 263 bp peak in FIG. 17A, and a concentration of 14.72 ng/µl for the DNA of the 265 bp peak in FIG. 17B. The Illumina adaptors that were ligated to the cfDNA are known to be 92 bp, which when subtracted from the 265 bp, indicate that the peak size of the cfDNA is 173 bp. It is possible that the minor peak at 187 bp represents fragments of two primers that were ligated end-to-end. The linear two-primer fragments are eliminated from the final library product when the abbreviated protocol is used. The abbreviated protocol also eliminates other smaller fragments of less than 187 bp. In this example, the concentration of purified adaptor-ligated cfDNA is double that of the adaptor-ligated cfDNA produced using the full-length protocol. It has been noted that the concentration of the adaptor-ligated cfDNA fragments was always greater than that obtained using the full-length protocol (data not shown).

Thus, an advantage of preparing the sequencing library using the abbreviated protocol is that the library obtained consistently comprises only one major peak in the 262-267 bp range while the quality of the library prepared using the full-length protocol varies as reflected by the number and mobility of peaks other than that representing the cfDNA. Non-cfDNA products would occupy space on the flow cell and diminish the quality of the cluster amplification and subsequent imaging of the sequencing reactions, which underlies the overall assignment of the aneuploidy status. The abbreviated protocol was shown not to affect the sequencing of the library.

Another advantage of preparing the sequencing library using the abbreviated protocol is that the three enzymatic steps of blunt-ending, d-A tailing, and adaptor-ligation, take less than an hour to complete to support the validation and implementation of a rapid aneuploid diagnostic service.

Another advantage is that the three enzymatic steps of blunt-ending, d-A tailing, and adaptor ligation, are performed in the same reaction tube, thus avoiding multiple sample transfers that would potentially lead to loss of material, and more importantly to possible sample mix-up and sample contamination.

EXAMPLE 2

Determining srv Gene Using Fetal Cellular DNA and Mother-and-Fetus cfDNA

This example illustrates that the methods and systems disclosed herein may be used to determine a Y-chromosome specific sry gene using cfDNA and fetal cellular DNA obtained from a maternal blood sample.

Figure 18:
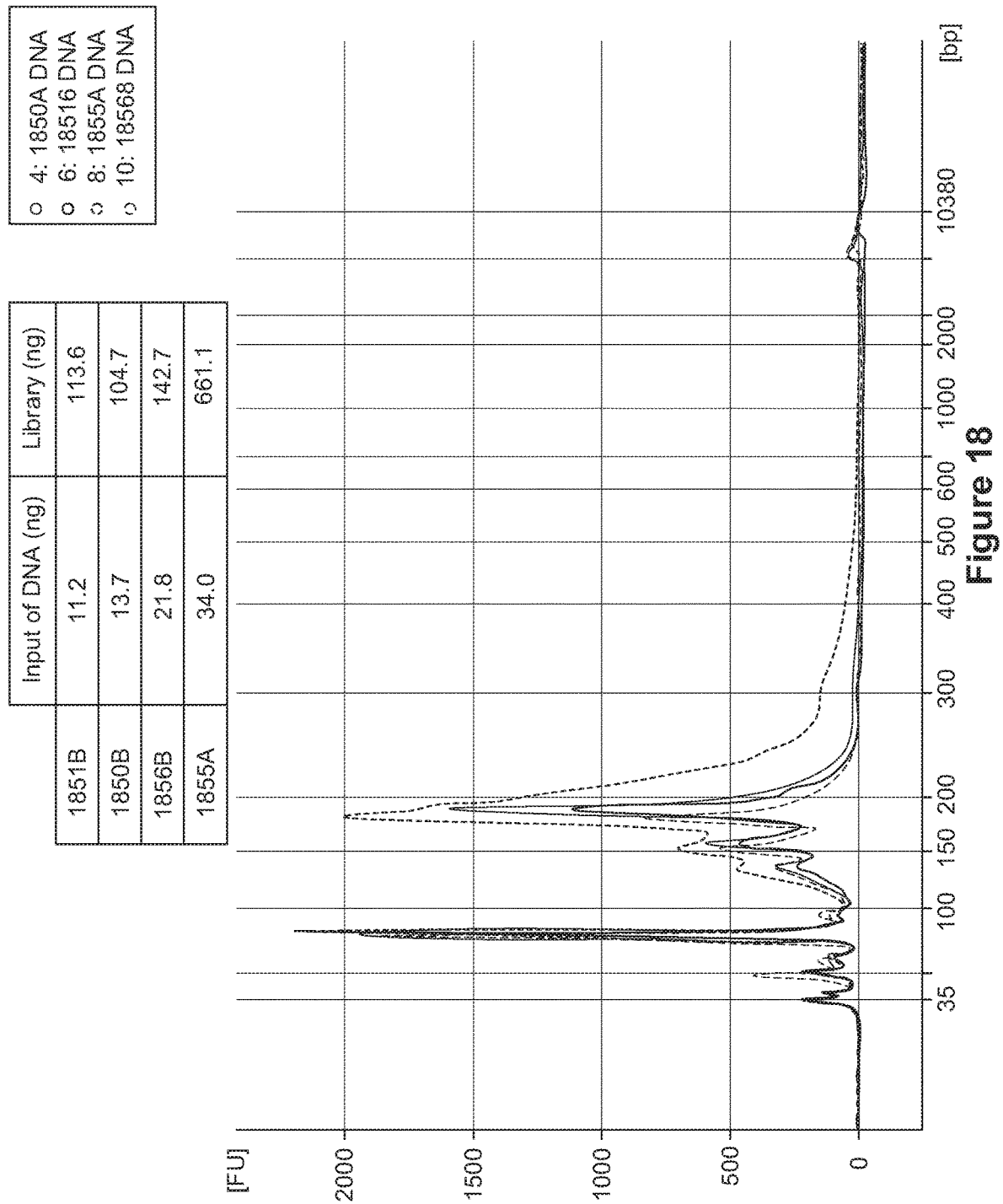
FIG. 18 shows the relative frequency of sequence length for four libraries made from purified cfDNA according to one example of the disclosure.

In this example, cfDNA are isolated and indexed cfDNA library are prepared from the isolated cfDNA. In this example, the plasma or serum from maternal blood sample was harvested by a low-speed centrifugation at 1,600 g. A maternal blood sample was spin for 15 mins at 4° C. Then the upper layer of plasma was removed, then the plasma was spun 2 times for 10 mins. at 16,000 g to ensure removal of all cellular sources of DNA. Then Tn5 mediated transposon tagging (Nextera) was used to create an indexed sequencing library directly from 15 ul of prespun plasma or serum (or kit purified cell free DNA). NGS libraries prepared from purified cfDNA as shown in are shown in FIG. 18.

In addition, circulating fetal NRBCs are isolated using a magnetic sweeping device which is capable of isolating circulating fetal cells from maternal blood. This process for isolating live nucleated fetal red blood cells is outlined in the following steps: (a) labeling of all cellular nuclei in a maternal blood sample with Hoechst; (b) differential red blood lysis of maternal red blood cells—using acetazolamide treatment to protect fetal nucleated red blood cells from red blood cell lysis; (c) fetal nucleated red blood cells were labeled using magnetic beads coated with an antibody that recognizes a cell surface marker present on fetal red blood surfaces, and fluorescently tagged using labeled antibodies to markers on the surfaces of fetal red blood cells. Preparations of fetal cells were then enriched using a magnetic sweeping device, and (d) imaging and isolation of fetal NRBCs was accomplished using an image guided cell isolation device.

Then, purified fetal cell were lysed and indexed library was prepared from the lysed fetal NRBCs. Single purified fetal NRBC or small pools of cells (<100 cells) were lysed and their DNA was released by incubating for 6 min. in Quick Extract Buffer (Epicentre) followed by incubation at 95° C. for 2 min to inactivate proteinase K in extraction buffer. Then the example used Tn5 mediated transposon tagging (Nextera) to create an indexed sequencing library directly from the fetal cell lysates. The index for the cellular DNA library is different from the index for the mixed cfDNA.

The example involved mixing indexed cfDNA library and indexed purified fetal cell library, quantification, and clustering on a sequencing platform by Illumina. Uniquely indexed cfDNA and fetal cell libraries were mixed and the sample quantified using qPCR. Samples was clustered on an lllumina flow cell using the cBot.

Then sequencing and bioinformatics were performed on the libraries. Flow cells were subjected to lllumina paired end sequencing. Quality filtering of NGS reads and index decoding was performed. Fetal read data was aligned to reference chromosomes. Sequence reads were counted to detect chromosomal anueploidy in cfDNA and fetal cell DNA. Paired end read analysis was used to detect chromosomal rearrangements in fetal cell DNA. High resolution sequence analysis was performed, using indexed purified fetal cell sequence to detect indels, copy number variation, SNPs and other sequence changes that were of diagnostic value.

Using qPCR for the Y chromosome specific gene sry, a strong correlation was found between the presence of sry in cfDNA and isolated fetal cells from the same sample when the fetus is male. FIG. 19 shows the data obtained for 9 subjects. These data indicated that one can obtain information of diagnostic value from both cfDNA and isolated fetal cells from the same sample.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for determining at least one sequence of interest of a fetus of a pregnant mother, the method comprising:
 (a) obtaining cellular DNA from a blood sample of the pregnant mother, wherein the cellular DNA comprises fetal cellular DNA;
 (b) obtaining mother-and-fetus mixed cfDNA from the blood sample of the pregnant mother;
 (c) applying an indicator to at least one of the fetal cellular DNA and the mixed cfDNA, wherein the indicator identifies a source of DNA as being from the fetal cellular DNA or the mixed cfDNA;
 (d) combining the fetal cellular DNA and the mixed cfDNA to provide a sample of combined cellular DNA and cfDNA;
 (e) sequencing the sample of combined cellular DNA and cfDNA to provide a plurality of sequence tags; and
 (f) analyzing the plurality of sequence tags to determine a presence and/or abundance of the at least one sequence of interest in the fetus's DNA, wherein at least a portion of the plurality of sequence tags map to the at least one sequence of interest.

2. The method of claim 1, wherein (e) sequencing said sample of combined cellular and cfDNA comprises: sequencing said sample of combined cellular and cfDNA to produce a plurality of sequence reads; and aligning the plurality of sequence reads to a reference sequence to provide the plurality of sequence tags, wherein sources of the plurality of sequence tags are indicated by the indicator identifying the source of DNA.

3. The method of claim 1, wherein the fetal cellular DNA is obtained from one or more fetal nucleated red blood cells (NRBCs) in the blood of the pregnant mother.

4. The method of claim 3, further comprising separating the fetal NRBCs from maternal erythrocytes in a cellular component of a blood sample of the pregnant mother.

5. The method of claim 4, wherein separating the fetal NRBCs from the maternal erythrocytes comprises differentially lysing maternal erythrocytes.

6. The method of claim 4, wherein separating the fetal NRBCs from the maternal erythrocytes comprises size-based separation and/or capture-based separation.

7. The method of claim 6, wherein the capture-based separation comprises capturing the fetal NRBCs through binding one or more cellular markers expressed by fetal NRBCs.

8. The method of claim 7, wherein the one or more cellular markers expressed by fetal NRBCs are selected from the group consisting of CD71, CD36, CD34, antigen-i, galactose, glycophorin-A, fetal haemoglobin, and any combinations thereof.

9. The method of claim 7, wherein the one or more cellular markers comprise a surface marker expressed by fetal NRBCs but not, or to a lesser degree, by maternal NRBCs.

10. The method of claim 7, wherein the one or more cellular markers comprises a 4B9-antigen and/or a 4B8-antigen.

11. A method, implemented at a computer system that includes one or more processors and system memory, for determining a condition of a fetus related to a sequence of interest, the method comprising:
- obtaining, by the computer system, sequence reads of fetus-only cellular DNA obtained from a blood sample of a mother carrying the fetus;
- computing, by the computer system, a count of sequence tags mapping to the sequence of interest for the cellular DNA;
- obtaining, by the computer system, sequence reads of mother-and-fetus mixed cfDNA obtained from the mother;
- computing, by the computer system, a count of sequence tags mapping to the sequence of interest for the cfDNA;
- comparing, by the computer system, the sequence tag counts mapping to the sequence of interest between the cellular DNA and the cfDNA; and
- determining, by the computer system, the condition of the fetus related to the sequence of interest.

12. The method of claim 11, wherein the cellular DNA and the cfDNA were combined for amplification and/or sequencing.

13. A computer program product comprising a non-transitory machine readable medium storing program code that, when executed by one or more processors of a computer system, causes the computer system to implement a method for determining a zygosity case of a sequence of interest for a fetus, said program code comprising:
- code for obtaining sequence reads of fetal cellular DNA obtained from a mother carrying the fetus;
- code for computing a count of sequence tags mapping to the sequence of interest for the fetal cellular DNA;
- code for obtaining sequence reads of mother-and-fetus mixed cfDNA obtained from the mother;
- code for computing a count of sequence tags mapping to the sequence of interest for the cfDNA;
- code for comparing the sequence tag counts mapping to the sequence of interest between the cellular DNA and the cfDNA; and
- code for determining the condition of the fetus related to the sequence of interest.

14. The method of claim 11, further comprising determining a fetal zygosity of the sequence of interest.

15. The method of claim 14, wherein determining the fetal zygosity comprises determining that the mother is heterozygous and the fetus is homozygous.

16. The method of claim 15, further comprising determining a fetal fraction assuming the fetal zygosity.

17. The method of claim 11, wherein comparing the sequence tag counts comprises obtaining a test-difference-value based on a difference of counts of test sequence tags derived from the cellular DNA vs. the cfDNA.

18. The method of claim 17, wherein the test-difference-value is obtained by subtraction or division.

19. The method of claim 11, further comprising determining whether the fetus has a genetic disease based on the sequence of interest of the fetus.

20. The method of claim 19, wherein determining whether the fetus has the genetic disease comprises determining whether the fetus is homozygous in a disease causing allele within the sequence of interest when the mother is heterozygous of the same allele.

21. The method of claim 11, wherein the sequence of interest comprises a site of an allele associated with a disease.

22. The method of claim 21, wherein the sequence of interest comprises a single nucleotide polymorphism, a tandem repeat, a micro-deletion, an insertion, an indel, or any combinations thereof.

23. The method of claim 21, further comprising determining if the fetus is homozygous or heterozygous for the disease associated allele.

24. The method of claim 11, wherein the method further comprises:
- obtaining sequence tags derived from the cellular DNA and the cfDNA for a plurality of training sequences;
- obtaining training-difference-values based on differences of counts of the sequence tags derived from the cellular DNA and the cfDNA for the plurality of training sequences;
- obtaining distribution statistics of the training-difference-values; and
- using the distribution statistics of the training-difference-values to determine a zygosity of the sequence of interest for the fetus.

* * * * *